(12) United States Patent
Zhu et al.

(10) Patent No.: US 7,465,564 B2
(45) Date of Patent: Dec. 16, 2008

(54) PRODUCTION OF γ-LINOLENIC ACID IN OLEAGINOUS YEAST

(75) Inventors: Quinn Qun Zhu, West Chester, PA (US); Dana M. Walters Pollak, Media, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/198,975

(22) Filed: Aug. 8, 2005

(65) Prior Publication Data

US 2006/0035351 A1 Feb. 16, 2006

Related U.S. Application Data

(60) Provisional application No. 60/600,270, filed on Aug. 10, 2004.

(51) Int. Cl.
*C12Q 1/68* (2006.01)
*C07H 21/04* (2006.01)
*C12P 21/06* (2006.01)

(52) U.S. Cl. .............. 435/134; 435/254.2; 435/252.3; 435/69.2; 536/23.2

(58) Field of Classification Search .............. 435/134, 435/254.2; 536/23.2
See application file for complete search history.

(56) References Cited

U.S. PATENT DOCUMENTS

| | | | |
|---|---|---|---|
| 4,666,701 A | 5/1987 | Horrobin et al. | |
| 4,758,592 A | 7/1988 | Horrobin et al. | |
| 5,116,871 A | 5/1992 | Horrobin et al. | |
| 6,136,574 A | 10/2000 | Knutzon et al. | |
| 2005/0136519 A1* | 6/2005 | Picataggio et al. | 435/134 |
| 2005/0216975 A1* | 9/2005 | Yadav et al. | 800/281 |

FOREIGN PATENT DOCUMENTS

EP 0 005 277 B1 1/1982

OTHER PUBLICATIONS

Juretzek T et al., Vectors for gene expression and amplification in the yeast Yarrowia lipolyticaYeast. Jan. 30, 2001;18(2):97-113.*
Domergue et al., Cloning and functional characterization of Phaeodactylum tricomutum front-end desaturases involved in eicosapentaenoic acid biosynthesis. Eur J Biochem. Aug. 2002;269(16):4105-13.*
Qi. B, et al.,Production of very long chain polyunsaturated omega-3 and omega-6 fatty acids in plants.Nat Biotechnol. Jun. 2004;22(6).*
Damude et al., Identification of bifunctional Δ12/ω3 fatty acid desaturases for improving the ratio of ω3 to ω6 fatty acids in microbes and plants Proc Natl Acad Sci U S A. Jun. 20, 2006; 103(25): 9446-9451.*
Brenner et. al., Regulatory Function of 6 Desaturase—Key Enzyme of Polyunsaturated Fatty Acids Synthesis, Adv. Exp. Med. Biol., 1976, pp. 85-101, vol. 83.
J.E. Simon et. al., Borage: A Source of Gamma Linolenic Acid, Advances in New Crops, 1990, p. 528.
C. Ratledge, Single Cell Oils—Have They A Biotechnological Future, Trends Biotech., 1993, pp. 278-284, vol. 11.
C. Ratledge, Microbial Oils and Fats: An Assessment of Their Commerical Potential, Prog. Ind. Microbiol., 1982, pp. 119-206, vol. 16.
Yasunari Michinaka et. al., Production of Polyunsaturated Fatty Acids by Genetic Engineering of Yeast, Journal of Oleo Science, 2001, pp. 359-365, vol. 50.

* cited by examiner

*Primary Examiner*—Joseph Woitach
*Assistant Examiner*—Maria Leavitt

(57) ABSTRACT

The present invention relates to methods for the production of γ-linolenic acid (GLA) in oleaginous yeast. Thus, Δ12 and Δ6 desaturases able to catalyze the conversion of oleic acid to GLA have been introduced into the genome of *Yarrowia*, using zeta-directed integration. Transformed strains produced over 25% GLA in the total lipids, as opposed to wild-type *Yarrowia* that is unable to synthesize any GLA. Metabolic engineering and fermentation methods are provided to further enhance GLA productivity in oleaginous yeast.

12 Claims, 6 Drawing Sheets

SEQUENCE LISTING

<160> NUMBER OF SEQ ID NOS: 48

<210> SEQ ID NO 1
<211> LENGTH: 35
<212> TYPE: DNA
<213> ORGANISM: Artificial Sequence
<220> FEATURE:
<223> OTHER INFORMATION: Primer YL127

<400> SEQUENCE: 1
tttggcgcgc ctgtgcgtac cagggatagg gtagg          35

<210> SEQ ID NO 2
<211> LENGTH: 32
<212> TYPE: DNA
<213> ORGANISM: Artificial Sequence
<220> FEATURE:
<223> OTHER INFORMATION: Primer YL128

<400> SEQUENCE: 2
tttcgtacgg accacctccc ttgcacttct tg             32

<210> SEQ ID NO 3
<211> LENGTH: 32
<212> TYPE: DNA
<213> ORGANISM: Artificial Sequence
<220> FEATURE:
<223> OTHER INFORMATION: Primer YL129

<400> SEQUENCE: 3
gggttaatta acgccgattc tctctgcagt cg             32

<210> SEQ ID NO 4
<211> LENGTH: 31
<212> TYPE: DNA
<213> ORGANISM: Artificial Sequence
<220> FEATURE:
<223> OTHER INFORMATION: Primer YL130

<400> SEQUENCE: 4
tttgcatgct ctggagagtt agtcatccga c              31

<210> SEQ ID NO 5
<211> LENGTH: 265
<212> TYPE: DNA
<213> ORGANISM: Yarrowia lipolytica

<400> SEQUENCE: 5
tgtgcgtacc agggataggg taggtagtga aatctgagtt agtacatcaa ctctagacga    60

```
tgggcgtcgc tgtgtagaag aacaataact cacccggtaa ctaacactat ttctcggtgg    120
tcaatgcgtc agaagatatc aagacggtcc gttttgcgtt taagccgagt gaatgttgcc    180
tgccgttagt aaatttatta tgaaaaaccc cactatgaat acatcagcct atactgatat    240
accaagaagt gcaagggagg tggtc                                          265

<210> SEQ ID NO 6
<211> LENGTH: 359
<212> TYPE: DNA
<213> ORGANISM: Yarrowia lipolytica

<400> SEQUENCE: 6
taacgccgat tctctctgca gtcgtaagac ccaggtggtg tgtccgaggc agtatcgctt     60
tcccaactct agtaacctcg gtagtgtgag acacactacc cctaacgtta ggacagccgg    120
acgacgatgg cgcagcaatt tggcgaacgc tgttataaaa caattcactt acgtgcaatg    180
aaagttgttt gggcaataaa caataaatgt attagagcca gacgatagac aacaatccag    240
cagatgatga gcaggaaaat tgagtaagat cgacgtggca agaagagtta cagttacgca    300
gagttaataa ggtgttggga gattagagtt accctgtcgg atgactaact ctccagagc    359

<210> SEQ ID NO 7
<211> LENGTH: 1374
<212> TYPE: DNA
<213> ORGANISM: Mortierella alpina
<220> FEATURE:
<221> NAME/KEY: CDS
<222> LOCATION: (1)..(1374)

<400> SEQUENCE: 7 atg gct gcc gct ccc tct gtg cga acc ttt acc cga gcc gag gtt ctg     48
Met Ala Ala Ala Pro Ser Val Arg Thr Phe Thr Arg Ala Glu Val Leu
1               5                   10                  15 aac gct gag gct ctg aac gag ggc aag aag gac gct gag gct ccc ttc     96
Asn Ala Glu Ala Leu Asn Glu Gly Lys Lys Asp Ala Glu Ala Pro Phe
            20                  25                  30 ctg atg atc atc gac aac aag gtg tac gac gtc cga gag ttc gtc cct    144
Leu Met Ile Ile Asp Asn Lys Val Tyr Asp Val Arg Glu Phe Val Pro
        35                  40                  45 gac cat cct gga ggc tcc gtg att ctc acc cac gtt ggc aag gac ggc    192
Asp His Pro Gly Gly Ser Val Ile Leu Thr His Val Gly Lys Asp Gly
    50                  55                  60 acc gac gtc ttt gac acc ttt cat ccc gag gct gct tgg gag act ctc    240
Thr Asp Val Phe Asp Thr Phe His Pro Glu Ala Ala Trp Glu Thr Leu
65                  70                  75                  80 gcc aac ttc tac gtt gga gac att gac gag tcc gac cga gac atc aag    288
Ala Asn Phe Tyr Val Gly Asp Ile Asp Glu Ser Asp Arg Asp Ile Lys
                85                  90                  95 aac gat gac ttt gcc gct gag gtc cga aag ctg cga acc ctg ttc cag    336
Asn Asp Asp Phe Ala Ala Glu Val Arg Lys Leu Arg Thr Leu Phe Gln
            100                 105                 110 tct ctc ggc tac tac gac tcc tct aag gcc tac tac gcc ttc aag gtc    384
Ser Leu Gly Tyr Tyr Asp Ser Ser Lys Ala Tyr Tyr Ala Phe Lys Val
        115                 120                 125 tcc ttc aac ctc tgc atc tgg gga ctg tcc acc gtc att gtg gcc aag    432
Ser Phe Asn Leu Cys Ile Trp Gly Leu Ser Thr Val Ile Val Ala Lys
    130                 135                 140 tgg ggt cag acc tcc acc ctc gcc aac gtg ctc tct gct gcc ctg ctc    480
Trp Gly Gln Thr Ser Thr Leu Ala Asn Val Leu Ser Ala Ala Leu Leu
145                 150                 155                 160
```

```
ggc ctg ttc tgg cag cag tgc gga tgg ctg gct cac gac ttt ctg cac      528
Gly Leu Phe Trp Gln Gln Cys Gly Trp Leu Ala His Asp Phe Leu His
            165                 170                 175 cac cag gtc ttc cag gac cga ttc tgg ggt gat ctc ttc gga gcc ttc      576
His Gln Val Phe Gln Asp Arg Phe Trp Gly Asp Leu Phe Gly Ala Phe
        180                 185                 190 ctg gga ggt gtc tgc cag ggc ttc tcc tct tcc tgg tgg aag gac aag      624
Leu Gly Gly Val Cys Gln Gly Phe Ser Ser Ser Trp Trp Lys Asp Lys
    195                 200                 205 cac aac act cac cat gcc gct ccc aac gtg cat ggc gag gat cct gac      672
His Asn Thr His His Ala Ala Pro Asn Val His Gly Glu Asp Pro Asp
210                 215                 220 att gac acc cac cct ctc ctg acc tgg tcc gag cac gct ctg gag atg      720
Ile Asp Thr His Pro Leu Leu Thr Trp Ser Glu His Ala Leu Glu Met
225                 230                 235                 240 ttc tcc gac gtc ccc gat gag gag ctg acc cga atg tgg tct cga ttc      768
Phe Ser Asp Val Pro Asp Glu Glu Leu Thr Arg Met Trp Ser Arg Phe
                245                 250                 255 atg gtc ctg aac cag acc tgg ttc tac ttc ccc att ctc tcc ttc gct      816
Met Val Leu Asn Gln Thr Trp Phe Tyr Phe Pro Ile Leu Ser Phe Ala
            260                 265                 270 cga ctg tct tgg tgc ctc cag tcc att ctc ttt gtg ctg ccc aac ggt      864
Arg Leu Ser Trp Cys Leu Gln Ser Ile Leu Phe Val Leu Pro Asn Gly
        275                 280                 285 cag gct cac aag ccc tcc gga gct cga gtg ccc atc tcc ctg gtc gag      912
Gln Ala His Lys Pro Ser Gly Ala Arg Val Pro Ile Ser Leu Val Glu
    290                 295                 300 cag ctg tcc ctc gcc atg cac tgg acc tgg tac ctc gct acc atg ttc      960
Gln Leu Ser Leu Ala Met His Trp Thr Trp Tyr Leu Ala Thr Met Phe
305                 310                 315                 320 ctg ttc atc aag gat cct gtc aac atg ctc gtg tac ttc ctg gtg tct     1008
Leu Phe Ile Lys Asp Pro Val Asn Met Leu Val Tyr Phe Leu Val Ser
                325                 330                 335 cag gct gtg tgc gga aac ctc ctc gcc atc gtg ttc tcc ctc aac cac     1056
Gln Ala Val Cys Gly Asn Leu Leu Ala Ile Val Phe Ser Leu Asn His
            340                 345                 350 aac ggt atg cct gtg atc tcc aag gag gag gct gtc gac atg gat ttc     1104
Asn Gly Met Pro Val Ile Ser Lys Glu Glu Ala Val Asp Met Asp Phe
        355                 360                 365 ttt acc aag cag atc atc act ggt cga gat gtc cat cct gga ctg ttc     1152
Phe Thr Lys Gln Ile Ile Thr Gly Arg Asp Val His Pro Gly Leu Phe
    370                 375                 380 gcc aac tgg ttc acc ggt ggc ctg aac tac cag atc gag cat cac ctg     1200
Ala Asn Trp Phe Thr Gly Gly Leu Asn Tyr Gln Ile Glu His His Leu
385                 390                 395                 400 ttc cct tcc atg cct cga cac aac ttc tcc aag atc cag cct gcc gtc     1248
Phe Pro Ser Met Pro Arg His Asn Phe Ser Lys Ile Gln Pro Ala Val
                405                 410                 415 gag acc ctg tgc aag aag tac aac gtc cga tac cac acc act ggt atg     1296
Glu Thr Leu Cys Lys Lys Tyr Asn Val Arg Tyr His Thr Thr Gly Met
            420                 425                 430 atc gag gga act gcc gag gtc ttc tcc cga ctg aac gag gtc tcc aag     1344
Ile Glu Gly Thr Ala Glu Val Phe Ser Arg Leu Asn Glu Val Ser Lys
        435                 440                 445 gcc acc tcc aag atg ggc aag gct cag taa                             1374
Ala Thr Ser Lys Met Gly Lys Ala Gln
    450                 455

<210> SEQ ID NO 8
<211> LENGTH: 457
```

```
<212> TYPE: PRT
<213> ORGANISM: Mortierella alpina

<400> SEQUENCE: 8
```

| | | | | | | | | | | | | | | | |
|---|---|---|---|---|---|---|---|---|---|---|---|---|---|---|---|
| Met | Ala | Ala | Ala | Pro | Ser | Val | Arg | Thr | Phe | Thr | Arg | Ala | Glu | Val | Leu |
| 1 | | | | 5 | | | | | 10 | | | | | 15 | |
| Asn | Ala | Glu | Ala | Leu | Asn | Glu | Gly | Lys | Lys | Asp | Ala | Glu | Ala | Pro | Phe |
| | | | 20 | | | | | 25 | | | | | 30 | | |
| Leu | Met | Ile | Ile | Asp | Asn | Lys | Val | Tyr | Asp | Val | Arg | Glu | Phe | Val | Pro |
| | | 35 | | | | | 40 | | | | | 45 | | | |
| Asp | His | Pro | Gly | Gly | Ser | Val | Ile | Leu | Thr | His | Val | Gly | Lys | Asp | Gly |
| 50 | | | | | 55 | | | | | 60 | | | | | |
| Thr | Asp | Val | Phe | Asp | Thr | Phe | His | Pro | Glu | Ala | Ala | Trp | Glu | Thr | Leu |
| 65 | | | | | 70 | | | | 75 | | | | | | 80 |
| Ala | Asn | Phe | Tyr | Val | Gly | Asp | Ile | Asp | Glu | Ser | Asp | Arg | Asp | Ile | Lys |
| | | | | 85 | | | | | 90 | | | | | 95 | |
| Asn | Asp | Asp | Phe | Ala | Ala | Glu | Val | Arg | Lys | Leu | Arg | Thr | Leu | Phe | Gln |
| | | | | 100 | | | | | 105 | | | | | 110 | |
| Ser | Leu | Gly | Tyr | Tyr | Asp | Ser | Ser | Lys | Ala | Tyr | Tyr | Ala | Phe | Lys | Val |
| | | 115 | | | | | 120 | | | | | 125 | | | |
| Ser | Phe | Asn | Leu | Cys | Ile | Trp | Gly | Leu | Ser | Thr | Val | Ile | Val | Ala | Lys |
| | 130 | | | | | 135 | | | | | 140 | | | | |
| Trp | Gly | Gln | Thr | Ser | Thr | Leu | Ala | Asn | Val | Leu | Ser | Ala | Ala | Leu | Leu |
| 145 | | | | | 150 | | | | | 155 | | | | | 160 |
| Gly | Leu | Phe | Trp | Gln | Gln | Cys | Gly | Trp | Leu | Ala | His | Asp | Phe | Leu | His |
| | | | | 165 | | | | | 170 | | | | | 175 | |
| His | Gln | Val | Phe | Gln | Asp | Arg | Phe | Trp | Gly | Asp | Leu | Phe | Gly | Ala | Phe |
| | | | 180 | | | | | 185 | | | | | 190 | | |
| Leu | Gly | Gly | Val | Cys | Gln | Gly | Phe | Ser | Ser | Ser | Trp | Trp | Lys | Asp | Lys |
| | | | 195 | | | | | 200 | | | | | 205 | | |
| His | Asn | Thr | His | His | Ala | Ala | Pro | Asn | Val | His | Gly | Glu | Asp | Pro | Asp |
| | 210 | | | | | 215 | | | | | 220 | | | | |
| Ile | Asp | Thr | His | Pro | Leu | Leu | Thr | Trp | Ser | Glu | His | Ala | Leu | Glu | Met |
| 225 | | | | | 230 | | | | | 235 | | | | | 240 |
| Phe | Ser | Asp | Val | Pro | Asp | Glu | Glu | Leu | Thr | Arg | Met | Trp | Ser | Arg | Phe |
| | | | | 245 | | | | | 250 | | | | | 255 | |
| Met | Val | Leu | Asn | Gln | Thr | Trp | Phe | Tyr | Phe | Pro | Ile | Leu | Ser | Phe | Ala |
| | | | 260 | | | | | 265 | | | | | 270 | | |
| Arg | Leu | Ser | Trp | Cys | Leu | Gln | Ser | Ile | Leu | Phe | Val | Leu | Pro | Asn | Gly |
| | | 275 | | | | | 280 | | | | | 285 | | | |
| Gln | Ala | His | Lys | Pro | Ser | Gly | Ala | Arg | Val | Pro | Ile | Ser | Leu | Val | Glu |
| | 290 | | | | | 295 | | | | | 300 | | | | |
| Gln | Leu | Ser | Leu | Ala | Met | His | Trp | Thr | Trp | Tyr | Leu | Ala | Thr | Met | Phe |
| 305 | | | | | 310 | | | | | 315 | | | | | 320 |
| Leu | Phe | Ile | Lys | Asp | Pro | Val | Asn | Met | Leu | Val | Tyr | Phe | Leu | Val | Ser |
| | | | | 325 | | | | | 330 | | | | | 335 | |
| Gln | Ala | Val | Cys | Gly | Asn | Leu | Leu | Ala | Ile | Val | Phe | Ser | Leu | Asn | His |
| | | | 340 | | | | | 345 | | | | | 350 | | |
| Asn | Gly | Met | Pro | Val | Ile | Ser | Lys | Glu | Glu | Ala | Val | Asp | Met | Asp | Phe |
| | | 355 | | | | | 360 | | | | | 365 | | | |
| Phe | Thr | Lys | Gln | Ile | Ile | Thr | Gly | Arg | Asp | Val | His | Pro | Gly | Leu | Phe |
| | 370 | | | | | 375 | | | | | 380 | | | | |
| Ala | Asn | Trp | Phe | Thr | Gly | Gly | Leu | Asn | Tyr | Gln | Ile | Glu | His | His | Leu |
| 385 | | | | | 390 | | | | | 395 | | | | | 400 |

```
Phe Pro Ser Met Pro Arg His Asn Phe Ser Lys Ile Gln Pro Ala Val
            405                 410                 415

Glu Thr Leu Cys Lys Lys Tyr Asn Val Arg Tyr His Thr Thr Gly Met
        420                 425                 430

Ile Glu Gly Thr Ala Glu Val Phe Ser Arg Leu Asn Glu Val Ser Lys
    435                 440                 445

Ala Thr Ser Lys Met Gly Lys Ala Gln
    450                 455

<210> SEQ ID NO 9
<211> LENGTH: 1949
<212> TYPE: DNA
<213> ORGANISM: Artificial Sequence
<220> FEATURE:
<223> OTHER INFORMATION: chimeric TEF::delta 6 desaturase::XPR gene

<400> SEQUENCE: 9
cccaattgcc caattgacc  ccaaattgac ccagtagcgg gcccaacccc ggcgagagcc     60
cccttcaccc cacatatcaa acctccccg  gttcccacac ttgccgttaa gggcgtaggg    120
tactgcagtc tggaatctac gcttgttcag actttgtact agtttctttg tctggccatc    180
cgggtaaccc atgccggacg caaaatagac tactgaaaat ttttttgctt tgtggttggg    240
actttagcca agggtataaa agaccaccgt ccccgaatta cctttcctct tcttttctct    300
ctctccttgt caactcacac ccgaaatcgt taagcatttc cttctgagta taagaatcat    360
tcaccatggc tgccgctccc tctgtgcgaa cctttacccg agccgaggtt ctgaacgctg    420
aggctctgaa cgagggcaag aaggacgctg aggctccctt cctgatgatc atcgacaaca    480
aggtgtacga cgtccgagag ttcgtccctg accatcctgg aggctccgtg attctcaccc    540
acgttggcaa ggacggcacc gacgtctttg acacctttca tcccgaggct gcttgggaga    600
ctctcgccaa cttctacgtt ggagacattg acgagtccga ccgagacatc aagaacgatg    660
actttgccgc tgaggtccga agctgcgaa ccctgttcca gtctctcggc tactacgact    720
cctctaaggc ctactacgcc ttcaaggtct ccttcaacct ctgcatctgg ggactgtcca    780
ccgtcattgt ggccaagtgg ggtcagacct ccaccctcgc caacgtgctc tctgctgccc    840
tgctcggcct gttctggcag cagtgcggat ggctggctca cgactttctg caccaccagg    900
tcttccagga ccgattctgg ggtgatctct cggagccttc ctgggaggt gtctgccagg    960 gcttctcctc ttcctggtgg aaggacaagc acaacactca ccatgccgct cccaacgtgc   1020
atggcgagga tcctgacatt gacacccacc ctctcctgac ctggtccgag cacgctctgg   1080
agatgttctc cgacgtcccc gatgaggagc tgacccgaat gtggtctcga ttcatggtcc   1140
tgaaccagac ctggttctac ttccccattc tctccttcgc tcgactgtct tggtgcctcc   1200
agtccattct ctttgtgctg cccaacggtc aggctcacaa gccctccgga gctcgagtgc   1260
ccatctccct ggtcgagcag ctgtccctcg ccatgcactg gacctggtac ctcgctacca   1320
tgttcctgtt catcaaggat cctgtcaaca tgctcgtgta cttcctggtg tctcaggctg   1380
tgtgcggaaa cctgctcgcc atcgtgttct ccctcaacca caacggtatg cctgtgatct   1440
ccaaggagga ggctgtcgac atggatttct ttaccaagca gatcatcact ggtcgagatg   1500
tccatcctgg actgttcgcc aactggttca cggtggcct gaactaccag atcgagcatc   1560
acctgttccc ttccatgcct cgacacaact tctccaagat ccagcctgcc gtcgagaccc   1620
tgtgcaagaa gtacaacgtc cgataccaca ccactggtat gatcgaggga actgccgagg   1680
```

-continued

```
tcttctcccg actgaacgag gtctccaagg ccacctccaa gatgggcaag gctcagtaag   1740
cggccgccac cgcggcccga gattccggcc tcttcggccg ccaagcgacc cgggtggacg   1800
tctagaggta cctagcaatt aacagatagt tgccggtga  taattctctt aacctcccac   1860
actcctttga cataacgatt tatgtaacga aactgaaatt tgaccagata ttgtgtccgc   1920
ggtggagctc cagcttttgt tcccttttag                                    1949
```

<210> SEQ ID NO 10
<211> LENGTH: 33
<212> TYPE: DNA
<213> ORGANISM: Artificial Sequence
<220> FEATURE:
<223> OTHER INFORMATION: Primer YL238

<400> SEQUENCE: 10

```
taccgaatat acagatctaa caagctacca cca                                33
```

<210> SEQ ID NO 11
<211> LENGTH: 33
<212> TYPE: DNA
<213> ORGANISM: Artificial Sequence
<220> FEATURE:
<223> OTHER INFORMATION: Primer YL239

<400> SEQUENCE: 11

```
tggtggtagc ttgttagatc tgtatattcg gta                                33
```

<210> SEQ ID NO 12
<211> LENGTH: 35
<212> TYPE: DNA
<213> ORGANISM: Artificial Sequence
<220> FEATURE:
<223> OTHER INFORMATION: Primer YL242

<400> SEQUENCE: 12

```
cctttagtga gggtttaaac ttcgagcttg gcgta                              35
```

<210> SEQ ID NO 13
<211> LENGTH: 35
<212> TYPE: DNA
<213> ORGANISM: Artificial Sequence
<220> FEATURE:
<223> OTHER INFORMATION: Primer YL243

<400> SEQUENCE: 13

```
tacgccaagc tcgaagttta accctcact  aaagg                              35
```

<210> SEQ ID NO 14
<211> LENGTH: 34
<212> TYPE: DNA
<213> ORGANISM: Artificial Sequence
<220> FEATURE:
<223> OTHER INFORMATION: Primer YL240

<400> SEQUENCE: 14

```
atgatgtcga ctcagatctg cgacgacgga attc                               34
```

<210> SEQ ID NO 15
<211> LENGTH: 34
<212> TYPE: DNA
<213> ORGANISM: Artificial Sequence
<220> FEATURE:
<223> OTHER INFORMATION: Primer YL241

<400> SEQUENCE: 15

```
gaattccgtc gtcgcagatc tgagtcgaca tcat                                  34

<210> SEQ ID NO 16
<211> LENGTH: 1930
<212> TYPE: DNA
<213> ORGANISM: Artificial Sequence
<220> FEATURE:
<223> OTHER INFORMATION: chimeric TEF::delta 12 desaturase::XPR gene

<400> SEQUENCE: 16
gatctgcgac gacggaattc ctgcagccca tctgcagaat tcaggagaga ccgggttggc      60
ggcgtatttg tgtcccaaaa aacagcccca attgccccaa ttgaccccaa attgacccag     120
tagcgggccc aaccccggcg agagccccct tcaccccaca tatcaaacct cccccggttc     180
ccacacttgc cgttaagggc gtagggtact gcagtctgga atctacgctt gttcagactt     240
tgtactagtt tctttgtctg gccatccggg taacccatgc cggacgcaaa atagactact     300
gaaaattttt ttgctttgtg gttgggactt tagccaaggg tataaaagac caccgtcccc     360
gaattacctt tcctcttctt ttctctctct ccttgtcaac tcacacccga aatcgttaag     420
catttccttc tgagtataag aatcattcac catggattcg accacgcaga ccaacaccgg     480
caccggcaag gtggccgtgc agcccccac ggccttcatt aagcccattg agaaggtgtc     540
cgagcccgtc tacgacacct ttggcaacga gttcactcct ccagactact ctatcaagga     600
tattctggat gccattcccc aggagtgcta caagcggtcc tacgttaagt cctactcgta     660
cgtggcccga gactgcttct ttatcgccgt ttttgcctac atggcctacg cgtacctgcc     720
tcttattccc tcggcttccg gccgagctgt ggcctgggcc atgtactcca ttgtccaggg     780
tctgtttggc accggtctgt ggttcttgc ccacgagtgt ggccactctg ctttctccga     840
ctctaacacc gtcaacaacg tcaccggatg ggttctgcac tcctccatgc tggtcccctta     900 ctacgcctgg aagctgaccc actccatgca ccacaagtcc actggtcacc tcacccgtga     960
tatggtgttt gtgcccaagg accgaaagga gtttatggag aaccgaggcg cccatgactg    1020
gtctgagctt gctgaggacg ctcccctcat gaccctctac ggcctcatca cccagcaggt    1080
gtttggatgg cctctgtatc tgctgtctta cgttaccgga cagaagtacc ccaagctcaa    1140
caaatgggct gtcaaccact tcaaccccaa cgccccgctg tttgagaaga aggactggtt    1200
caacatctgg atctctaacg tcggtattgg tatcaccatg tccgtcatcg catactccat    1260
caaccgatgg ggcctggctt ccgtcacct tactacctg atcccctacc tgtgggtcaa    1320
ccactggctc gtggccatca cctacctgca gcacaccgac cccactctgc cccactacca    1380
cgccgaccag tggaacttca cccgaggagc cgccgccacc atcgaccgag agtttggctt    1440
catcggctcc ttctgcttcc atgacatcat cgagacccac gttctgcacc actacgtgtc    1500
tcgaattccc ttctacaacg cccgaatcgc cactgagaag atcaagaagg tcatgggcaa    1560
gcactaccga cacgacgaca ccaacttcat caagtctctt tacactgtcg cccgaacctg    1620
ccagtttgtt gaaggtaagg aaggcattca gatgtttaga acgtcaatg gagtcggagt    1680 tgctcctgac ggcctgcctt ctaaaaagta ggcggccgcc accgcggccc gagattccgg    1740
cctcttcggc cgccaagcga cccgggtgga cgtctagagg tacctagcaa ttaacagata    1800
gtttgccggt gataattctc ttaacctccc acactccttt gacataacga tttatgtaac    1860
gaaactgaaa tttgaccaga tattgtgtcc gcggtggagc tccagctttt gttcccttta    1920
gtgagggttt                                                           1930
```

<210> SEQ ID NO 17
<211> LENGTH: 9541
<212> TYPE: DNA
<213> ORGANISM: Artificial Sequence
<220> FEATURE:
<223> OTHER INFORMATION: Plasmid pDMW208

<400> SEQUENCE: 17

```
aaaccctcac taaagggaac aaaagctgga gctccaccgc ggacacaata tctggtcaaa      60
tttcagtttc gttacataaa tcgttatgtc aaaggagtgt gggaggttaa gagaattatc     120
accggcaaac tatctgttaa ttgctaggta cctctagacg tccacccggg tcgcttggcg     180
gccgaagagg ccggaatctc gggccgcggt ggcggccgcc tacttttag aaggcaggcc      240 gtcaggagca actccgactc cattgacgtt tctaaacatc tgaatgcctt ccttaccttc     300
aacaaactgg caggttcggg cgacagtgta agagacttg atgaagttgg tgtcgtcgtg      360
tcggtagtgc ttgcccatga ccttcttgat cttctcagtg gcgattcggg cgttgtagaa     420
gggaattcga gacacgtagt ggtgcagaac gtgggtctcg atgatgtcat ggaagcagaa     480
ggagccgatg aagccaaact ctcggtcgat ggtggcggcg gctcctcggg tgaagttcca     540
ctggtcggcg tggtagtggg gcagagtggg gtcggtgtgc tgcaggtagg tgatggccac     600
gagccagtgg ttgacccaca ggtaggggat caggtagtag agggtgacgg aagccaggcc     660
ccatcggttg atggagtatg cgatgacgga catggtgata ccaataccga cgttagagat     720
ccagatgttg aaccagtcct tcttctcaaa cagcggggcg ttggggttga agtggttgac     780
agcccatttg ttgagcttgg ggtacttctg tccggtaacg taagacagca gatacagagg     840
ccatccaaac acctgctggg tgatgaggcc gtagagggtc atgaggggag cgtcctcagc     900
aagctcagac cagtcatggg cgcctcggtt ctccataaac tcctttcggt ccttgggcac     960
aaacaccata tcacgggtga ggtgaccagt ggacttgtgg tgcatggagt gggtcagctt    1020
ccaggcgtag taagggacca gcatggagga gtgcagaacc catccggtga cgttgttgac    1080
ggtgttagag tcgagaaaag cagagtggcc acactcgtgg gcaagaaccc acagaccggt    1140
gccaaacaga ccctggacaa tggagtacat ggcccaggcc acagctcggc cggaagccga    1200
gggaataaga ggcaggtacg cgtaggccat gtaggcaaaa acggcgataa agaagcagtc    1260
tcgggccacg tacgagtagg acttaacgta ggaccgcttg tagcactcct ggggaatggc    1320
atccagaata tccttgatag agtagtctga aggagtgaac tcgttgccaa aggtgtcgta    1380
gacgggctcg gacaccttct caatgggctt aatgaaggcc gtgggggct gcacggccac     1440 cttgccggtg ccggtgttgg tctgcgtggt cgaatccatg gtgaatgatt cttatactca    1500
gaaggaaatg cttaacgatt tcgggtgtga gttgacaagg agagagagaa aagaagagga    1560
aaggtaattc ggggacggtg gtcttttata cccttggcta aagtcccaac cacaaagcaa    1620
aaaaattttc agtagtctat tttgcgtccg gcatgggtta cccggatggc cagacaaaga    1680
aactagtaca aagtctgaac aagcgtagat tccagactgc agtaccctac gcccttaacg    1740
gcaagtgtgg gaaccggggg aggtttgata tgtgggtga aggggctct cgccggggtt      1800 gggcccgcta ctgggtcaat ttggggtcaa ttggggcaat tggggctgtt ttttgggaca    1860
caaatacgcc gccaacccgg tctctcctga attctgcaga tgggctgcag gaattccgtc    1920
gtcgcagatc taacaagcta ccaccacact cgttgggtgc agtcgccagc ttaaagatat    1980
ctatccacat cagccacaac tcccttcctt taataaaccg actacaccct ggctattga     2040 ggttatgagt gaatatactg tagacaagac actttcaaga agactgtttc caaaacgtac    2100
```

```
cactgtcctc cactacaaac acacccaatc tgcttcttct agtcaaggtt gctacaccgg    2160
taaattataa atcatcattt cattagcagg gcagggccct ttttatagag tcttatacac    2220
tagcggaccc tgccggtaga ccaacccgca ggcgcgtcag tttgctcctt ccatcaatgc    2280
gtcgtagaaa cgacttactc cttcttgagc agctccttga ccttgttggc aacaagtctc    2340
cgacctcgga ggtggaggaa gagcctccga tatcggcggt agtgatacca gcctcgacgg    2400
actccttgac ggcagcctca acagcgtcac cggcgggctt catgttaaga gagaacttga    2460
gcatcatggc ggcagacaga atggtggcaa tggggttgac cttctgcttg ccgagatcgg    2520
gggcagatcc gtgacagggc tcgtacagac cgaacgcctc gttggtgtcg ggcagagaag    2580
ccagagaggc ggagggcagc agacccagag aaccggggat gacggaggcc tcgtcggaga    2640
tgatatcgcc aaacatgttg gtggtgatga tgataccatt catcttggag ggctgcttga    2700
tgaggatcat ggcggccgag tcgatcagct ggtggttgag ctcgagctgg gggaattcgt    2760
ccttgaggac tcgagtgaca gtctttcgcc aaagtcgaga ggaggccagc acgttggcct    2820
tgtcaagaga ccacacggga agaggggggt tgtgctgaag ggccaggaag gcggccattc    2880
gggcaattcg ctcaacctca ggaacggagt aggtctcggt gtcggaagcg acgccagatc    2940
cgtcatcctc ctttcgctct ccaaagtaga tacctccgac gagctctcgg acaatgatga    3000
agtcggtgcc ctcaacgttt cggatggggg agagatcggc gagcttgggc gacagcagct    3060
ggcagggtcg caggttggcg tacaggttca ggtcctttcg cagcttgagg agaccctgct    3120
cgggtcgcac gtcggttcgt ccgtcgggag tggtccatac ggtgttggca cgcgcctccga    3180 cagcaccgag cataatagag tcagcctttc ggcagatgtc gagagtagcg tcggtgatgg    3240
gctcgccctc cttctcaatg gcagctcctc caatgagtcg gtcctcaaac acaaactcgg    3300
tgccggaggc ctcagcaaca gacttgagca ccttgacggc ctcggcaatc acctcggggc    3360
cacagaagtc gccgccgaga agaacaatct tcttggagtc agtcttggtc ttcttagttt    3420
cgggttccat tgtggatgtg tgtggttgta tgtgtgatgt ggtgtgtgga gtgaaaatct    3480
gtggctggca aacgctcttg tatatatacg cacttttgcc cgtgctatgt ggaagactaa    3540
acctccgaag attgtgactc aggtagtgcg gtatcggcta gggacccaaa ccttgtcgat    3600
gccgatagcg ctatcgaacg taccccagcc ggccgggagt atgtcggagg ggacatacga    3660
gatcgtcaag ggtttgtggc caactggtaa ataaatgatg tcgactcagg cgacgacgga    3720
attcctgcag cccatctgca gaattcagga gagaccgggt tggcggcgta tttgtgtccc    3780
aaaaaacagc cccaattgcc ccaattgacc ccaaattgac ccagtagcgg gcccaacccc    3840
ggcgagagcc cccttcaccc cacatatcaa acctcccccg gttcccacac ttgccgttaa    3900
gggcgtaggg tactgcagtc tggaatctac gcttgttcag actttgtact agtttctttg    3960
tctggccatc cgggtaaccc atgccggacg caaaatagac tactgaaaat ttttttgctt    4020
tgtggttggg actttagcca agggtataaa agaccaccgt ccccgaatta cctttcctct    4080
tcttttctct ctctccttgt caactcacac ccgaaatcgt taagcatttc cttctgagta    4140
taagaatcat tcaccatggc tgccgctccc tctgtgcgaa cctttacccg agccgaggtt    4200
ctgaacgctg aggctctgaa cgagggcaag aaggacgctg aggctcccct cctgatgatc    4260
atcgacaaca aggtgtacga cgtccgagag ttcgtccctg accatcctgg aggctccgtg    4320
attctcaccc acgttggcaa ggacggcacc gacgtctttg acaccttcca tcccgaggct    4380
gcttgggaga ctctcgccaa cttctacgtt ggagacattg acgagtccga ccgagacatc    4440
```

```
aagaacgatg actttgccgc tgaggtccga aagctgcgaa ccctgttcca gtctctcggc    4500
tactacgact cctctaaggc ctactacgcc ttcaaggtct ccttcaacct ctgcatctgg    4560
ggactgtcca ccgtcattgt ggccaagtgg ggtcagacct ccaccctcgc caacgtgctc    4620
tctgctgccc tgctcggcct gttctggcag cagtgcggat ggctggctca cgactttctg    4680
caccaccagg tcttccagga ccgattctgg ggtgatctct tcggagcctt cctgggaggt    4740
gtctgccagg gcttctcctc ttcctggtgg aaggacaagc acaacactca ccatgccgct    4800
cccaacgtgc atggcgagga tcctgacatt gacacccacc ctctcctgac ctggtccgag    4860
cacgctctgg agatgttctc cgacgtcccc gatgaggagc tgacccgaat gtggtctcga    4920
ttcatggtcc tgaaccagac ctggttctac ttccccattc tctccttcgc tcgactgtct    4980
tggtgcctcc agtccattct ctttgtgctg cccaacggtc aggctcacaa gccctccgga    5040
gctcgagtgc ccatctccct ggtcgagcag ctgtccctcg ccatgcactg gacctggtac    5100
ctcgctacca tgttcctgtt catcaaggat cctgtcaaca tgctcgtgta cttcctggtg    5160
tctcaggctg tgtgcggaaa cctgctcgcc atcgtgttct ccctcaacca caacggtatg    5220
cctgtgatct ccaaggagga ggctgtcgac atggatttct ttaccaagca gatcatcact    5280
ggtcgagatg tccatcctgg actgttcgcc aactggttca ccggtggcct gaactaccag    5340
atcgagcatc acctgttccc ttccatgcct cgacacaact tctccaagat ccagcctgcc    5400
gtcgagaccc tgtgcaagaa gtacaacgtc cgataccaca ccactggtat gatcgaggga    5460
actgccgagg tcttctcccg actgaacgag gtctccaagg ccacctccaa gatgggcaag    5520
gctcagtaag cggccgccac cgcggcccga gattccggcc tcttcggccg ccaagcgacc    5580
cgggtggacg tctagaggta cctagcaatt aacagatagt ttgccggtga taattctctt    5640
aacctcccac actcctttga cataacgatt tatgtaacga aactgaaatt tgaccagata    5700
ttgtgtccgc ggtggagctc cagcttttgt tccctttagt gagggttaat ttcgagcttg    5760
gcgtaatcat ggtcatagct gtttcctgtg tgaaattgtt atccgctcac aagcttccac    5820
acaacgtacg gaccacctcc cttgcacttc ttggtatatc agtataggct gatgtattca    5880
tagtggggtt tttcataata aatttactaa cggcaggcaa cattcactcg gcttaaacgc    5940
aaaacggacc gtcttgatat cttctgacgc attgaccacc gagaaatagt gttagttacc    6000
gggtgagtta ttgttcttct acacagcgac gcccatcgtc tagagttgat gtactaactc    6060
agatttcact acctacccta tccctggtac gcacaggcgc gccagctgca ttaatgaatc    6120
ggccaacgcg cggggagagg cggtttgcgt attgggcgct cttccgcttc ctcgctcact    6180
gactcgctgc gctcggtcgt tcggctgcgg cgagcggtat cagctcactc aaaggcggta    6240
atacggttat ccacagaatc aggggataac gcaggaaaga acatgtgagc aaaaggccag    6300
caaaaggcca ggaaccgtaa aaaggccgcg ttgctggcgt ttttccatag gctccgcccc    6360
cctgacgagc atcacaaaaa tcgacgctca agtcagaggt ggcgaaaccc gacaggacta    6420
taaagatacc aggcgtttcc ccctggaagc tccctcgtgc gctctcctgt tccgaccctg    6480
ccgcttaccg gatacctgtc cgcctttctc ccttcgggaa gcgtggcgct ttctcatagc    6540
tcacgctgta ggtatctcag ttcggtgtag tcgttcgct ccaagctggg ctgtgtgcac    6600 gaacccccg ttcagcccga ccgctgcgcc ttatccggta actatcgtct tgagtccaac    6660
ccggtaagac acgacttatc gccactggca gcagccactg gtaacaggat tagcagagcg    6720
aggtatgtag gcggtgctac agagttcttg aagtggtggc ctaactacgg ctacactaga    6780
agaacagtat ttggtatctg cgctctgctg aagccagtta ccttcggaaa aagagttggt    6840
```

```
agctcttgat ccggcaaaca aaccaccgct ggtagcggtg gttttttttgt ttgcaagcag    6900 cagattacgc gcagaaaaaa aggatctcaa aagatccctt tgatcttttc tacggggtct    6960
gacgctcagt ggaacgaaaa ctcacgttaa gggattttgg tcatgagatt atcaaaaagg    7020
atcttcacct agatcctttt aaattaaaaa tgaagtttta atcaatcta aagtatatat    7080 gagtaaactt ggtctgacag ttaccaatgc ttaatcagtg aggcacctat ctcagcgatc    7140
tgtctatttc gttcatccat agttgcctga ctccccgtcg tgtagataac tacgatacgg    7200
gagggcttac catctggccc cagtgctgca atgataccgc gagacccacg ctcaccggct    7260
ccagatttat cagcaataaa ccagccagcc ggaagggccg agcgcagaag tggtcctgca    7320
actttatccg cctccatcca gtctattaat tgttgccggg aagctagagt aagtagttcg    7380
ccagttaata gtttgcgcaa cgttgttgcc attgctacag gcatcgtggt gtcacgctcg    7440
tcgtttggta tggcttcatt cagctccggt tcccaacgat caaggcgagt tacatgatcc    7500
cccatgttgt gcaaaaaagc ggttagctcc ttcggtcctc cgatcgttgt cagaagtaag    7560
ttggccgcag tgttatcact catggttatg gcagcactgc ataattctct tactgtcatg    7620
ccatccgtaa gatgcttttc tgtgactggt gagtactcaa ccaagtcatt ctgagaatag    7680
tgtatgcggc gaccgagttg ctcttgcccg gcgtcaatac gggataatac cgcgccacat    7740
agcagaactt taaaagtgct catcattgga aaacgttctt cggggcgaaa actctcaagg    7800
atcttaccgc tgttgagatc cagttcgatg taacccactc gtgcacccaa ctgatcttca    7860
gcatctttta ctttcaccag cgtttctggg tgagcaaaaa caggaaggca aaatgccgca    7920
aaaaagggaa taagggcgac acggaaatgt tgaatactca tactcttcct ttttcaatat    7980
tattgaagca tttatcaggg ttattgtctc atgagcggat acatatttga atgtatttag    8040
aaaaataaac aaataggggt tccgcgcaca tttccccgaa aagtgccacc tgatgcggtg    8100
tgaaataccg cacagatgcg taaggagaaa ataccgcatc aggaaattgt aagcgttaat    8160
attttgttaa aattcgcgtt aaattttgt taaatcagct cattttttaa ccaataggcc    8220
gaaatcggca aaatccctta taaatcaaaa gaatagaccg agatagggtt gagtgttgtt    8280
ccagtttgga acaagagtcc actattaaag aacgtggact ccaacgtcaa agggcgaaaa    8340
accgtctatc agggcgatgg cccactacgt gaaccatcac cctaatcaag ttttttgggg    8400
tcgaggtgcc gtaaagcact aaatcggaac cctaaaggga gcccccgatt tagagcttga    8460
cggggaaagc cggcgaacgt ggcgagaaag gaagggaaga agcgaaagg agcgggcgct    8520 agggcgctgg caagtgtagc ggtcacgctg cgcgtaacca ccacacccgc cgcgcttaat    8580
gcgccgctac agggcgcgtc cattcgccat tcaggctgcg caactgttgg gaagggcgat    8640
cggtgcgggc ctcttcgcta ttacgccagc tggcgaaagg gggatgtgct gcaaggcgat    8700
taagttgggt aacgccaggg ttttcccagt cacgacgttg taaaacgacg gccagtgaat    8760
tgtaatacga ctcactatag gcgaattgg gcccgacgtc gcatgctgtg taacactcgc    8820
tctggagagt tagtcatccg acagggtaac tctaatctcc caacacctta ttaactctgc    8880
gtaactgtaa ctcttcttgc cacgtcgatc ttactcaatt ttcctgctca tcatctgctg    8940
gattgttgtc tatcgtctgg ctctaataca tttattgttt attgcccaaa caactttcat    9000
tgcacgtaag tgaattgttt tataacagcg ttcgccaaat tgctgcgcca tcgtcgtccg    9060
gctgtcctac cgttagggt agtgtgtctc acactaccga ggttactaga gttgggaaag    9120
cgatactgcc tcggacacac cacctgggtc ttacgactgc agagagaatc ggcgttaatt    9180
```

```
aatttgaatc gaatcgatga gcctaaaatg aacccgagta tatctcataa aattctcggt      9240
gagaggtctg tgactgtcag tacaaggtgc cttcattatg ccctcaacct taccatacct      9300
cactgaatgt agtgtacctc taaaaatgaa atacagtgcc aaaagccaag gcactgagct      9360
cgtctaacgg acttgatata caaccaatta aaacaaatga aaagaaatac agttctttgt      9420
atcatttgta acaattaccc tgtacaaact aaggtattga aatcccacaa tattcccaaa      9480
gtccacccct ttccaaattg tcatgcctac aactcatata ccaagcacta acctaccgtt      9540
t                                                                      9541

<210> SEQ ID NO 18
<211> LENGTH: 28
<212> TYPE: DNA
<213> ORGANISM: Artificial Sequence
<220> FEATURE:
<223> OTHER INFORMATION: Primer YL253

<400> SEQUENCE: 18
tttccatggt ccaggggcaa aaggccga                                           28

<210> SEQ ID NO 19
<211> LENGTH: 31
<212> TYPE: DNA
<213> ORGANISM: Artificial Sequence
<220> FEATURE:
<223> OTHER INFORMATION: Primer YL254

<400> SEQUENCE: 19
tttgcggccg cttacatggc gggaaactcc t                                       31

<210> SEQ ID NO 20
<211> LENGTH: 35
<212> TYPE: DNA
<213> ORGANISM: Artificial Sequence
<220> FEATURE:
<223> OTHER INFORMATION: Primer YL293

<400> SEQUENCE: 20
tttgcggccg catgtacata caagattatt tatag                                   35

<210> SEQ ID NO 21
<211> LENGTH: 40
<212> TYPE: DNA
<213> ORGANISM: Artificial Sequence
<220> FEATURE:
<223> OTHER INFORMATION: Primer YL317

<400> SEQUENCE: 21
tttcgtacga tcgatcccta actgtatact agcattctga                              40

<210> SEQ ID NO 22
<211> LENGTH: 2179
<212> TYPE: DNA
<213> ORGANISM: Artificial Sequence
<220> FEATURE:
<223> OTHER INFORMATION: chimeric TEF::delta 6 desaturase::OCT gene

<400> SEQUENCE: 22
gacggaattc ctgcagccca tctgcagaat tcaggagaga ccgggttggc ggcgtatttg        60
tgtcccaaaa aacagcccca attgccccaa ttgaccccaa attgacccag tagcgggccc       120
aaccccggcg agagcccccct tcaccccaca tatcaaacct cccccggttc ccacacttgc      180
cgttaagggc gtagggtact gcagtctgga atctacgctt gttcagactt tgtactagtt       240
```

```
tctttgtctg gccatccggg taacccatgc cggacgcaaa atagactact gaaaatttt      300
ttgctttgtg gttgggactt tagccaaggg tataaaagac caccgtcccc gaattacctt    360
tcctcttctt ttctctctct ccttgtcaac tcacacccga atcgttaag catttccttc     420
tgagtataag aatcattcac catggtccag ggcaaaagg ccgagaagat ctcgtgggcg     480
accatccgtg agcacaaccg ccaagacaac gcgtggatcg tgatccacca caaggtgtac   540
gacatctcgg cctttgagga ccacccgggc ggcgtcgtca tgttcacgca ggccggcgaa   600
gacgcgaccg atgcgttcgc tgtcttccac ccgagctcgg cgctcaagct cctcgagcag   660
tactacgtcg gcgacgtcga ccagtcgacg gcggccgtcg acacgtcgat ctcggacgag   720
gtcaagaaga gccagtcgga cttcattgcg tcgtaccgca agctgcgcct tgaagtcaag   780
cgcctcggct tgtacgactc gagcaagctc tactacctct acaagtgcgc ctcgacgctg   840
agcattgcgc ttgtgtcggc ggccatttgc ctccactttg actcgacggc catgtacatg   900
gtcgcggctg tcatccttgg cctctttac cagcagtgcg gctggctcgc ccatgacttt   960
ctgcaccacc aagtgtttga gaaccacttg tttggcgacc tcgtcggcgt catggtcggc 1020
aacctctggc agggcttctc ggtgcagtgg tggaagaaca agcacaacac gcaccatgcg 1080
atccccaacc tccacgcgac gcccgagatc gccttccacg cgacccgga cattgacacg  1140
atgccgattc tcgcgtggtc gctcaagatg gcgcagcacg cggtcgactc gcccgtcggg 1200
ctcttcttca tgcgctacca agcgtacctg tactttccca tcttgctctt tgcgcgtatc 1260
tcgtgggtga tccagtcggc catgtacgcc ttctacaact tgggcccgg cggcaccttt  1320
gacaaggtcc agtacccgct gctcgagcgc gccggcctcc tcctctacta cggctggaac 1380
ctcggccttg tgtacgcagc caacatgtcg ctgctccaag cggctgcgtt cctctttgtg 1440
agccaggcgt cgtgcggcct cttcctcgcg atggtcttta gcgtcggcca aacggcatg  1500
gaggtctttg acaaggacag caagcccgat ttttggaagc tgcaagtgct ctcgacgcgc 1560
aacgtgacgt cgtcgctctg gatcgactgg ttcatgggcg gcctcaacta ccagatcgac 1620
caccacttgt tcccgatggt gccccggcac aacctcccgg cgctcaacgt gctcgtcaag 1680
tcgctctgca gcagtacga catcccatac cacgagacgg gcttcatcgc gggcatggcc 1740
gaggtcgtcg tgcacctcga gcgcatctcg atcgagttct tcaaggagtt ccccgccatg 1800
taagcggccg catgtacata caagattatt tatagaaatg aatcgcgatc gaacaaagag 1860
tacgagtgta cgagtagggg atgatgataa aagtggaaga agttccgcat ctttggattt 1920
atcaacgtgt aggacgatac ttcctgtaaa aatgcaatgt ctttaccata ggttctgctg 1980
tagatgttat taactaccat taacatgtct acttgtacag ttgcagacca gttggagtat 2040
agaatggtac acttaccaaa aagtgttgat ggttgtaact acgatatata aaactgttga 2100
cgggatcccc gctgatatgc ctaaggaaca atcaaagagg aagatattaa ttcagaatgc 2160
tagtatacag ttagggatc                                                2179
```

<210> SEQ ID NO 23
<211> LENGTH: 32
<212> TYPE: DNA
<213> ORGANISM: Artificial Sequence
<220> FEATURE:
<223> OTHER INFORMATION: Primer YL226

<400> SEQUENCE: 23

```
tgtggccaac tggtatttaa atgatgtcga cg                                    32
```

<210> SEQ ID NO 24
<211> LENGTH: 32
<212> TYPE: DNA
<213> ORGANISM: Artificial Sequence
<220> FEATURE:
<223> OTHER INFORMATION: Primer YL227

<400> SEQUENCE: 24
cgtcgacatc atttaaatac cagttggcca ca                              32

<210> SEQ ID NO 25
<211> LENGTH: 33
<212> TYPE: DNA
<213> ORGANISM: Artificial Sequence
<220> FEATURE:
<223> OTHER INFORMATION: Primer YL61

<400> SEQUENCE: 25
acaattccac acaacgtacg agccggaagc ata                             33

<210> SEQ ID NO 26
<211> LENGTH: 33
<212> TYPE: DNA
<213> ORGANISM: Artificial Sequence
<220> FEATURE:
<223> OTHER INFORMATION: Primer YL62

<400> SEQUENCE: 26
tatgcttccg gctcgtacgt tgtgtggaat tgt                             33

<210> SEQ ID NO 27
<211> LENGTH: 31
<212> TYPE: DNA
<213> ORGANISM: Artificial Sequence
<220> FEATURE:
<223> OTHER INFORMATION: Primer YL230

<400> SEQUENCE: 27
aaccttgcgg atatccatac gccgcggcgg a                               31

<210> SEQ ID NO 28
<211> LENGTH: 31
<212> TYPE: DNA
<213> ORGANISM: Artificial Sequence
<220> FEATURE:
<223> OTHER INFORMATION: Primer YL231

<400> SEQUENCE: 28
tccgccgcgg cgtatggata tccgcaaggt t                               31

<210> SEQ ID NO 29
<211> LENGTH: 31
<212> TYPE: DNA
<213> ORGANISM: Artificial Sequence
<220> FEATURE:
<223> OTHER INFORMATION: Primer YL228

<400> SEQUENCE: 29
ggagggcaat ggcgctatgg aaccttgcgg a                               31

<210> SEQ ID NO 30
<211> LENGTH: 31
<212> TYPE: DNA
<213> ORGANISM: Artificial Sequence
<220> FEATURE:
<223> OTHER INFORMATION: Primer YL229

```
<400> SEQUENCE: 30
tccgcaaggt tccatagcgc cattgccctc c                              31

<210> SEQ ID NO 31
<211> LENGTH: 23
<212> TYPE: DNA
<213> ORGANISM: Artificial Sequence
<220> FEATURE:
<223> OTHER INFORMATION: Primer YL179

<400> SEQUENCE: 31
tttccatggc aaacagcagc gtg                                       23

<210> SEQ ID NO 32
<211> LENGTH: 35
<212> TYPE: DNA
<213> ORGANISM: Artificial Sequence
<220> FEATURE:
<223> OTHER INFORMATION: Primer YL179A

<400> SEQUENCE: 32
tttgcggccg cttaagatag ctctgcacaa aaaag                          35

<210> SEQ ID NO 33
<211> LENGTH: 33
<212> TYPE: DNA
<213> ORGANISM: Artificial Sequence
<220> FEATURE:
<223> OTHER INFORMATION: Primer YL77

<400> SEQUENCE: 33
tagtgagggt taattaatcg agcttggcgt aat                            33

<210> SEQ ID NO 34
<211> LENGTH: 33
<212> TYPE: DNA
<213> ORGANISM: Artificial Sequence
<220> FEATURE:
<223> OTHER INFORMATION: Primer YL78

<400> SEQUENCE: 34
attacgccaa gctcgattaa ttaaccctca cta                            33

<210> SEQ ID NO 35
<211> LENGTH: 32
<212> TYPE: DNA
<213> ORGANISM: Artificial Sequence
<220> FEATURE:
<223> OTHER INFORMATION: Primer YL322

<400> SEQUENCE: 35 aaagggtgc ttggatcgat ggaagccggt ag                              32

<210> SEQ ID NO 36
<211> LENGTH: 32
<212> TYPE: DNA
<213> ORGANISM: Artificial Sequence
<220> FEATURE:
<223> OTHER INFORMATION: Primer YL323

<400> SEQUENCE: 36
ctaccggctt ccatcgatcc aagcacccct tt                             32

<210> SEQ ID NO 37
```

```
<211> LENGTH: 32
<212> TYPE: DNA
<213> ORGANISM: Artificial Sequence
<220> FEATURE:
<223> OTHER INFORMATION: Primer YL325

<400> SEQUENCE: 37
tttgcggccg catggagcgt gttgttctgag tc                                        32

<210> SEQ ID NO 38
<211> LENGTH: 46
<212> TYPE: DNA
<213> ORGANISM: Artificial Sequence
<220> FEATURE:
<223> OTHER INFORMATION: Primer YL326

<400> SEQUENCE: 38
cccttaatta actcacctgc aggattgaga ctatgaatgg attccc                          46

<210> SEQ ID NO 39
<211> LENGTH: 2586
<212> TYPE: DNA
<213> ORGANISM: Artificial Sequence
<220> FEATURE:
<223> OTHER INFORMATION: chimeric GPD::delta 12 desaturase::Aco gene

<400> SEQUENCE: 39
cgatggaagc cggtagaacc gggctgcttg tgcttggaga tggaagccgg tagaaccggg           60
ctgcttgggg ggatttgggg ccgctgggct ccaaagaggg gtaggcattt cgttggggtt          120
acgtaattgc ggcatttggg tcctgcgcgc atgtcccatt ggtcagaatt agtccggata          180
ggagacttat cagccaatca cagcgccgga tccacctgta ggttgggttg ggtgggagca          240
ccctccaca gagtagagtc aaacagcagc agcaacatga tagttggggg tgtgcgtgtt           300
aaaggaaaaa aagaagcttg ggttatatt cccgctctat ttagaggttg cgggatagac           360
gccgacggag ggcaatggcg ctatggaacc ttgcggatat ccatacgccg cggcggactg          420
cgtccgaacc agctccagca gcgttttttc cgggccattg agccgactgc gaccccgcca          480
acgtgtcttg gcccacgcac tcatgtcatg ttggtgttgg gaggccactt tttaagtagc          540
acaaggcacc tagctcgcag caaggtgtcc gaaccaaaga agcggctgca gtggtgcaaa          600
cggggcggaa acggcgggaa aaagccacgg gggcacgaat tgaggcacgc cctcgaattt          660
gagacgagtc acggcccccat tcgcccgcgc aatggctcgc caacgcccgg tcttttgcac         720
cacatcaggt taccccaagc caaacctttg tgttaaaaag cttaacatat tataccgaac          780
gtaggtttgg gcgggcttgc tccgtctgtc caaggcaaca tttatataag ggtctgcatc          840
gccggctcaa ttgaatcttt tttcttcttc tcttctctat attcattctt gaattaaaca          900
cacatcaacc atggattcga ccacgcagac caacaccggc accggcaagg tggccgtgca          960
gccccccacg gccttcatta agcccattga aaggtgtcc gagcccgtct acgacacctt         1020
tggcaacgag ttcactcctc agactactc tatcaaggat attctggatg ccattccca          1080
ggagtgctac aagcggtcct acgttaagtc ctactcgtac gtggcccgag actgcttct          1140
tatcgccgtt tttgcctaca tggcctacgc gtacctgcct cttattccct cggcttccgg          1200
ccgagctgtg gcctgggcca tgtactccat tgtccagggt ctgtttggca ccggtctgtg         1260
ggttcttgcc cacgagtgtg gccactctgc tttctccgac tctaacaccg tcaacaacgt         1320
caccggatgg gttctgcact cctccatgct ggtccttac tacgcctgga agctgaccca         1380
ctccatgcac cacaagtcca ctggtcacct cacccgtgat atggtgtttg tgcccaagga         1440
```

```
ccgaaaggag tttatggaga accgaggcgc ccatgactgg tctgagcttg ctgaggacgc   1500 tccctcatg acctctacg gcctcatcac ccagcaggtg tttggatggc ctctgtatct    1560
gctgtcttac gttaccggac agaagtaccc caagctcaac aaatgggctg tcaaccactt   1620
caaccccaac gccccgctgt tgagaagaa ggactggttc aacatctgga tctctaacgt    1680
cggtattggt atcaccatgt ccgtcatcgc atactccatc aaccgatggg gcctggcttc   1740
cgtcaccctc tactacctga tcccctacct gtgggtcaac cactggctcg tggccatcac   1800
ctacctgcag cacaccgacc ccactctgcc ccactaccac gccgaccagt ggaacttcac   1860
ccgaggagcc gccgccacca tcgaccgaga gtttggcttc atcggctcct tctgcttcca   1920
tgacatcatc gagacccacg ttctgcacca ctacgtgtct cgaattccct tctacaacgc   1980
ccgaatcgcc actgagaaga tcaagaaggt catgggcaag cactaccgac acgacgacac   2040
caacttcatc aagtctcttt acactgtcgc ccgaacctgc cagtttgttg aaggtaagga   2100
aggcattcag atgtttagaa acgtcaatgg agtcggagtt gctcctgacg gcctgccttc   2160
taaaaagtag gcggccgcat ggagcgtgtg ttctgagtcg atgttttcta tggagttgtg   2220
agtgttagta gacatgatgg gtttatatat gatgaatgaa tagatgtgat tttgatttgc   2280
acgatggaat tgagaacttt gtaaacgtac atgggaatgt atgaatgtgg gggttttgtg   2340
actggataac tgacggtcag tggacgccgt tgttcaaata tccaagagat gcgagaaact   2400
ttgggtcaag tgaacatgtc ctctctgttc aagtaaacca tcaactatgg gtagtatatt   2460
tagtaaggac aagagttgag attctttgga gtcctagaaa cgtattttcg cgttccaaga   2520
tcaaattagt agagtaatac gggcacggga atccattcat agtctcaatc ctgcaggtga   2580
gttaat                                                              2586
```

<210> SEQ ID NO 40
<211> LENGTH: 13945
<212> TYPE: DNA
<213> ORGANISM: Artificial Sequence
<220> FEATURE:
<223> OTHER INFORMATION: Plasmid pDMW208D62

<400> SEQUENCE: 40

```
aaaccctcac taagggaac aaaagctgga gctccaccgc ggacacaata tctggtcaaa     60
tttcagtttc gttacataaa tcgttatgtc aaaggagtgt gggaggttaa gagaattatc   120
accggcaaac tatctgttaa ttgctaggta cctctagacg tccacccggg tcgcttggcg   180
gccgaagagg ccggaatctc gggccgcggt ggcggccgcc tacttttag aaggcaggcc    240 gtcaggagca actccgactc cattgacgtt tctaaacatc tgaatgcctt ccttaccttc   300
aacaaactgg caggttcggg cgacagtgta aagagacttg atgaagttgg tgtcgtcgtg   360
tcggtagtgc ttgcccatga ccttcttgat cttctcagtg gcgattcggg cgttgtagaa   420
gggaattcga gacacgtagt ggtgcagaac gtgggtctcg atgatgtcat ggaagcagaa   480
ggagccgatg aagccaaact ctcggtcgat ggtggcggcg gctcctcggg tgaagttcca   540
ctggtcggcg tggtagtggg gcagagtggg gtcggtgtgc tgcaggtagg tgatggccac   600
gagccagtgg ttgacccaca ggtagggaat caggtagtag agggtgacgg aagccaggcc   660
ccatcggttg atggagtatg cgatgacgga catggtgata ccaataccga cgttagagat   720
ccagatgttg aaccagtcct tcttctcaaa cagcggggcg ttggggttga agtggttgac   780
agcccatttg ttgagcttgg ggtacttctg tccggtaacg taagacagca gatacagagg   840
```

```
ccatccaaac acctgctggg tgatgaggcc gtagagggtc atgaggggag cgtcctcagc    900
aagctcagac cagtcatggg cgcctcggtt ctccataaac tcctttcggt ccttgggcac    960
aaacaccata tcacgggtga ggtgaccagt ggacttgtgg tgcatggagt gggtcagctt   1020
ccaggcgtag taagggacca gcatggagga gtgcagaacc catccggtga cgttgttgac   1080
ggtgttagag tcggagaaag cagagtggcc acactcgtgg gcaagaaccc acagaccggt   1140
gccaaacaga ccctggacaa tggagtacat ggcccaggcc acagctcggc cggaagccga   1200
gggaataaga ggcaggtacg cgtaggccat gtaggcaaaa acggcgataa agaagcagtc   1260
tcgggccacg tacgagtagg acttaacgta ggaccgcttg tagcactcct ggggaatggc   1320
atccagaata tccttgatag agtagtctgg aggagtgaac tcgttgccaa aggtgtcgta   1380
gacgggctcg gacaccttct caatgggctt aatgaaggcc gtgggggggct gcacggccac   1440
cttgccggtg ccggtgttgg tctgcgtggt cgaatccatg gtgaatgatt cttatactca   1500
gaaggaaatg cttaacgatt tcgggtgtga gttgacaagg agagagagaa aagaagagga   1560
aaggtaattc ggggacggtg gtcttttata cccttggcta aagtcccaac cacaaagcaa   1620
aaaaattttc agtagtctat tttgcgtccg gcatggggtta cccggatggc cagacaaaga   1680
aactagtaca aagtctgaac aagcgtagat tccagactgc agtaccctac gcccttaacg   1740
gcaagtgtgg gaaccggggg aggtttgata tgtggggtga aggggggctct cgccggggtt   1800
gggcccgcta ctgggtcaat ttggggtcaa ttggggcaat tggggctgtt ttttgggaca   1860
caaatacgcc gccaacccgg tctctcctga attctgcaga tgggctgcag gaattccgtc   1920
gtcgcagatc taacaagcta ccaccacact cgttgggtgc agtcgccagc ttaaagatat   1980
ctatccacat cagccacaac tcccttcctt aataaaccg actacaccct tggctattga   2040
ggttatgagt gaatatactg tagacaagac actttcaaga agactgtttc caaaacgtac   2100
cactgtcctc cactacaaac acacccaatc tgcttcttct agtcaaggtt gctacaccgg   2160
taaattataa atcatcattt cattagcagg gcagggccct tttatagag tcttatacac   2220
tagcggaccc tgccggtaga ccaacccgca ggcgcgtcag tttgctcctt ccatcaatgc   2280
gtcgtagaaa cgacttactc cttcttgagc agctccttga ccttgttggc aacaagtctc   2340
cgacctcgga ggtggaggaa gagcctccga tatcggcggt agtgatacca gcctcgacgg   2400
actccttgac ggcagcctca acagcgtcac cggcgggctt catgttaaga gagaacttga   2460
gcatcatggc ggcagacaga atggtggcaa tgggggttgac cttctgcttg ccagagatcgg   2520
gggcagatcc gtgacagggc tcgtacgac cgaacgcctc gttggtgtcg ggcagagaag   2580
ccagagaggc ggagggcagc agacccagag aaccggggat gacggaggcc tcgtcggaga   2640
tgatatcgcc aaacatgttg gtggtgatga tgataccatt catcttggag ggctgcttga   2700
tgaggatcat ggcggccgag tcgatcagct ggtggttgag ctcgagctgg gggaattcgt   2760
ccttgaggac tcgagtgaca gtcttttcgcc aaagtcgaga ggaggccagc acgttggcct   2820
tgtcaagaga ccacacggga agaggggggt tgtgctgaag ggccaggaag gcggccattc   2880
gggcaattcg ctcaacctca ggaacggagt aggtctcggt gtcggaagcg acgccagatc   2940
cgtcatcctc ctttcgctct ccaaagtaga tacctccgac gagctctcgg acaatgatga   3000
agtcggtgcc ctcaacgttt cggatggggg agagatcggc gagcttgggc gacagcagct   3060
ggcagggtcg caggttggcg tacaggttca ggtcctttcg cagcttgagg agaccctgct   3120
cgggtcgcac gtcggttcgt ccgtcggag tggtccatac ggtgttggca gcgcctccga   3180
cagcaccgag cataatagag tcagcctttc ggcagatgtc gagagtagcg tcggtgatgg   3240
```

```
gctcgccctc cttctcaatg gcagctcctc caatgagtcg gtcctcaaac acaaactcgg   3300
tgccggaggc ctcagcaaca gacttgagca ccttgacggc ctcggcaatc acctcggggc   3360
cacagaagtc gccgccgaga agaacaatct tcttggagtc agtcttggtc ttcttagttt   3420
cgggttccat tgtggatgtg tgtggttgta tgtgtgatgt ggtgtgtgga gtgaaaatct   3480
gtggctggca aacgctcttg tatatatacg cacttttgcc cgtgctatgt ggaagactaa   3540
acctccgaag attgtgactc aggtagtgcg gtatcggcta gggacccaaa ccttgtcgat   3600
gccgatagcg ctatcgaacg tacccccagcc ggccgggagt atgtcggagg ggacatacga   3660
gatcgtcaag ggtttgtggc caactggtaa ataaatgatg tcgactcagg cgacgacgga   3720
attcctgcag cccatctgca gaattcagga gagaccgggt tggcggcgta tttgtgtccc   3780
aaaaaacagc cccaattgcc ccaattgacc ccaaattgac ccagtagcgg gcccaacccc   3840
ggcgagagcc cccttcaccc cacatatcaa acctcccccg gttcccacac ttgccgttaa   3900
gggcgtaggg tactgcagtc tggaatctac gcttgttcag actttgtact agtttctttg   3960
tctggccatc cgggtaaccc atgccggacg caaaatagac tactgaaaat ttttttgctt   4020
tgtggttggg actttagcca agggtataaa agaccaccgt ccccgaatta cctttcctct   4080
tcttttctct ctctccttgt caactccacc ccgaaatcgt taagcatttc cttctgagta   4140
taagaatcat tcaccatggc tgccgctccc tctgtgcgaa cctttacccg agccgaggtt   4200
ctgaacgctg aggctctgaa cgagggcaag aaggacgctg aggctcccct cctgatgatc   4260
atcgacaaca aggtgtacga cgtccagaga ttcgtccctg accatcctgg aggctccgtg   4320
attctcaccc acgttggcaa ggacggcacc gacgtctttg acacctttca tcccgaggct   4380
gcttgggaga ctctcgccaa cttctacgtt ggagacattg acgagtccga ccgagacatc   4440
aagaacgatg actttgccgc tgaggtccga aagctgcgaa ccctgttcca gtctctcggc   4500
tactacgact cctctaaggc ctactacgcc ttcaaggtct ccttcaacct ctgcatctgg   4560
ggactgtcca ccgtcattgt ggccaagtgg ggtcagacct ccaccctcgc caacgtgctc   4620
tctgctgccc tgctcggcct gttctggcag cagtgcggat ggctggctca cgactttctg   4680
caccaccagg tcttccagga ccgattctgg ggtgatctct tcggagcctt cctgggaggt   4740
gtctgccagg gcttctcctc ttcctggtgg aaggacaagc acaacactca ccatgccgct   4800
cccaacgtgc atggcgagga tcctgacatt gacacccacc ctctcctgac ctggtccgag   4860
cacgctctgg agatgttctc cgacgtcccc gatgaggagc tgacccgaat gtggtctcga   4920
ttcatggtcc tgaaccagac ctggttctac ttccccattc tctccttcgc tcgactgtct   4980
tggtgcctcc agtccattct ctttgtgctg cccaacggtc aggctcacaa gccctccgga   5040
gctcgagtgc ccatctccct ggtcgagcag ctgtccctcg ccatgcactg gacctggtac   5100
ctcgctacca tgttcctgtt catcaaggat cctgtcaaca tgctcgtgta cttcctggtg   5160
tctcaggctg tgtgcggaaa cctgctcgcc atcgtgttct ccctcaacca caacggtatg   5220
cctgtgatct ccaaggagga ggctgtcgac atggattttct ttaccaagca gatcatcact   5280
ggtcgagatg tccatcctgg actgttcgcc aactggttca ccggtggcct gaactaccag   5340
atcgagcatc acctgttccc ttccatgcct cgacacaact tctccaagat ccagcctgcc   5400
gtcgagaccc tgtgcaagaa gtacaacgtc cgataccaca ccactggtat gatcgaggga   5460
actgccgagg tcttctcccg actgaacgag gtctccaagg ccacctccaa gatgggcaag   5520
gctcagtaag cggccgccac cgcggcccga gattccggcc tcttcggccg ccaagcgacc   5580
```

-continued

```
cgggtggacg tctagaggta cctagcaatt aacagatagt tgccggtga taattctctt   5640 aacctcccac actcctttga cataacgatt tatgtaacga aactgaaatt tgaccagata   5700
ttgtgtccgc ggtggagctc cagcttttgt tccctttagt gagggttaat ttcgagcttg   5760
gcgtaatcat ggtcatagct gtttcctgtg tgaaattgtt atccgctcac aagcttccac   5820
acaacgtacg gaccacctcc cttgcacttc ttggtatatc agtataggct gatgtattca   5880
tagtggggtt tttcataata aatttactaa cggcaggcaa cattcactcg gcttaaacgc   5940
aaaacggacc gtcttgatat cttctgacgc attgaccacc gagaaatagt gttagttacc   6000
gggtgagtta ttgttcttct acacagcgac gcccatcgtc tagagttgat gtactaactc   6060
agatttcact acctaccta tccctggtac gcacaggcgc gccagctgca ttaatgaatc   6120
ggccaacgcg cggggagagg cggtttgcgt attgggcgct cttccgcttc ctcgctcact   6180
gactcgctgc gctcggtcgt tcggctgcgg cgagcggtat cagctcactc aaaggcggta   6240
atacggttat ccacagaatc aggggataac gcaggaaaga acatgtgagc aaaaggccag   6300
caaaaggcca ggaaccgtaa aaaggccgcg ttgctggcgt ttttccatag gctccgcccc   6360
cctgacgagc atcacaaaaa tcgacgctca agtcagaggt ggcgaaaccc gacaggacta   6420
taaagatacc aggcgtttcc ccctggaagc tccctcgtgc gctctcctgt tccgaccctg   6480
ccgcttaccg gatacctgtc cgcctttctc ccttcgggaa gcgtggcgct ttctcatagc   6540
tcacgctgta ggtatctcag ttcggtgtag tcgttcgct ccaagctggg ctgtgtgcac   6600 gaacccccg ttcagcccga ccgctgcgcc ttatccggta actatcgtct tgagtccaac   6660
ccggtaagac acgacttatc gccactggca gcagccactg gtaacaggat tagcagagcg   6720
aggtatgtag gcggtgctac agagttcttg aagtggtggc ctaactacgg ctacactaga   6780
agaacagtat ttggtatctg cgctctgctg aagccagtta ccttcggaaa aagagttggt   6840
agctcttgat ccggcaaaca aaccaccgct ggtagcggtg ttttttgt ttgcaagcag   6900 cagattacgc gcagaaaaaa aggatctcaa gaagatcctt tgatcttttc tacgggtct   6960 gacgctcagt ggaacgaaaa ctcacgttaa gggattttgg tcatgagatt atcaaaaagg   7020
atcttcacct agatcctttt aaattaaaaa tgaagtttta aatcaatcta agtatatat   7080 gagtaaactt ggtctgacag ttaccaatgc ttaatcagtg aggcacctat ctcagcgatc   7140
tgtctatttc gttcatccat agttgcctga ctccccgtcg tgtagataac tacgatacgg   7200
gagggcttac catctggccc cagtgctgca atgataccgc gagacccacg ctcaccggct   7260
ccagatttat cagcaataaa ccagccagcc ggaagggccg agcgcagaag tggtcctgca   7320
actttatccg cctccatcca gtctattaat tgttgccggg aagctagagt aagtagttcg   7380
ccagttaata gtttgcgcaa cgttgttgcc attgctacag gcatcgtggt gtcacgctcg   7440
tcgtttggta tggcttcatt cagctccggt tcccaacgat caaggcgagt tacatgatcc   7500
cccatgttgt gcaaaaaagc ggttagctcc ttcggtcctc cgatcgttgt cagaagtaag   7560
ttggccgcag tgttatcact catggttatg gcagcactgc ataattctct tactgtcatg   7620
ccatccgtaa gatgcttttc tgtgactggt gagtactcaa ccaagtcatt ctgagaatag   7680
tgtatgcggc gaccgagttg ctcttgcccg gcgtcaatac gggataatac cgcgccacat   7740
agcagaactt taaaagtgct catcattgga aaacgttctt cggggcgaaa actctcaagg   7800
atcttaccgc tgttgagatc cagttcgatg taacccactc gtgcacccaa ctgatcttca   7860
gcatctttta ctttcaccag cgtttctggg tgagcaaaaa caggaaggca aaatgccgca   7920
aaaaagggaa taagggcgac acggaaatgt tgaatactca tactcttcct ttttcaatat   7980
```

```
tattgaagca tttatcaggg ttattgtctc atgagcggat acatatttga atgtatttag    8040
aaaaataaac aaatagggt tccgcgcaca tttccccgaa aagtgccacc tgatgcggtg    8100
tgaaataccg cacagatgcg taaggagaaa ataccgcatc aggaaattgt aagcgttaat    8160
attttgttaa aattcgcgtt aaatttttgt taaatcagct cattttttaa ccaataggcc    8220
gaaatcggca aaatccctta taaatcaaaa gaatagaccg atagggtt gagtgttgtt    8280 ccagtttgga acaagagtcc actattaaag aacgtggact ccaacgtcaa agggcgaaaa    8340
accgtctatc agggcgatgg cccactacgt gaaccatcac cctaatcaag ttttttgggg    8400
tcgaggtgcc gtaaagcact aaatcggaac cctaaaggga ccccgatt tagagcttga    8460 cggggaaagc cggcgaacgt ggcgagaaag gaagggaaga aagcgaaagg agcgggcgct    8520
agggcgctgg caagtgtagc ggtcacgctg cgcgtaacca ccacacccgc cgcgcttaat    8580
gcgccgctac agggcgcgtc cattcgccat tcaggctgcg caactgttgg gaagggcgat    8640
cggtgcgggc ctcttcgcta ttacgccagc tggcgaaagg gggatgtgct gcaaggcgat    8700
taagttgggt aacgccaggg ttttcccagt cacgacgttg taaaacgacg ccagtgaat    8760 tgtaatacga ctcactatag gcgaattgg gcccgacgtc gcatgctgtg taacactcgc    8820
tctggagagt tagtcatccg acagggtaac tctaatctcc caacaccta ttaactctgc    8880 gtaactgtaa ctcttcttgc cacgtcgatc ttactcaatt ttcctgctca tcatctgctg    8940
gattgttgtc tatcgtctgg ctctaataca tttattgttt attgcccaaa caactttcat    9000
tgcacgtaag tgaattgttt tataacagcg ttcgccaaat tgctgcgcca tcgtcgtccg    9060
gctgtcctac cgttaggggt agtgtgtctc acactaccga ggttactaga gttgggaaag    9120
cgatactgcc tcggacacac cacctgggtc ttacgactgc agagagaatc ggcgttaatt    9180
aactcacctg caggattgag actatgaatg gattcccgtg cccgtattac tctactaatt    9240
tgatcttgga acgcgaaaat acgtttctag gactccaaag aatctcaact cttgtccttag    9300 ctaaatatac tacccatagt tgatggttta cttgaacaga gaggacatgt tcacttgacc    9360
caaagtttct cgcatctctt ggatatttga acaacggcgt ccactgaccg tcagttatcc    9420
agtcacaaaa cccccacatt catacattcc catgtacgtt tacaaagttc tcaattccat    9480
cgtgcaaatc aaaatcacat ctattcattc atcatatata aacccatcat gtctactaac    9540
actcacaact ccatagaaaa catcgactca gaacacacgc tccatgcggc cgcctacttt    9600
ttagaaggca ggccgtcagg agcaactccg actccattga cgtttctaaa catctgaatg    9660
ccttccttac cttcaacaaa ctggcaggtt cgggcgacag tgtaaagaga cttgatgaag    9720
ttggtgtcgt cgtgtcggta gtgcttgccc atgaccttct tgatcttctc agtgcgatt    9780 cgggcgttgt agaagggaat tcgagacacg tagtggtgca gaacgtgggt ctcgatgatg    9840
tcatggaagc agaaggagcc gatgaagcca aactctcggt cgatggtggc ggcggctcct    9900
cgggtgaagt tccactggtc ggcgtggtag tggggcagag tggggtcggt gtgctgcagg    9960
taggtgatgg ccacgagcca gtggttgacc cacaggtagg ggatcaggta gtagagggtg   10020
acggaagcca ggccccatcg gttgatggag tatgcgatga cggacatggt gataccaata   10080
ccgacgttag agatccagat gttgaaccag tccttcttct caaacagcgg ggcgttgggg   10140
ttgaagtggt tgacagccca tttgttgagc ttgggtact tctgtccggt aacgtaagac   10200
agcagataca gaggccatcc aaacacctgc tgggtgatga ggccgtagag ggtcatgagg   10260
ggagcgtcct cagcaagctc agaccagtca tgggcgcctc ggttctccat aaactccttt   10320
```

-continued

```
cggtccttgg gcacaaacac catatcacgg gtgaggtgac cagtggactt gtggtgcatg    10380
gagtgggtca gcttccaggc gtagtaaggg accagcatgg aggagtgcag aacccatccg    10440
gtgacgttgt tgacggtgtt agagtcggag aaagcagagt ggccacactc gtgggcaaga    10500
acccacagac cggtgccaaa cagaccctgg acaatggagt acatggccca ggccacagct    10560
cggccggaag ccgagggaat aagaggcagg tacgcgtagg ccatgtaggc aaaaacggcg    10620
ataaagaagc agtctcgggc cacgtacgag taggacttaa cgtaggaccg cttgtagcac    10680
tcctggggaa tggcatccag aatatccttg atagagtagt ctggaggagt gaactcgttg    10740
ccaaaggtgt cgtagacggg ctcggacacc ttctcaatgg gcttaatgaa ggccgtgggg    10800
ggctgcacgg ccaccttgcc ggtgccggtg ttggtctgcg tggtcgaatc catggttgat    10860
gtgtgtttaa ttcaagaatg aatatagaga agagaagaag aaaaaagatt caattgagcc    10920
ggcgatgcag acccttatat aaatgttgcc ttggacagac ggagcaagcc cgcccaaacc    10980
tacgttcggt ataatatgtt aagcttttta acacaaaggt ttggcttggg gtaacctgat    11040
gtggtgcaaa agaccgggcg ttggcgagcc attgcgcggg cgaatggggc cgtgactcgt    11100
ctcaaattcg agggcgtgcc tcaattcgtg cccccgtggc ttttccccgc cgtttccgcc    11160
ccgtttgcac cactgcagcc gcttctttgg ttcggacacc ttgctgcgag ctaggtgcct    11220
tgtgctactt aaaaagtggc ctcccaacac caacatgaca tgagtgcgtg gccaagaca    11280 cgttggcggg gtcgcagtcg gctcaatggc ccggaaaaaa cgctgctgga gctggttcgg    11340
acgcagtccg ccgcggcgta tggatatccg caaggttcca tagcgccatt gccctccgtc    11400
ggcgtctatc ccgcaacctc taaatagagc gggaatataa cccaagcttc tttttttttcc    11460 tttaacacgc acaccccaaa ctatcatgtt gctgctgctg tttgactcta ctctgtggag    11520
gggtgctccc acccaaccca acctacaggt ggatccggcg ctgtgattgg ctgataagtc    11580
tcctatccgg actaattctg accaatggga catgcgcgca ggacccaaat gccgcaatta    11640
cgtaacccca acgaaatgcc tacccctctt tggagcccag cggccccaaa tccccccaag    11700
cagcccggtt ctaccggctt ccatctccaa gcacaagcag cccggttcta ccggcttcca    11760
tcgatcccta actgtatact agcattctga attaatatct tcctctttga ttgttcctta    11820
ggcatatcag cggggatccc gtcaacagtt ttatatatcg tagttacaac catcaacact    11880
ttttggtaag tgtaccattc tatactccaa ctggtctgca actgtacaag tagacatgtt    11940
aatggtagtt aataacatct acagcagaac ctatggtaaa gacattgcat ttttacagga    12000
agtatcgtcc tacacgttga taaatccaaa gatgcggaac ttcttccact tttatcatca    12060
tcccctactc gtacactcgt actctttgtt cgatcgcgat tcatttctat aaataatctt    12120
gtatgtacat gcggccgctt acatggcggg aaactccttg aagaactcga tcgagatgcg    12180
ctcgaggtgc acgacgacct cggccatgcc cgcgatgaag cccgtctcgt ggtatgggat    12240
gtcgtactgc ttgcagagcg acttgacgag cacgttgagc gccggaggt tgtgccgggg    12300 caccatcggg aacaagtggt ggtcgatctg gtagttgagg ccgcccatga accagtcgat    12360
ccagagcgac gacgtcacgt tgcgcgtcga gagcacttgc agcttccaaa aatcgggctt    12420
gctgtccttg tcaaagacct ccatgccgtt gtggccgacg ctaaagacca tcgcgaggaa    12480
gaggccgcac gacgcctggc tcacaaagag gaacgcagcc gcttggagca gcgacatgtt    12540
ggctgcgtac acaaggccga ggttccagcc gtagtagagg aggaggccgg cgcgctcgag    12600
cagcgggtac tggaccttgt caaggtgcc gccgggccca acgttgtaga aggcgtacat    12660
ggccgactgg atcacccacg agatacgcgc aaagagcaag atgggaaagt acaggtacgc    12720
```

```
ttggtagcgc atgaagaaga gcccgacggg cgagtcgacc gcgtgctgcg ccatcttgag   12780
cgaccacgcg agaatcggca tcgtgtcaat gtccgggtcg ccgtggaagg cgatctcggg   12840
cgtcgcgtgg aggttgggga tcgcatggtg cgtgttgtgc ttgttcttcc accactgcac   12900
cgagaagccc tgccagaggt tgccgaccat gacgccgacg aggtcgccaa acaagtggtt   12960
ctcaaacact tggtggtgca gaaagtcatg ggcgagccag ccgcactgct ggtaaaagag   13020
gccaaggatg acagccgcga ccatgtacat ggccgtcgag tcaaagtgga ggcaaatggc   13080
cgccgacaca agcgcaatgc tcagcgtcga ggcgcacttg tagaggtagt agagcttgct   13140
cgagtcgtac aagccgaggc gcttgacttc aaggcgcagc ttgcggtacg acgcaatgaa   13200
gtccgactgg ctcttcttga cctcgtccga gatcgacgtg tcgacggccg ccgtcgactg   13260
gtcgacgtcg ccgacgtagt actgctcgag gagcttgagc gccgagctcg ggtggaagac   13320
agcgaacgca tcggtcgcgt cttcgccggc ctgcgtgaac atgacgacgc cgcccgggtg   13380
gtcctcaaag gccgagatgt cgtacacctt gtggtggatc acgatccacg cgttgtcttg   13440
gcggttgtgc tcacggatgg tcgcccacga gatcttctcg gcctttttgcc cctggaccat   13500 ggtgaatgat tcttatactc agaaggaaat gcttaacgat ttcgggtgtg agttgacaag   13560
gagagagaga aaagaagagg aaaggtaatt cggggacggt ggtctttat accccttggct   13620 aaagtcccaa ccacaaagca aaaaattttt cagtagtcta ttttgcgtcc ggcatggggtt   13680 acccggatgg ccagacaaag aaactagtac aaagtctgaa caagcgtaga ttccagactg   13740
cagtacccta cgcccttaac ggcaagtgtg ggaaccgggg gaggtttgat atgtggggtg   13800 aaggggggctc tcgccggggt tgggcccgct actgggtcaa tttggggtca attgggcaa   13860 ttgggggctgt tttttgggac acaaatacgc cgccaacccg tctctcctg aattctgcag   13920 atgggctgca ggaattccgt cgttt                                         13945
```

<210> SEQ ID NO 41
<211> LENGTH: 10
<212> TYPE: DNA
<213> ORGANISM: Yarrowia lipolytica
<220> FEATURE:
<221> NAME/KEY: misc_feature
<222> LOCATION: (8)..(8)
<223> OTHER INFORMATION: n is a, c, g, or t

<400> SEQUENCE: 41 mammatgnhs                                                          10

<210> SEQ ID NO 42
<211> LENGTH: 2177
<212> TYPE: DNA
<213> ORGANISM: Yarrowia lipolytica

<400> SEQUENCE: 42

```
agtcgaggac ttatcctagc ctcygaatac tttcaacaag ttacaccctt attccccacc     60
aagccgctag atacgccact aagcaaagtt caagagccat cgcacaatta tctacgagta    120
ccgcagcaat cattcatttc aaggcacaca tggggtttct cttgcagaaa aacgcacggt    180
ttcaaagtat aaacgcacat ctaggccgag acaagttgcg gggtatggta ctagtatttc    240
cgggtgcatt ccacgggtga atgggcgttt agaattgagg caattgccac gggttgggcc    300
acatatgttg agtactcatt tctcctctca atgaacgtct ccagaatgac atacattctc    360
ctccaacacc ttgtggggta aacttctgtc agattccacg taacaaggtt ggtgtcggaa    420
```

```
caacgaaaaa ggatcggaac agagcttccg gtgtcggtga ttgggcaggg ggctgaggcg      480
tgcctggcgc gtgcgcgtgg tagagagagt gtgctacagc agagagatat tactcgtttg      540
gagctagaga tgccgccgtt gaagaaatta acgaacgagt aactaacaga ccattccagg      600
atcatcgagg accgttgtca gcgcccttac tacagaaatg tatgtacagt aattacaact      660
gcgcggctgc ttgacggatg tatggagtct aagtaatgag tgcgtacgta gcaacaacag      720
tgtacgcagt actatagagg aacaattgcc ccggagaaga cggccaggcc gcctagatga      780
caaattcaac aactcacagc tgactttctg ccattgccac tagggggggg cctttttata      840
tggccaagcc aagctctcca cgtcggttgg gctgcaccca acaataaatg ggtagggttg      900
caccaacaaa gggatgggat gggggtaga agatacgagg ataacggggc tcaatggcac      960
aaataagaac gaatactgcc attaagactc gtgatccagc gactgacacc attgcatcat     1020
ctaagggcct caaaactacc tcggaactgc tgcgctgatc tggacaccac agaggttccg     1080
agcactttag gttgcaccaa atgtcccacc aggtgcaggc agaaaacgct ggaacagcgt     1140
gtacagtttg tcttaacaaa aagtgagggc gctgaggtcg agcagggtgg tgtgacttgt     1200
tatagccttt agagctgcga aagcgcgtat ggatttggct catcaggcca gattgagggt     1260
ctgtggacac atgtcatgtt agtgtacttc aatcgccccc tggatatagc cccgacaata     1320
ggccgtggcc tcattttttt gccttccgca catttccatt gctcggtacc cacaccttgc     1380
ttctcctgca cttgccaacc ttaatactgg tttacattga ccaacatctt acaagcgggg     1440
ggcttgtcta gggtatatat aaacagtggc tctcccaatc ggttgccagt ctcttttttc     1500
ctttctttcc ccacagattc gaaatctaaa ctacacatca cacaatgcct gttactgacg     1560
tccttaagcg aaagtccggt gtcatcgtcg gcgacgatgt ccgagccgtg agtatccacg     1620
acaagatcag tgtcgagacg acgcgttttg tgtaatgaca caatccgaaa gtcgctagca     1680
acacacactc tctacacaaa ctaacccagc tcttcgagta cgcccgagag cacaagttcg     1740
ccctccccgc cgtcaacgtg acctcttcgt ccaccgttgt cgccgttctt gagtctgccc     1800
gagccaacaa gtccccgtc atcatccaga tgtcccaggg tggcgctgcc tactttgctg     1860
gcaagggtgt cgacaacaag gatcagaccg cctccatcca gggagccatt gccgctgccc     1920
agttcatccg aaccattgct cccgtttacg gcattcccgt catcgtccac accgaccact     1980
gtgcccgaaa gctgctcccc tggctcgacg gtatgctcga cgccgatgag gagtacttca     2040
agactcacgg tgagcccctc ttctcttcac acatggtgga tctctccgag gaggagcacc     2100
ccgagaacat cgccaccacc gccgagtact tcaagcgagc cgccaagatg aaccagtggc     2160
tcgagatgga gatcggc                                                    2177
```

<210> SEQ ID NO 43
<211> LENGTH: 995
<212> TYPE: DNA
<213> ORGANISM: Yarrowia lipolytica

<400> SEQUENCE: 43

```
agtgtacgca gtactataga ggaacaattg ccccggagaa gacggccagg ccgcctagat       60
gacaaattca caactcacag ctgactttc tgccattgcc actagggggg ggcctttttta      120 tatggccaag ccaagctctc acgtcggtt gggctgcacc caacaataaa tgggtagggt      180
tgcaccaaca aagggatggg atgggggta gaagatacga ggataacggg gctcaatggc      240
acaaataaga acgaatactg ccattaagac tcgtgatcca gcgactgaca ccattgcatc      300
atctaagggc ctcaaaacta cctcggaact gctgcgctga tctggacacc acagaggttc      360
```

```
cgagcacttt aggttgcacc aaatgtccca ccaggtgcag gcagaaaacg ctggaacagc      420
gtgtacagtt tgtcttaaca aaaagtgagg gcgctgaggt cgagcagggt ggtgtgactt      480
gttatagcct ttagagctgc gaaagcgcgt atggatttgg ctcatcaggc cagattgagg      540
gtctgtggac acatgtcatg ttagtgtact tcaatcgccc cctggatata gccccgacaa      600
taggccgtgg cctcattttt ttgccttccg cacatttcca ttgctcggta cccacacctt      660
gcttctcctg cacttgccaa ccttaatact ggtttacatt gaccaacatc ttacaagcgg      720
ggggcttgtc tagggtatat ataaacagtg gctctcccaa tcggttgcca gtctcttttt      780
tcctttcttt ccccacagat tcgaaatcta aactacacat cacacaatgc ctgttactga      840
cgtccttaag cgaaagtccg gtgtcatcgt cggcgacgat gtccgagccg tgagtatcca      900
cgacaagatc agtgtcgaga cgacgcgttt tgtgtaatga cacaatccga aagtcgctag      960
caacacacac tctctacaca aactaaccca gctct                                995

<210> SEQ ID NO 44
<211> LENGTH: 1434
<212> TYPE: DNA
<213> ORGANISM: Fusarium monoliforme

<400> SEQUENCE: 44
atggcgtcca cttcggctct gcccaagcag aaccctgcgc ttagacgcac cgtcacctca       60
actactgtga cggattctga gtctgccgcc gtctctcctt cagactctcc ccgccactcg      120
gcctcttcca catcgctctc gtccatgtcc gaggttgata tcgccaagcc caagtccgag      180
tatggtgtca tgctcgacac ctacggcaac cagttcgagg ttcccgactt taccatcaag      240
gacatctaca atgccatccc taagcactgc ttcaagcgct ccgctctcaa gggatacggt      300
tatatcctcc gcgacattgt cctcctgact accactttca gcatctggta caactttgtg      360 accccccgaat atatcccctc caccccccgcc cgcgctggtc tgtgggccgt gtacaccgtt      420
cttcagggtc ttttcggtac tggtctctgg gttattgccc atgagtgcgg tcacggtgct      480
ttctccgatt ctcgcatcat caacgacatt actggctggg ttcttcactc ttccctcctt      540
gtcccctact tcagctggca aatctcccac cgaaagcacc acaaggccac tggcaacatg      600
gagcgtgaca tggtcttcgt tccccgaacc cgcgagcagc aggctactcg tctcggaaag      660
atgacccacg agctcgctca tcttactgag gagaccccccg ctttcactct tctcatgctc      720
gtccttcagc agctcgttgg ctggcccaac tacctcatca ccaatgttac cggccacaac      780
taccacgagc gccagcgtga gggtcgcggc aagggcaagc ataacggcct cggcggtggt      840
gttaaccact cgatccccg cagccctctg tacgagaaca gtgacgctaa gctcatcgtc      900
ctcagcgata ttggtatcgg tctgatggcc actgctctgt acttcctcgt tcagaagttc      960
ggtttctaca acatggccat ctggtacttt gttccctacc tctgggttaa ccactggctc     1020
gttgccatca ccttcctcca gcacaccgac cctacccttc ccactacac caacgacgag     1080 tggaacttcg tccgtggtgc cgctgctacc attgaccgtg agatgggctt catcggccgc     1140
caccttctcc acggcatcat cgagactcat gtcctccacc actacgtcag cagcatcccc     1200
ttctacaacg cggacgaggc caccgaggcc attaagccca tcatgggcaa gcactaccgg     1260
gctgatgtcc aggatggtcc tcgtggcttc atccgcgcca tgtaccgcag tgcgcgtatg     1320
tgccagtggg ttgagcccag cgctggtgcc gagggtgctg gtaagggtgt tctgttcttc     1380
cgcaaccgca acaacgtggg caccccccccc gctgttatca agcccgttgc ttaa          1434
```

```
<210> SEQ ID NO 45
<211> LENGTH: 477
<212> TYPE: PRT
<213> ORGANISM: Fusarium monoliforme

<400> SEQUENCE: 45

Met Ala Ser Thr Ser Ala Leu Pro Lys Gln Asn Pro Ala Leu Arg Arg
1               5                   10                  15

Thr Val Thr Ser Thr Thr Val Thr Asp Ser Glu Ser Ala Ala Val Ser
            20                  25                  30

Pro Ser Asp Ser Pro Arg His Ser Ala Ser Ser Thr Ser Leu Ser Ser
        35                  40                  45

Met Ser Glu Val Asp Ile Ala Lys Pro Lys Ser Glu Tyr Gly Val Met
    50                  55                  60

Leu Asp Thr Tyr Gly Asn Gln Phe Glu Val Pro Asp Phe Thr Ile Lys
65                  70                  75                  80

Asp Ile Tyr Asn Ala Ile Pro Lys His Cys Phe Lys Arg Ser Ala Leu
                85                  90                  95

Lys Gly Tyr Gly Tyr Ile Leu Arg Asp Ile Val Leu Leu Thr Thr Thr
            100                 105                 110

Phe Ser Ile Trp Tyr Asn Phe Val Thr Pro Glu Tyr Ile Pro Ser Thr
        115                 120                 125

Pro Ala Arg Ala Gly Leu Trp Ala Val Tyr Thr Val Leu Gln Gly Leu
    130                 135                 140

Phe Gly Thr Gly Leu Trp Val Ile Ala His Glu Cys Gly His Gly Ala
145                 150                 155                 160

Phe Ser Asp Ser Arg Ile Ile Asn Asp Ile Thr Gly Trp Val Leu His
                165                 170                 175

Ser Ser Leu Leu Val Pro Tyr Phe Ser Trp Gln Ile Ser His Arg Lys
            180                 185                 190

His His Lys Ala Thr Gly Asn Met Glu Arg Asp Met Val Phe Val Pro
        195                 200                 205

Arg Thr Arg Glu Gln Gln Ala Thr Arg Leu Gly Lys Met Thr His Glu
    210                 215                 220

Leu Ala His Leu Thr Glu Glu Thr Pro Ala Phe Thr Leu Leu Met Leu
225                 230                 235                 240

Val Leu Gln Gln Leu Val Gly Trp Pro Asn Tyr Leu Ile Thr Asn Val
                245                 250                 255

Thr Gly His Asn Tyr His Glu Arg Gln Arg Glu Gly Arg Gly Lys Gly
            260                 265                 270

Lys His Asn Gly Leu Gly Gly Val Asn His Phe Asp Pro Arg Ser
        275                 280                 285

Pro Leu Tyr Glu Asn Ser Asp Ala Lys Leu Ile Val Leu Ser Asp Ile
    290                 295                 300

Gly Ile Gly Leu Met Ala Thr Ala Leu Tyr Phe Leu Val Gln Lys Phe
305                 310                 315                 320

Gly Phe Tyr Asn Met Ala Ile Trp Tyr Phe Val Pro Tyr Leu Trp Val
                325                 330                 335

Asn His Trp Leu Val Ala Ile Thr Phe Leu Gln His Thr Asp Pro Thr
            340                 345                 350

Leu Pro His Tyr Thr Asn Asp Glu Trp Asn Phe Val Arg Gly Ala Ala
        355                 360                 365

Ala Thr Ile Asp Arg Glu Met Gly Phe Ile Gly Arg His Leu Leu His
    370                 375                 380
```

Gly Ile Ile Glu Thr His Val Leu His His Tyr Val Ser Ser Ile Pro
385                 390                 395                 400

Phe Tyr Asn Ala Asp Glu Ala Thr Glu Ala Ile Lys Pro Ile Met Gly
            405                 410                 415

Lys His Tyr Arg Ala Asp Val Gln Asp Gly Pro Arg Gly Phe Ile Arg
        420                 425                 430

Ala Met Tyr Arg Ser Ala Arg Met Cys Gln Trp Val Glu Pro Ser Ala
    435                 440                 445

Gly Ala Glu Gly Ala Gly Lys Gly Val Leu Phe Phe Arg Asn Arg Asn
450                 455                 460

Asn Val Gly Thr Pro Pro Ala Val Ile Lys Pro Val Ala
465                 470                 475

<210> SEQ ID NO 46
<211> LENGTH: 804
<212> TYPE: DNA
<213> ORGANISM: Rattus norvegicus
<220> FEATURE:
<221> NAME/KEY: misc_feature
<223> OTHER INFORMATION: synthetic C16 elongase (codon-optimized)

<400> SEQUENCE: 46
atggacatgt ccgtcctgac tctccaagag tacgagttcg agaagcagtt caacgagaat      60
gaagccatcc aatggatgca ggaaaactgg aagaaatcct tcctgttttc tgccctctac     120
gctgccttta tctttggtgg acgacatctg atgaacaagc gagccaagtt tgagctgcga     180
aaacctctcg tgctctggtc cctgaccctc gctgtcttct ctatcttcgg tgctctgcga     240
actggagcct acatgctcta catcctgatg accaaaggcc tgaaacagtc tgtttgtgac     300
cagtcctttt acaacggacc cgtctcgaaa ttctgggctt acgcctttgt gctctccaaa     360
gctcccgaac ttggcgatac catcttcatc attctgcgaa agcagaaact catcttcctg     420
cactggtatc accacatcac cgtcctcctg tactcttggt actcctacaa ggacatggtg     480
gctgaggtg gctggttcat gactatgaac tacggtgtcc acgccgtgat gtactcctac     540
tacgccctcc gagctgccgg tttccgagtc tctcgaaagt ttgccatgtt catcaccctg     600
tcgcagatca ctcagatgct catgggctgt gtcattaact acctggtctt caactggatg     660
cagcatgaca atgaccagtg ctactcccac tttcagaaca tcttctggtc ctctctcatg     720
tacctctcct accttctgct cttctgccat tcttctttg aggcctacat tggcaaagtg     780
aagaaagcca ccaaggctga gtaa                                            804

<210> SEQ ID NO 47
<211> LENGTH: 2628
<212> TYPE: DNA
<213> ORGANISM: Rattus norvegicus (GenBank Accession No. AB071986)
<220> FEATURE:
<221> NAME/KEY: CDS
<222> LOCATION: (90)..(893)
<223> OTHER INFORMATION: C16 elongase

<400> SEQUENCE: 47
tggatgcgga cgctgggagg agagcccctg agctaggagc tgggagccga ggcgcagaga      60
acacgtagcg actccgaaga tcagccccca atg aac atg tca gtg ttg act tta     113
                                   Met Asn Met Ser Val Leu Thr Leu
                                     1               5 caa gaa tat gaa ttc gag aag cag ttc aac gag aat gaa gcc atc caa     161
Gln Glu Tyr Glu Phe Glu Lys Gln Phe Asn Glu Asn Glu Ala Ile Gln
    10                  15                  20

| | | |
|---|---|---|
| tgg atg cag gaa aac tgg aag aaa tct ttc ctg ttt tct gcg ctg tac<br>Trp Met Gln Glu Asn Trp Lys Lys Ser Phe Leu Phe Ser Ala Leu Tyr<br>25                           30                      35                   40 | | 209 |
| gct gcc ttt ata ttt ggt ggt cgg cat ctg atg aac aag cgg gcc aag<br>Ala Ala Phe Ile Phe Gly Gly Arg His Leu Met Asn Lys Arg Ala Lys<br>                        45                      50                      55 | | 257 |
| ttt gaa ctg cgg aag ccg ctc gtg ctc tgg tca ctg act ctt gcg gtc<br>Phe Glu Leu Arg Lys Pro Leu Val Leu Trp Ser Leu Thr Leu Ala Val<br>             60                      65                      70 | | 305 |
| ttc agt ata ttc ggt gct ctt cga act ggt gct tac atg ctg tac att<br>Phe Ser Ile Phe Gly Ala Leu Arg Thr Gly Ala Tyr Met Leu Tyr Ile<br>        75                      80                      85 | | 353 |
| ttg atg acc aaa ggc ctg aag cag tca gtt tgt gac cag agt ttt tac<br>Leu Met Thr Lys Gly Leu Lys Gln Ser Val Cys Asp Gln Ser Phe Tyr<br>90                           95                      100 | | 401 |
| aac gga cct gtc agc aaa ttc tgg gct tac gcg ttt gtg ctc agc aaa<br>Asn Gly Pro Val Ser Lys Phe Trp Ala Tyr Ala Phe Val Leu Ser Lys<br>105                     110                     115                  120 | | 449 |
| gca ccc gaa cta ggt gat acg ata ttc atc att ctg agg aag cag aag<br>Ala Pro Glu Leu Gly Asp Thr Ile Phe Ile Ile Leu Arg Lys Gln Lys<br>                        125                     130                      135 | | 497 |
| ctg atc ttc ctg cac tgg tac cac cac atc act gtg ctc ctg tac tct<br>Leu Ile Phe Leu His Trp Tyr His His Ile Thr Val Leu Leu Tyr Ser<br>                 140                     145                     150 | | 545 |
| tgg tac tcc tac aaa gac atg gta gct ggg ggt ggt tgg ttc atg act<br>Trp Tyr Ser Tyr Lys Asp Met Val Ala Gly Gly Gly Trp Phe Met Thr<br>               155                     160                     165 | | 593 |
| atg aac tat ggc gta cac gcc gtc atg tac tct tac tac gcc ttg cgg<br>Met Asn Tyr Gly Val His Ala Val Met Tyr Ser Tyr Tyr Ala Leu Arg<br>         170                     175                     180 | | 641 |
| gct gcg ggt ttc cgg gtc tcc cgg aag ttt gcc atg ttc atc acg ttg<br>Ala Ala Gly Phe Arg Val Ser Arg Lys Phe Ala Met Phe Ile Thr Leu<br>185                     190                     195                  200 | | 689 |
| tcc cag atc act cag atg ctg atg ggc tgt gtc att aac tac ctg gtc<br>Ser Gln Ile Thr Gln Met Leu Met Gly Cys Val Ile Asn Tyr Leu Val<br>                        205                     210                      215 | | 737 |
| ttc aac tgg atg cag cat gac aat gac cag tgc tac tcc cac ttt cag<br>Phe Asn Trp Met Gln His Asp Asn Asp Gln Cys Tyr Ser His Phe Gln<br>               220                     225                     230 | | 785 |
| aac atc ttc tgg tcc tca ctc atg tac ctc agc tac ctt ctg ctc ttc<br>Asn Ile Phe Trp Ser Ser Leu Met Tyr Leu Ser Tyr Leu Leu Leu Phe<br>         235                     240                     245 | | 833 |
| tgc cat ttc ttc ttt gag gcc tac atc ggc aaa gtg aag aaa gcg acg<br>Cys His Phe Phe Phe Glu Ala Tyr Ile Gly Lys Val Lys Lys Ala Thr<br>250                     255                     260 | | 881 |
| aag gcc gag tag tgtcagagct gaggaggaag acatagctca gggtcatcac<br>Lys Ala Glu<br>265 | | 933 |
| gaaaataat agacaaaaag aaaatggcac aaggaatcac atatggtgca gctaaaacaa | | 993 |
| aacaaaacat tatgagcaga cgctaagccc aaggcagctt gggagtgaag attaggttgt | | 1053 |
| aagtttatga tccttttttgg gtgaggactc actgagaaca ctgctgctga gggacccccct | | 1113 |
| tccctcttac ctgtcaactc tagaacacac tagaagccaa ggcagccatg gcaaggaga | | 1173 |
| ttagtggaca gcaagcaaaa cactgcagga agaggggggga gatctattca gagttttttg | | 1233 |
| ttttgttttg ttttgttttt ctctaaggat aaaggagttt cccctttttca aactgtgtga | | 1293 |
| gcacacccac gcgcatgcgg acacacacac acacacacat acacacacac acacacatac | | 1353 |

-continued

```
acacatacac acacacacac acacacacac acacaatctt ttccacagga aaccagagct    1413
ggtagaaaag ataaacggta agcgacaggg tttctatcta ggacagcaat gcttttgcaa    1473
aaacctaagc cttttaaaga agttagcttg taactccttg acaaaagatg tcttaattct    1533
ttttactgta actgaaagtc aaaaaggtag ataccttccc cttcactgca cagcctcggg    1593
cttgttcgtt tgctacaacg gagcagagga cagttcttcc gtgatacttt atttctggga    1653
gaaagaaaac catgcagccc aaatcccgag aaggcggccc atagctaacc ctgcagttga    1713
agcatcacac tgacagctgt tatttctgct cttcggtgag aattgaagca gccgttgttc    1773
aattacccca aactttagga tgggggagta aatacggaat tgaaagaaa gaagctcgac    1833 tggttggctt gaaaatggaa tcttgtacta tctataacaa aactcagccc atcgtccctg    1893
gagctggaag gactatcaga agagaccaga actgaagatt catccaatac acagatggca    1953
tgttcgcctc cttccccgtt tgacctcaca catagtcctg gctttctaaa tgaggtccta    2013
tgacccagtc tgtgttttct atattttgt gactttcaaa aacagatccg cagggctctg    2073
catttggggt aaacactgtg tttctgcagc ctctgcattc gctcccttca gcaatgcaga    2133
ggcgtgagaa gtgccctctg ctggcttagt gagaagcttc aacaaacact tcataatagg    2193
ttgaaatagc tgaccacaaa gggcctgcgt agattaaacc ctaagttaag ttctaagtgc    2253
tgtcaaacac ctgacatata tttgaccaaa tcagaagaga gagaacctct atgcttcaag    2313
taagcttcat aaaaaatttt taaagtgact ttcacttggg aactcagaaa gtcaatgtat    2373
taagagccat attcttaaaa aaaaaagaa agaaagaaaa gaagaagaag aaagctagac    2433
aatgttatct gtaatatttc agtcctttac aagccaaata aatgtgtcga tgttcctaaa    2493
aaaaaaaaaa aaaacggtcc gcggccgccc tttagtgagg gttaatttaa atcgtacgtc    2553
gcgattaatt aaccgcggta ccttctgagg cggaaagaac cagccggatc cctcgaggga    2613
tccagacatg ataaa                                                     2628
```

<210> SEQ ID NO 48
<211> LENGTH: 267
<212> TYPE: PRT
<213> ORGANISM: Rattus norvegicus (GenBank Accession No. AB071986)

<400> SEQUENCE: 48

```
Met Asn Met Ser Val Leu Thr Leu Gln Glu Tyr Glu Phe Glu Lys Gln
 1               5                  10                  15

Phe Asn Glu Asn Glu Ala Ile Gln Trp Met Gln Glu Asn Trp Lys Lys
             20                  25                  30

Ser Phe Leu Phe Ser Ala Leu Tyr Ala Ala Phe Ile Phe Gly Gly Arg
         35                  40                  45

His Leu Met Asn Lys Arg Ala Lys Phe Glu Leu Arg Lys Pro Leu Val
     50                  55                  60

Leu Trp Ser Leu Thr Leu Ala Val Phe Ser Ile Phe Gly Ala Leu Arg
 65                  70                  75                  80

Thr Gly Ala Tyr Met Leu Tyr Ile Leu Met Thr Lys Gly Leu Lys Gln
                 85                  90                  95

Ser Val Cys Asp Gln Ser Phe Tyr Asn Gly Pro Val Ser Lys Phe Trp
            100                 105                 110

Ala Tyr Ala Phe Val Leu Ser Lys Ala Pro Glu Leu Gly Asp Thr Ile
        115                 120                 125

Phe Ile Ile Leu Arg Lys Gln Lys Leu Ile Phe Leu His Trp Tyr His
    130                 135                 140
```

-continued

```
His Ile Thr Val Leu Leu Tyr Ser Trp Tyr Ser Tyr Lys Asp Met Val
145                 150                 155                 160

Ala Gly Gly Gly Trp Phe Met Thr Met Asn Tyr Gly Val His Ala Val
                165                 170                 175

Met Tyr Ser Tyr Tyr Ala Leu Arg Ala Ala Gly Phe Arg Val Ser Arg
            180                 185                 190

Lys Phe Ala Met Phe Ile Thr Leu Ser Gln Ile Thr Gln Met Leu Met
        195                 200                 205

Gly Cys Val Ile Asn Tyr Leu Val Phe Asn Trp Met Gln His Asp Asn
        210                 215                 220

Asp Gln Cys Tyr Ser His Phe Gln Asn Ile Phe Trp Ser Ser Leu Met
225                 230                 235                 240

Tyr Leu Ser Tyr Leu Leu Leu Phe Cys His Phe Phe Glu Ala Tyr
                245                 250                 255

Ile Gly Lys Val Lys Lys Ala Thr Lys Ala Glu
                260                 265
```

PRODUCTION OF γ-LINOLENIC ACID IN OLEAGINOUS YEAST

This application claims the benefit of U.S. Provisional Application No. 60/600,270, filed Aug. 10, 2004.

FIELD OF THE INVENTION

This invention is in the field of biotechnology. More specifically, this invention pertains to the production of γ-linolenic acid in oleaginous yeast.

BACKGROUND OF THE INVENTION

Gamma-linolenic acid (GLA; γ-linolenic acid; cis-6, 9, 12-octadecatrienoic acid) is an important intermediate in the biosynthesis of biologically active prostaglandin from linoleic acid (LA). Additionally, GLA is recognized as an essential ω-6 polyunsaturated fatty acid (PUFA) having tremendous clinical and pharmaceutical value. For example, GLA has been shown to reduce increases in blood pressure associated with stress and to improve performance on arithmetic tests. GLA and dihomo-γ-linolenic acid (DGLA, another ω-6 PUFA) have been shown to inhibit platelet aggregation, cause vasodilation, lower cholesterol levels and inhibit proliferation of vessel wall smooth muscle and fibrous tissue (Brenner et al., *Adv. Exp. Med. Biol.* 83:85-101 (1976)). Administration of GLA or DGLA, alone or in combination with eicosapentaenoic acid (EPA, an ω-3 PUFA), has been shown to reduce or prevent gastrointestinal bleeding and other side effects caused by non-steroidal anti-inflammatory drugs (U.S. Pat. No. 4,666,701). Further, GLA and DGLA have been shown to prevent or treat endometriosis and premenstrual syndrome (U.S. Pat. No. 4,758,592) and to treat myalgic encephalomyelitis and chronic fatigue after viral infections (U.S. Pat. No. 5,116,871). Additionally, GLA is also used in products relating to functional foods (nutriceuticals), infant nutrition, bulk nutrition, cosmetics and animal health.

Although seeds of many plants contain GLA, the most common commercial sources of GLA are evening primrose (*Oenothera biennis* L.; containing 5-9% GLA of total seed oil), black currant (*Ribes nigrum*; containing 14% GLA of total seed oil) and borage (*Borago officinalis* L.; containing 17-25% GLA from a total seed oil content of 28-38%) (Simon, J. E. et al., *In Advances In New Crops*; Janick, J. and J. E. Simon, Eds.; Timber: Portland, Oreg. (1990); p 528). There are several disadvantages associated with production of GLA from these sources, however. First, plant oils tend to have highly heterogeneous oil compositions that can require extensive purification to separate or enrich one or more of the desired PUFAs. Natural sources are also subject to uncontrollable fluctuations in availability (e.g., due to weather or disease); and, crops that produce PUFAs often are not competitive economically with hybrid crops developed for food production. Specific challenges associated with large-scale commercial production of borage are encountered because of the plants' indeterminate vegetative growth, lack of concentrated flowering and seed set, non-uniform seed maturation, susceptibility to a wide range of insects and disease pests, and poor ability to compete with weeds.

To overcome these problems, microorganisms have been investigated as an alternative source of GLA and other PUFAs. Specifically, many microorganisms (including algae, bacteria, molds and yeast) can synthesize oils in the ordinary course of cellular metabolism. Thus, oil production involves cultivating the microorganism in a suitable culture medium to allow for oil synthesis, followed by separation of the microorganism from the fermentation medium and treatment for recovery of the intracellular oil. Microbial production of GLA has been investigated, although these efforts have been minimal in comparison to the work focused on the microbial production of longer-chain PUFAs such as arachidonic acid (ARA), EPA and docosahexaenoic acid (DHA). Some suitable strains have been proposed as perspective GLA producers, including *Mortierella ramanniana*, *Mucor* sp., *Cunninghamella japonica* and *Entomophthora exitalis*. Currently, however, only Japan is producing GLA commercially using the fungus *Mortierella* (Ratledge, C. *Trends Biotech.* 11:278-284 (1993)). Thus, there remains a need for an appropriate microbial system for economical production of commercial quantities of GLA.

One class or microorganisms that has not been previously examined as a production platform for PUFAs such as GLA are the oleaginous yeast. These organisms can accumulate oil up to 80% of their dry cell weight. The technology for growing oleaginous yeast with high oil content is well developed (for example, see EP 0 005 277B1; Ratledge, C., *Prog. Ind. Microbiol.* 16:119-206 (1982)) and may offer a cost advantage compared to commercial micro-algae fermentation for production of PUFAs. Whole yeast cells may also represent a convenient way of encapsulating PUFA-enriched oils for use in functional foods and animal feed supplements.

Despite the advantages noted above, oleaginous yeast are naturally deficient in PUFAs, since naturally produced PUFAs in these organisms are limited to 18:2 acids (and, less commonly, 18:3 acids). Thus, the problem to be solved is to develop an oleaginous yeast that accumulates oils enriched in GLA. Toward this end, it is necessary to introduce desaturases that allow for the synthesis and accumulation of GLA in oleaginous yeast. Although advances in the art of genetic engineering have been made, such techniques have not been developed or optimized for oleaginous yeast; and, one must overcome problems associated with the use of these particular host organisms for the production of GLA.

Applicants have solved the stated problem by engineering strains of *Yarrowia lipolytica* that are capable of producing over 25% and 34% GLA in the total lipids, respectively. Additional metabolic engineering and fermentation methods are provided to further enhance GLA productivity in oleaginous yeast.

SUMMARY OF THE INVENTION

The present invention provides methods for the expression of enzymes comprising a γ-linolenic acid (GLA) biosynthetic pathway in an oleaginous yeast host for the production of γ-linolenic acid. Accordingly the invention provides A method for producing γ-linolenic acid comprising:

a) providing an oleaginous yeast comprising:
  i) at least one genetic construct encoding a polypeptide having a Δ6 desaturase activity;
  ii) at least one genetic construct encoding a polypeptide having a Δ12 desaturase activity; and,
  iii) a source of desaturase substrate selected from the group consisting of oleic acid and linoleic acid;
b) growing the yeast of step (a) in the presence of a fermentable carbon source whereby at least about 15% γ-linolenic acid in the total lipids is produced; and
c) optionally recovering the γ-linolenic acid.

Additionally the method makes use of a host cell optionally comprising a) at least one genetic construct encoding Δ9 desaturase polypeptide; b) at least one genetic construct encoding $C_{14/16}$ elongase polypeptide; and, c) at least one genetic construct encoding $C_{16/18}$ elongase polypeptide. Host cells preferred in the present invention are strains of *Yarrowia lipolytica*.

In a preferred embodiment the invention provides a method for producing γ-linolenic acid comprising:

a) providing a Yarrowia lipolytica comprising:
  i) at least one genetic construct encoding a polypeptide having a Δ6 desaturase activity;
  ii) at least one genetic construct encoding a polypeptide having a Δ12 desaturase activity; and,
  iii) a source of desaturase substrate selected from the group consisting of: oleic acid and linoleic acid;
  wherein the at least one genetic construct encoding a polypeptide having a Δ6 desaturase activity and the at least one genetic construct encoding a polypeptide having a Δ12 desaturase activity are in multicopy and are integrated into a genetic locus selected from the group consisting of the zeta loci, the Ura3 loci, the Leu 2 loci, the Lys5 loci, the Aco2 loci, the Pox3 loci, the Lip1 loci and the Lip2 loci of the *Yarrowia lipolytica*, and
  wherein the at least one genetic construct encoding a polypeptide having a Δ6 desaturase activity and the at least one genetic construct encoding a polypeptide having a Δ12 desaturase activity are under the control of a strong promoter isolated from genes selected from the group consisting of: alcohol dehydrogenase, glyceraldehyde-3-phosphate-dehydrogenase, phosphoglycerate mutase, fructose-bisphosphate aldolase, glycerol-3-phosphate o-acyltransferase, phosphoglucose-isomerase, phosphoglycerate kinase, acid phosphatase, lactase, metallothionein and glucoamylase;

b) growing the *Yarrowia lipolytica* of step (a) in the presence of a fermentable carbon source whereby at least about 15% γ-linolenic acid in the total lipids is produced; and, c) optionally recovering the γ-linolenic acid.

In another embodiment the invention provides a production host cell for the production of γ-linolenic acid comprising:

a) a background *Yarrowia* sp. comprising:
  i) at least one genetic construct encoding Δ12 desaturase polypeptide; and,
  ii) at least one genetic construct encoding Δ6 desaturase peptide;

wherein at least one of said genetic constructs of (i) and (ii) is over-expressed and whereby at least about 15% γ-linolenic acid in the total lipids is produced.

BRIEF DESCRIPTION OF THE DRAWINGS AND SEQUENCE DESCRIPTIONS

Figure 3:
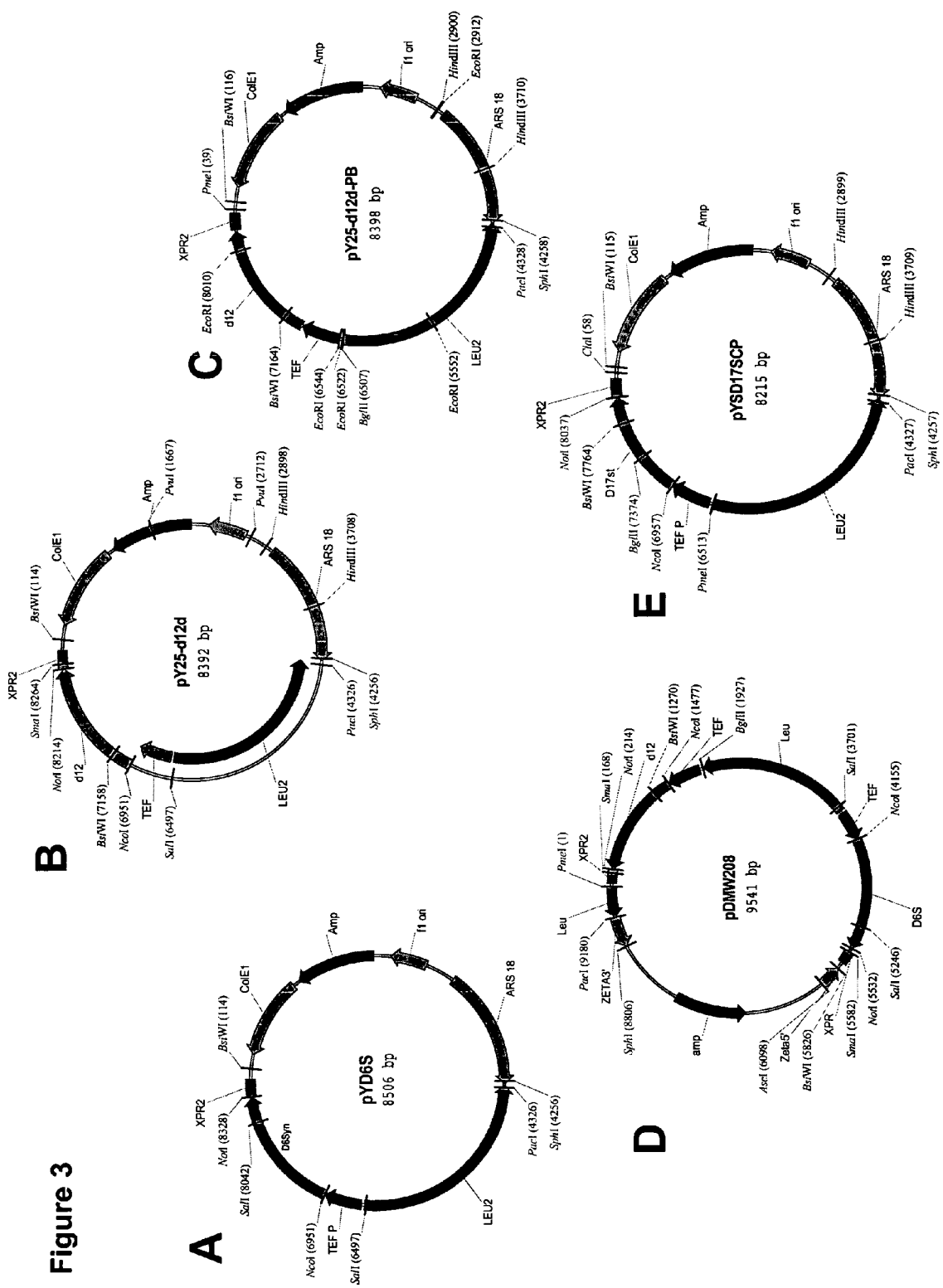

FIG. 3 provides plasmid maps for the following: (A) pYD6S; (B) pY25-d12d; (C) pY25-d12d-PB; (D) pDMW208; and (E) pYSD17SCP.

Figure 4:
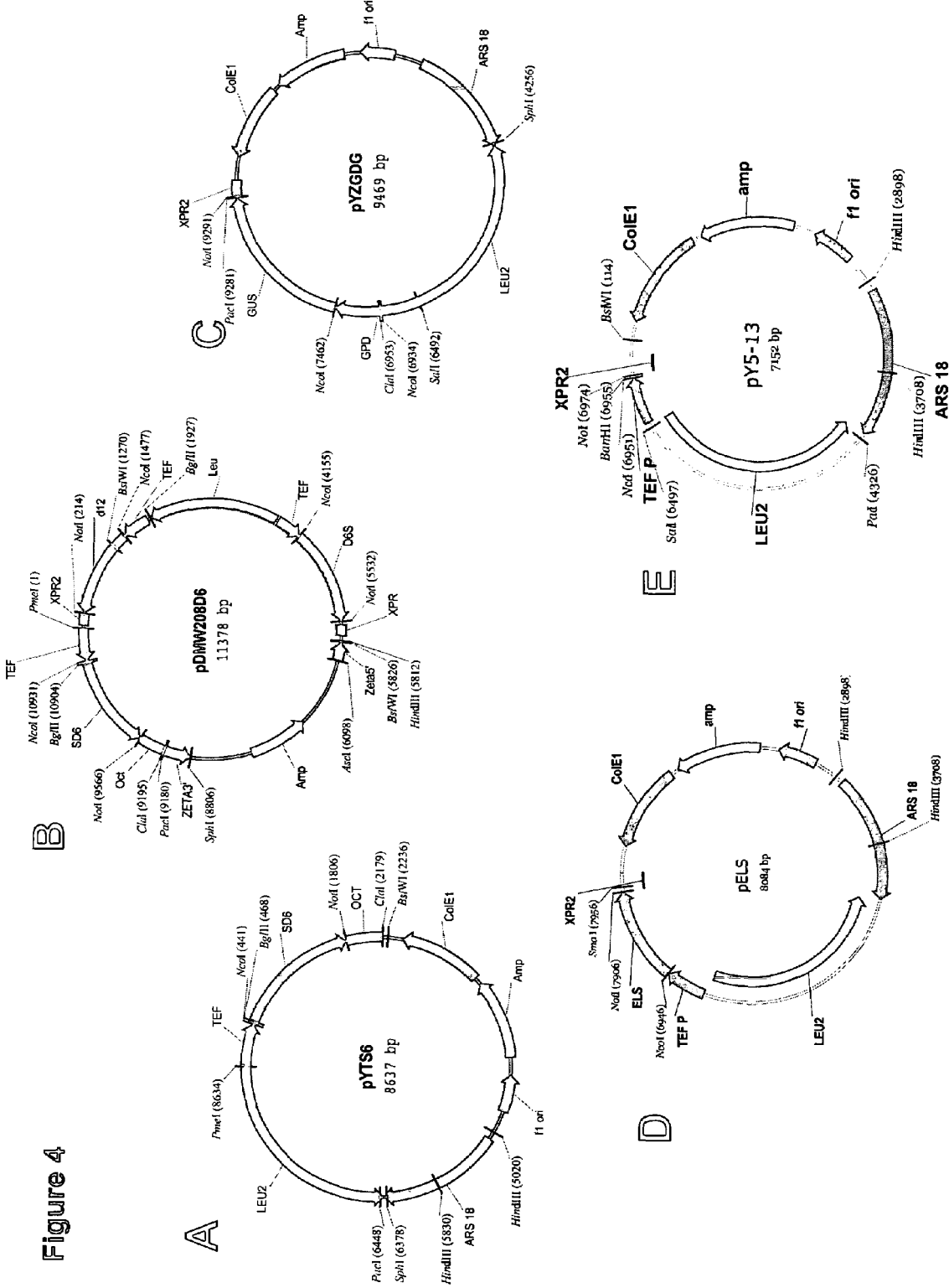

FIG. 4 provides plasmid maps for the following: (A) pYTS6; (B) pDMW208D6; (C) PYZGDG; (D) pELS; and (E) pY5-13.

Figure 5:
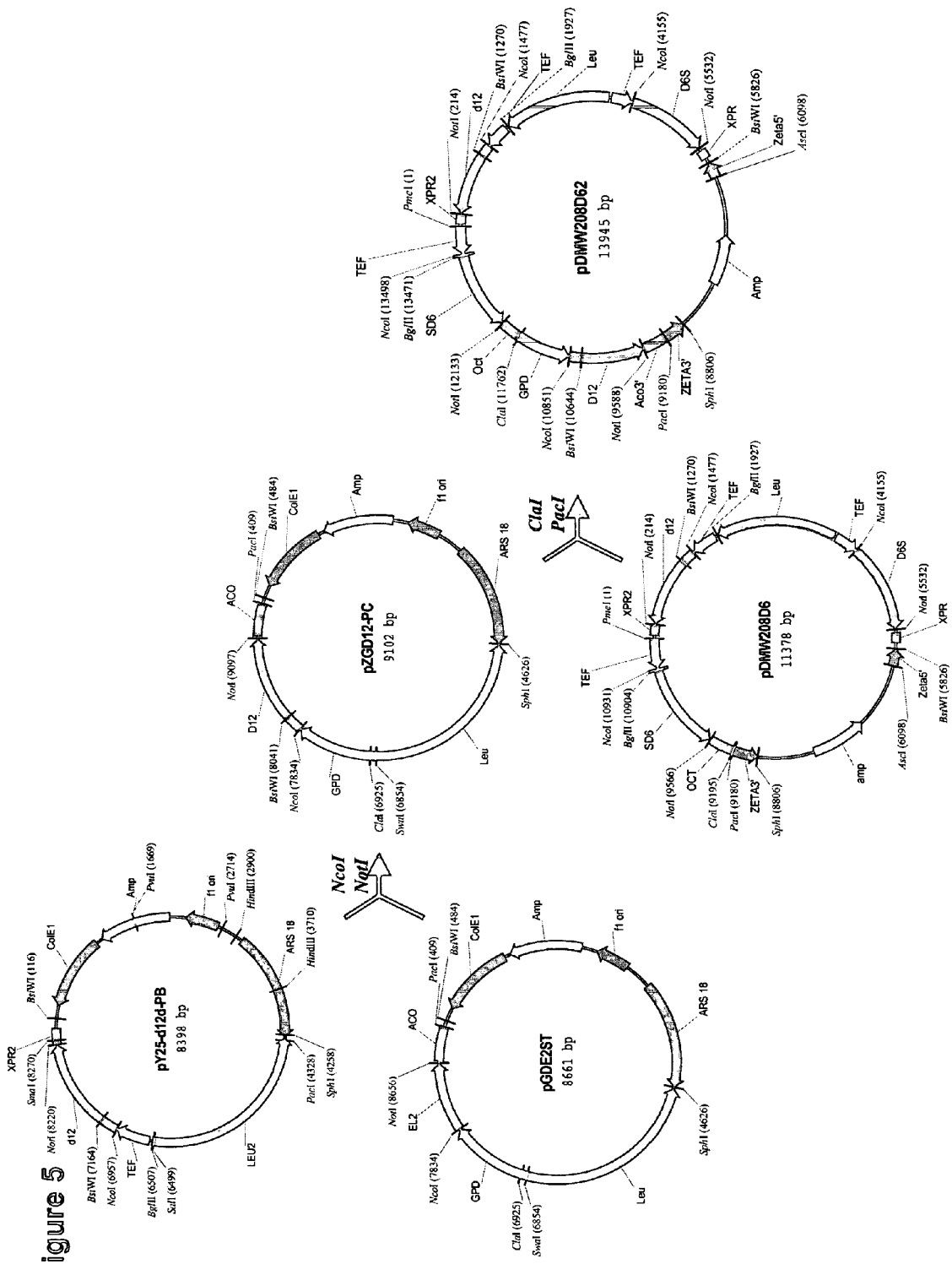

FIG. 5 illustrates the construction of plasmid vector pDMW208D62 for GLA expression in *Yarrowia lipolytica*.

FIG. 6A, 6B and 6C are chromatograms illustrating the production of GLA in wildtype *Y. lipolytica*, *Y. lipolytica* transformed with plasmid pDMW208 and *Y. lipolytica* transformed with plasmid pDMW208D62, respectively.

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—The Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-4 correspond to primers YL127, YL128, YL129 and YL130, respectively, used for amplification of the zeta regions of *Y. lipolytica*.

SEQ ID NO:5 is a 265 bp 5'-sequence from the *Y. lipolytica* zeta region; in contrast, SEQ ID NO:6 is a 359 bp 3'-sequence from the *Y. lipolytica* zeta region. Together, these sequences are useful to direct integration of expression cassettes into the zeta loci of the *Yarrowia* genome.

SEQ ID NO:7 is the DNA sequence of the synthetic Δ6 desaturase gene codon-optimized for expression in *Y. lipolytica*, while SEQ ID NO:8 is the corresponding amino acid sequence.

SEQ ID NO:9 is the DNA sequence of a ~1.95 kB fragment comprising the synthetic Δ6 desaturase gene codon-optimized for expression in *Y. lipolytica*, flanked by a TEF promoter and an XPR terminator.

SEQ ID NOs:10 and 11 correspond to primers YL238 and YL239, respectively, used for site-directed mutagenesis to generate pDMW200-B.

SEQ ID NOs:12-15 correspond to primers YL242, YL243, YL240 and YL241, respectively, used for site-directed mutagenesis to generate pY25-d12d-PB.

SEQ ID NO:16 is the DNA sequence of a ~1.9 kB fragment comprising the *Y. lipolytica* Δ12 desaturase gene flanked by a TEF promoter and an XPR terminator.

SEQ ID NO:17 is the DNA sequence of GLA expression vector pDMW208.

SEQ ID NOs:18 and 19 correspond to primers YL253 and YL254, respectively, used for amplification of the *Saprolegnia diclina* Δ6 desaturase.

SEQ ID NOs:20 and 21 correspond to primers YL293 and YL317, respectively, used for amplification of the OCT terminator.

SEQ ID NO:22 is the DNA sequence of a ~2.2 kB fragment comprising the *S. diclina* Δ6 desaturase gene flanked by the TEF promoter and OCT terminator.

SEQ ID NOs:23-30 correspond to primers YL226, YL227, YL61, YL62, YL230, YL231, YL228 and YL229, respectively, used for site-directed mutagenesis to generate pYZDE1SB-CN.

SEQ ID NOs:31 and 32 correspond to primers YL179 and YL179A, respectively, used for amplification of the *Thraustochytrium aureum* T7091 elongase gene.

SEQ ID NOs:33-36 correspond to primers YL77, YL78, YL322 and YL323, respectively, used for site-directed mutagenesis to generate pGDE2S-PC.

SEQ ID NOs:37 and 38 correspond to primers YL325 and YL326, respectively, used for amplification of the ACO terminator.

SEQ ID NO:39 is the DNA sequence of a ~2.6 kB fragment comprising a Δ12 desaturase flanked by the GPD promoter and an Aco terminator.

SEQ ID NO:40 is the DNA sequence of GLA expression vector pDMW208D62.

SEQ ID NO:41 corresponds to the codon-optimized translation initiation site for genes optimally expressed in *Yarrowia* sp.

SEQ ID NO:42 comprises the FBA promoter.

SEQ ID NO:43 is the DNA sequence of the FBAIN promoter.

SEQ ID NO:44 is the DNA sequence of the *Fusarium moniliforme* Δ12 desaturase, while SEQ ID NO:45 is the corresponding amino acid sequence.

SEQ ID NO:46 is the DNA sequence of the synthetic $C_{16/18}$ elongase gene derived from *Rattus norvegicus* and codon-optimized for expression in *Yarrowia lipolytica*. SEQ ID NO:47 is the DNA sequence of the native *Rattus norvegicus* $C_{16/18}$ elongase gene (GenBank Accession No. AB071986), while SEQ ID NO:48 is the corresponding amino acid sequence.

DETAILED DESCRIPTION OF THE INVENTION

The following patents, patent applications, and patent publications cited herein are incorporated by reference in their entirety; commonly owned U.S. Ser. Nos. 10/840,478, 10/840,579 10/840,325, 10/869,630, 10/985,691, 10/987,548, U.S. Provisional Patent Application No. 60/610,060 and U.S. Provisional Patent Application No. 60/624812.

In accordance with the subject invention, Applicants provide methods for the production of γ-linolenic acid (GLA) in oleaginous yeasts and production hosts useful in said methods. Accumulation of this particular polyunsaturated fatty acid (PUFA) is accomplished by introduction of a functional ω-6 fatty acid biosynthetic pathway comprising proteins that encode Δ12 desaturase (responsible for conversion of oleic acid to linoleic acid (LA)) and Δ6 desaturase (responsible for conversion of LA to GLA) activities into oleaginous yeast hosts for recombinant expression. Thus, this disclosure demonstrates that oleaginous yeast can be engineered to enable commercial production of GLA and derivatives thereof. Methods of production are also claimed.

The subject invention finds many applications. PUFAs, or derivatives thereof, made by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products, and may find use as anti-inflammatory or cholesterol lowering agents. Optionally, the compositions may be used for pharmaceutical use (human or veterinary). In this case, the PUFAs are generally administered orally but can be administered by any route by which they may be successfully absorbed, e.g., parenterally (e.g., subcutaneously, intramuscularly or intravenously), rectally, vaginally or topically (e.g., as a skin ointment or lotion).

Supplementation of humans or animals with PUFAs produced by recombinant means can result in increased levels of the added PUFAs, as well as their metabolic progeny. For example, treatment with GLA can result not only in increased levels of GLA, but also downstream products of GLA such as prostaglandins. Complex regulatory mechanisms can make it desirable to combine various PUFAs, or add different conjugates of PUFAs, in order to prevent, control or overcome such mechanisms to achieve the desired levels of specific PUFAs in an individual.

DEFINITIONS

In this disclosure, a number of terms and abbreviations are used. The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

The term "fatty acids" refers to long-chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms and Y is the number of double bonds. Information relating to the differentiation between "saturated fatty acids" versus "unsaturated fatty acids", "monounsaturated fatty acids" versus "polyunsaturated fatty acids" (or "PUFAs"), and "omega-6 fatty acids" (ω-6 or n-6) versus "omega -3 fatty acids" (ω-3 or n-3) are provided in U.S. Ser. No. 10/840,579.

Nomenclature used to describe PUFAs in the present disclosure is shown below in Table 1. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of ω-3 and ω-6 fatty acids and their precursors, the abbreviations that will be used throughout the specification and each compounds' chemical name.

TABLE 1

Nomenclature of Polyunsaturated Fatty Acids And Precursors

| Common Name | Abbreviation | Chemical Name | Shorthand Notation |
|---|---|---|---|
| Myristic | — | tetradecanoic | 14:0 |
| Palmitate | — | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9, 12-octadecadienoic; CAS RN #60-33-3 | 18:2 ω-6 |
| γ-Linolenic | GLA | cis-6, 9, 12-octadecatrienoic; CAS RN #506-26-3 | 18:3 ω-6 |
| Eicosadienoic | EDA | cis-11, 14-eicosadienoic | 20:2 ω-6 |
| Dihomo-γ-Linolenic | DGLA | cis-8, 11, 14-eicosatrienoic | 20:3 ω-6 |
| Arachidonic | ARA | cis-5, 8, 11, 14-eicosatetraenoic | 20:4 ω-6 |
| α-Linolenic | ALA | cis-9, 12, 15-octadecatrienoic | 18:3 ω-3 |
| Stearidonic | STA | cis-6, 9, 12, 15-octadecatetraenoic | 18:4 ω-3 |
| Eicosatrienoic | ETrA | cis-11, 14, 17-eicosatrienoic | 20:3 ω-3 |
| Eicosa-tetraenoic | ETA | cis-8, 11, 14, 17-eicosatetraenoic | 20:4 ω-3 |
| Eicosa-pentaenoic | EPA | cis-5, 8, 11, 14, 17-eicosapentaenoic | 20:5 ω-3 |
| Docosa-pentaenoic | DPA | cis-7, 10, 13, 16, 19-docosapentaenoic | 22:5 ω-3 |
| Docosa-hexaenoic | DHA | cis-4, 7, 10, 13, 16, 19-docosahexaenoic | 22:6 ω-3 |

The term "high-level GLA production" refers to production of at least about 15% GLA in the total lipids of the microbial host, preferably at least about 20% GLA in the total lipids, more preferably at least about 30% GLA in the total lipids, more preferably at least about 40% GLA in the total lipids and most preferably at least about 50% GLA in the total lipids. The structural form of GLA is not limiting; thus, for example, GLA may exist in the total lipids as free fatty acids or in esterified forms such as acylglycerols, phospholipids, sulfolipids or glycolipids.

"Percent (%) GLA in the total lipids" refers to the percent of GLA relative to the total fatty acids in the total lipid and oil fractions. The term "total lipid fraction" or "lipid fraction" both refer to the sum of all lipids (i.e., neutral and polar) within an oleaginous organism, thus including those lipids that are located in the phosphatidylcholine fraction, phosphatidyletanolamine fraction and triacylglycerol (TAG or oil) fraction. However, the terms "lipid" and "oil" will be used interchangeably throughout the specification herein.

"Microbial oils" or "single cell oils" are those oils naturally produced by microorganisms (e.g., algae, oleaginous yeasts and filamentous fungi) during their lifespan. The term "oil" refers to a lipid substance that is liquid at 25° C. and usually polyunsaturated. In contrast, the term "fat" refers to a lipid substance that is solid at 25° C. and usually saturated.

Figure 1:
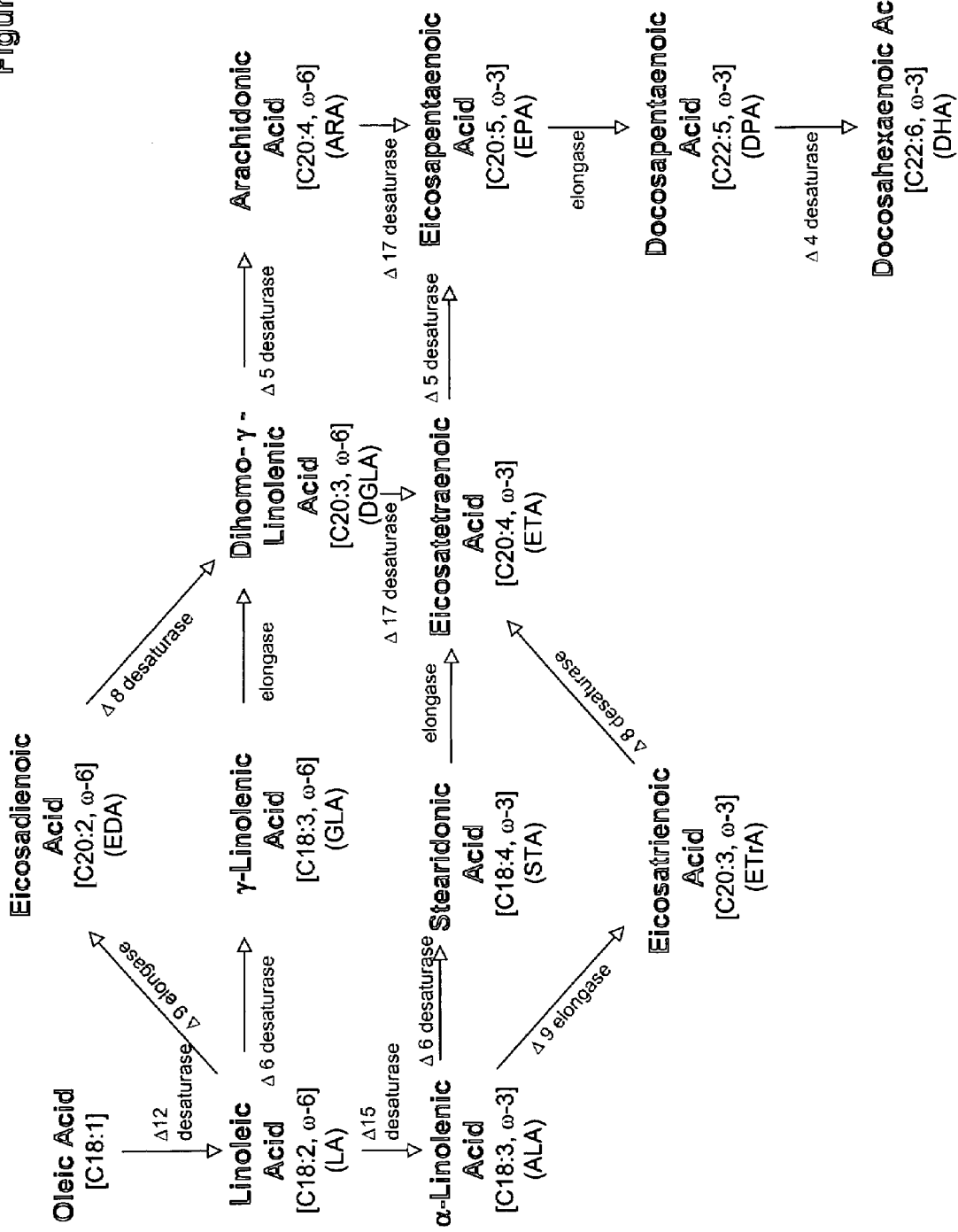
FIG. 1 illustrates the ω-3/ω-6 fatty acid biosynthetic pathway.

The term "PUFA biosynthetic pathway enzyme" refers to any of the following enzymes (and genes which encode said enzymes) associated with the biosynthesis of a PUFA, including: a $\Delta 4$ desaturase, a $\Delta 5$ desaturase, a $\Delta 6$ desaturase, a $\Delta 8$ desaturase, a $\Delta 9$ desaturase, a $\Delta 12$ desaturase, a $\Delta 15$ desaturase, a $\Delta 17$ desaturase, a $\Delta 9$ elongase, a $C_{14/16}$ elongase, a $C_{16/18}$ elongase, a $C_{18/20}$ elongase and/or a $C_{20/22}$ elongase. Similarly, the term "ω-3/ω-6 fatty acid biosynthetic pathway" refers to a set of genes which, when expressed under the appropriate conditions encode enzymes that catalyze the production of either or both ω-3 and ω-6 fatty acids. Typically the genes involved in the ω-3/ω-6 fatty acid biosynthetic pathway encode some or all of the following enzymes: $\Delta 12$ desaturase, $\Delta 6$ desaturase, $\Delta 5$ desaturase, $\Delta 17$ desaturase, $\Delta 15$ desaturase, $\Delta 8$ desaturase, $\Delta 4$ desaturase, a $\Delta 9$ elongase, a $C_{18/20}$ elongase and/or a $C_{20/22}$ elongase. A representative pathway is illustrated in FIG. 1, providing for the conversion of myristic acid through various intermediates to DHA, which demonstrates how both (ω-3 and ω-6 fatty acids may be produced from a common source. The pathway is naturally divided into two portions where one portion will generate ω-3 fatty acids and the other portion, only ω-6 fatty acids. That portion that only generates ω-3 fatty acids will be referred to herein as the ω-3 fatty acid biosynthetic pathway, whereas that portion that generates only ω-6 fatty acids will be referred to herein as the ω-6 fatty acid biosynthetic pathway.

The term "functional" as used herein in context with the ω-3/ω-6 fatty acid biosynthetic pathway (or a portion thereof) means that some (or all of) the genes in the pathway express active enzymes, resulting in in vivo catalysis or substrate conversion. It should be understood that "ω-3/ω-6 fatty acid biosynthetic pathway" or "functional ω-3/ω-6 fatty acid biosynthetic pathway" does not imply that all the genes listed in the above paragraph are required, as a number of fatty acid products will only require the expression of a subset of the genes of this pathway.

The term "GLA biosynthetic pathway" refers to genes encoding enzymes providing for the conversion of oleic acid through GLA (i.e., $\Delta 12$ desaturase and $\Delta 6$ desaturase).

The term "desaturase" refers to a polypeptide that can desaturate one or more fatty acids to produce a mono- or polyunsaturated fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are: $\Delta 12$ desaturases that desaturate a fatty acid between the $12^{th}$ and $13^{th}$ carbon atom numbered from the carboxyl-terminal end of the molecule and which, for example, catalyze the conversion of oleic acid to LA; and, $\Delta 6$ desaturases that catalyze the conversion of LA to GLA and/or ALA to STA. Other PUFA desaturases include: 1.) $\Delta 17$ desaturases that catalyze the conversion of ARA to EPA and DGLA to ETA; 2.) $\Delta 5$ desaturases that catalyze the conversion of DGLA to ARA and/or ETA to EPA; 3.) $\Delta 4$ desaturases that catalyze the conversion of DPA to DHA; 4.) $\Delta 15$ desaturases that catalyze the conversion of LA to ALA; 5.) $\Delta 9$ desaturases that catalyze the conversion of palmitate to palmitoleic acid (16:1) and/or stearate to oleic acid (18:1); and 6.) $\Delta 8$ desaturases that catalyze the conversion of EDA to DGLA and ETrA to ETA.

The term "elongase system" refers to a suite of four enzymes that are responsible for elongation of a fatty acid carbon chain to produce a fatty acid that is 2 carbons longer than the fatty acid substrate that the elongase system acts upon. More specifically, the process of elongation occurs in association with fatty acid synthase, whereby CoA is the acyl carrier (Lassner et al., *The Plant Cell* 8:281-292 (1996)). In the first step, which has been found to be both substrate-specific and also rate-limiting, malonyl-CoA is condensed with a long-chain acyl-CoA to yield $CO_2$ and a β-ketoacyl-CoA (where the acyl moiety has been elongated by two carbon atoms). Examples of reactions catalyzed by elongase systems are the conversion of GLA to DGLA, LA to EDA, ALA to ETrA, STA to ETA and EPA to DPA.

For the purposes herein, an enzyme catalyzing the first condensation reaction (i.e., conversion of malonyl-CoA to β-ketoacyl-CoA) will be referred to generically as an "elongase". In general, the substrate selectivity of elongases is somewhat broad but segregated by both chain length and the degree of unsaturation. Accordingly, elongases can have different specificities. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase will utilize a $C_{18}$ substrate (e.g., GLA, STA) and a $C_{20/22}$ elongase will utilize a $C_{20}$ substrate (e.g., EPA). In like manner, a $\Delta 9$ elongase is able to catalyze the conversion of LA and ALA to EDA and ETrA, respectively. It is important to note that some elongases have broad specificity and thus a single enzyme may be capable of catalyzing several elongase reactions (e.g., thereby acting as both a $C_{16/18}$ elongase and a $C_{18/20}$ elongase).

The terms "conversion efficiency" and "percent substrate conversion" refer to the efficiency by which a particular enzyme (e.g., a desaturase or elongase) can convert substrate to product. The conversion efficiency is measured according to the following formula: ([product]/[substrate+product])*100, where 'product' includes the immediate product and all products in the pathway derived from it.

The term "oleaginous" refers to those organisms that tend to store their energy source in the form of lipid (Weete, In: Fungal Lipid Biochemistry, $2^{nd}$ Ed., Plenum, 1980). Generally, the cellular PUFA content of these microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419-25 (1991)).

The term "oleaginous yeast" refers to those microorganisms classified as yeast that can accumulate at least 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces*.

The term "fermentable carbon source" means a carbon source that a microorganism will metabolize to derive energy. Typical carbon sources of the invention include, but are not limited to: monosaccharides, oligosaccharides, polysaccharides, alkanes, fatty acids, esters of fatty acids, monoglycerides, diglycerides, triglycerides, carbon dioxide, methanol, formaldehyde, formate and carbon-containing amines.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993)). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of microbial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "complementary" is used to describe the relationship between nucleotide bases that are capable of hybridizing to one another. For example, with respect to DNA, adenosine is complementary to thymine and cytosine is complementary to guanine.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within or downstream (3' non-coding sequences) of a coding sequence and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The terms "3' non-coding sequences" or "transcription terminator" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence or the coding sequence. "Functional RNA" refers to antisense RNA, ribozyme RNA or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragments of the invention. Expression may also refer to translation of mRNA into a polypeptide.

"Transformation" refers to the transfer of a nucleic acid molecule into a host organism, resulting in genetically stable inheritance. The nucleic acid molecule may be a plasmid that replicates autonomously, for example; or, it may integrate into the genome of the host organism. Host organisms containing the transformed nucleic acid fragments are referred to as "transgenic" or "recombinant" or "transformed" organisms.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction that is capable of introducing a promoter fragment and DNA sequence for a selected gene product along with appropriate 3' untranslated sequence into a cell. "Expression cassette" refers to a specific vector containing a foreign gene and having elements in addition to the foreign gene that allow for enhanced expression of that gene in a foreign host.

The term "homologous recombination" refers to the exchange of DNA fragments between two DNA molecules (during cross over). The fragments that are exchanged are flanked by sites of identical nucleotide sequences between the two DNA molecules (i.e., "regions of homology"). The term "regions of homology" refer to stretches of nucleotide sequence on nucleic acid fragments that participate in homologous recombination that have homology to each other. Effective homologous recombination will generally take place where these regions of homology are at least about 10 bp in length where at least about 50 bp in length is preferred. Typically fragments that are intended for recombination contain at least two regions of homology where targeted gene disruption or replacement is desired.

Standard recombinant DNA and molecular cloning techniques used herein are well known in the art and are described by Sambrook, J., Fritsch, E. F. and Maniatis, T., *Molecular Cloning: A Laboratory Manual*, 2$^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience (1987).

Microbial Biosynthesis of Fatty Acids

The process of de novo synthesis of palmitate (16:0) in oleaginous microorganisms is described in Ser. No. 10/840,579. This fatty acid is the precursor of longer-chain saturated and unsaturated fatty acid derivates, which are formed through the action of elongases and desaturases. For example, palmitate is converted to its unsaturated derivative [palmitoleic acid (16:1)] by the action of a Δ9 desaturase; alternatively, palmitate is elongated by a $C_{16/18}$ elongase to form stearic acid (18:0), which can be converted to its unsaturated derivative by a Δ9 desaturase to thereby yield oleic acid (18:1). Since the primary fate of palmitate is elongation, however, it is concluded that $C_{16/18}$ elongases play an important role in determining overall carbon flux into the fatty acid biosynthetic pathway since they control the amount of stearic acid produced in the microbial cell.

Triacylglycerols or "TAGs" (the primary storage unit for fatty acids) are formed by the esterification of two molecules of acyl-CoA to glycerol-3-phosphate to yield 1,2-diacylglycerol phosphate (commonly identified as phosphatidic acid (PA)) (and CoA as a by-product)). The phosphate is then removed, by phosphatidic acid phosphatase, to yield 1,2-diacylglycerol (DAG). Triacylglycerol is formed upon the addition of a third fatty acid to the sn-3 position of DAG by the action of a DAG transferase (e.g., phospholipid:diacylglycerol acyltransferase [PDAT] and diacylglycerol acyltransferase [DGAT1 or DGAT2]).

Biosynthesis of GLA, an ω-6 Fatty Acid

The metabolic process wherein oleic acid is converted to LA and then GLA requires desaturation of the molecule through the addition of double bonds. Specifically, oleic acid (18:1) is converted to LA (18:2; Formula I below), the first of the ω-6 fatty acids, by the activity of a Δ12 desaturase.

Formula I:

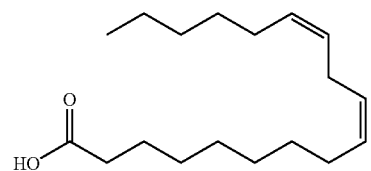

Then, LA is converted to GLA (Formula II below) by the activity of a Δ6 desaturase.

Formula II:

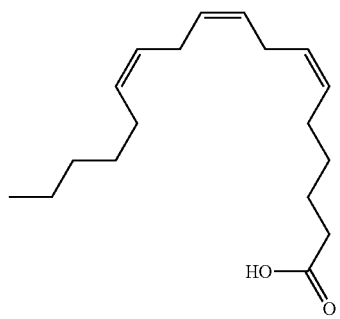

Thus, the construction of a *Yarrowia lipolytica* strain producing greater than 15% GLA in the total oil fraction, or more preferably greater than 20% GLA in the total oil fraction, or even more preferably greater than 30% GLA in the total oil fraction, or most preferably greater than 40-50% GLA in the total oil fraction requires at least the following genes: a Δ12 desaturase and a Δ6 desaturase. However, it may be desirable to additionally include a Δ9 desaturase, a $C_{14/16}$ elongase and/or a $C_{16/18}$ elongase in the host strain (infra).

A variety of other PUFAs can be produced using GLA as substrate. The complete ω-6 and ω-3 pathways for fatty acid biosynthesis are shown in FIG. 1. Specifically, GLA can be converted to DGLA by the activity of a $C_{18/20}$ elongase; and DGLA is subsequently converted to ARA by the activity of a Δ5 desaturase or ETA by the activity of a Δ17 desaturase. Downstream products may also include e.g., EPA, DPA and DHA, depending on the presence of additional desaturases and elongases with appropriate specificity.

Microbial Production of GLA

Microbial production of GLA and other PUFAs has several advantages over purification from natural plant sources. For example: (1) many microbes are known with greatly simplified oil compositions compared with those of higher organisms, making purification of desired components easier; (2) microbial production is not subject to fluctuations caused by external variables, such as weather and disease; (3) microbially produced oil is substantially free of contamination by environmental pollutants; and, (4) microbial oil production can be manipulated by controlling culture conditions, notably by providing particular substrates for microbially expressed enzymes, or by addition of compounds or genetic engineering approaches to suppress undesired biochemical pathways. With respect to the production of ω-3 and/or ω-6 fatty acids in particular (e.g., GLA), and TAGs containing those PUFAs, additional advantages are incurred since microbes can provide fatty acids in particular forms that may have specific uses; and, recombinant microbes provide the ability to alter the naturally occurring microbial fatty acid profile by providing new biosynthetic pathways in the host or by suppressing undesired pathways, thereby increasing levels of desired PUFAs or conjugated forms thereof and decreasing levels of undesired PUFAs.

Microbial Genes for GLA Production

Many microorganisms, including algae, bacteria, molds and yeast, can synthesize PUFAs and omega fatty acids in the ordinary course of cellular metabolism. Particularly well-studied are fungi including *Schizochytrium aggregatm*, species of the genus *Thraustochytrium* and *Morteriella alpina*. Additionally, many dinoflagellates (Dinophyceaae) naturally produce high concentrations of PUFAs. As such, a variety of genes involved in oil production have been identified through genetic means; and, the DNA sequences of some of the genes required for GLA biosynthesis (i.e., Δ12 and Δ6 desaturases) are publicly available (non-limiting examples are shown below in Table 2):

TABLE 2

Some Publicly Available Genes Involved In GLA Production

| Genbank Accession No. | Description |
| --- | --- |
| AY131238 | *Argania spinosa* Δ6 desaturase |
| Y055118 | *Echium pitardii* var. *pitardii* Δ6 desaturase |
| AY055117 | *Echium gentianoides* Δ6 desaturase |
| AF296076 | *Mucor rouxii* Δ6 desaturase |
| AF007561 | *Borago officinalis* Δ6 desaturase |
| L11421 | *Synechocystis* sp. Δ6 desaturase |
| NM_031344 | *Rattus norvegicus* Δ6 fatty acid desaturase |

TABLE 2-continued

Some Publicly Available Genes Involved In GLA Production

| Genbank Accession No. | Description |
| --- | --- |
| AF465283, AF465281, AF110510 | *Mortierella alpina* Δ6 fatty acid desaturase |
| AF465282 | *Mortierella isabellina* Δ6 fatty acid desaturase |
| AF419296 | *Pythium irregulare* Δ6 fatty acid desaturase |
| AB052086 | *Mucor circinelloides* D6d mRNA for Δ6 fatty acid desaturase |
| AJ250735 | *Ceratodon purpureus* mRNA for Δ6 fatty acid desaturase |
| AF126799 | *Homo sapiens* Δ6 fatty acid desaturase |
| AF126798 | *Mus musculus* Δ6 fatty acid desaturase |
| AF251842 | *Helianthus annuus* Δ12 fatty acid desaturase |
| AY165023 | *Phaeodactylum tricornutum* Δ12 fatty acid desaturase |
| AF343065 | *Calendula officinalis* Δ12 fatty acid desaturase FAD2 |
| AF417245 | *Mortieralla isabellina* M6-22 Δ12 fatty acid desaturase |
| AF417244 | *Mortierella alpina* ATCC #16266 Δ12 fatty acid desaturase gene |
| AB052087 | *Mucor circinelloides* D12d mRNA for Δ12 fatty acid desaturase |
| AAG36933 | *Emericella nidulans* oleate Δ12 desaturase |
| AF110509, AB020033 | *Mortierella alpina* Δ12 fatty acid desaturase mRNA |
| AAL13300 | *Mortierella alpina* Δ12 fatty acid desaturase |
| AF161219 | *Mucor rouxii* Δ12 desaturase mRNA |

Additionally, the patent literature provides many additional DNA sequences of genes (and/or details concerning several of the genes above and their methods of isolation) involved in PUFA production. See, for example: U.S. Pat. No. 5,968,809 and U.S. Patent Application No. 60/468,718 (Δ6 desaturases); WO 94/11516, U.S. Pat. No. 5,443,974, WO 03/099216, U.S. Patent Application No. 60/484,209 and U.S. patent application No.—(Δ12 desaturases).

Microbial Gene Selection

As is well known in the art, the particular functionalities required to be introduced into a host organism for production of a particular PUFA final product will depend on the host cell (and its native PUFA profile and/or desaturase/elongase profile), the availability of substrate and the desired end product (s). For GLA production from oleic acid, LA and GLA may both be produced in oleaginous yeast by introducing a Δ12 desaturase and a Δ6 desaturase and subsequent PUFA derivatives, including DGLA, ARA, STA, ETA, EPA, DPA and DHA, may also be produced if the host possesses endogenous or exogenous Δ4, Δ5, Δ15 and/or Δ17 desaturase activities and/or $C_{18/20}$ and/or $C_{20/22}$ activities). One skilled in the art will be able to identify various candidate genes encoding Δ12 desaturase and/or Δ6 desaturase activities, according to publicly available literature (e.g., GenBank), the patent literature and experimental analysis of microorganisms having the ability to produce PUFAs. The sequences may be derived from any source, e.g., isolated from a natural source (from bacteria, algae, fungi, plants, animals, etc.), produced via a semi-synthetic route or synthesized de novo. In some embodiments, manipulation of genes endogenous to the host is preferred; for other purposes, it is necessary to introduce heterologous genes.

Although the particular source of the desaturase gene introduced into the host is not critical to the present invention, considerations for choosing a specific polypeptide having desaturase activity include: 1.) the substrate specificity of the polypeptide; 2.) whether the polypeptide or a component thereof is a rate-limiting enzyme; 3.) whether the desaturase is essential for synthesis of a desired PUFA; and/or 4.) cofactors required by the polypeptide. The expressed polypeptide preferably has parameters compatible with the biochemical environment of its location in the host cell. For example, the polypeptide may have to compete for substrate with other enzymes in the host cell. Analyses of the $K_M$ and specific activity of the polypeptide are therefore considered in determining the suitability of a given polypeptide for modifying PUFA production, and specifically GLA production, in a given host cell. The polypeptide used in a particular host cell is one that can function under the biochemical conditions present in the intended host cell but otherwise can be any polypeptide having desaturase activity capable of converting a particular substrate into the desired PUFA.

Endogenous PUFA Genes

In some cases, the host organism in which it is desirable to produce GLA will possess endogenous genes encoding some PUFA biosynthetic pathway enzymes. For example, oleaginous yeast can typically produce 18:2 acids (and some have the additional capability of synthesizing 18:3 acids); thus, oleaginous yeast typically possess native Δ12 desaturase activity and may also have Δ15 desaturases. In some embodiments, therefore, expression of the native desaturase enzyme is preferred over a heterologous (or "foreign") enzyme since: 1.) the native enzyme is optimized for interaction with other enzymes and proteins within the cell; and 2.) heterologous genes are unlikely to share the same codon preference in the host organism.

In one embodiment of the present invention, *Yarrowia lipolytica* was selected as a host organism for production of GLA. This oleaginous yeast is able to synthesize 18:2 fatty acids (but not 18:3), as a result of an endogenous Δ12 fatty acid desaturase (contained within SEQ ID NO:16; see commonly owned U.S. Ser. No. 10/840,325).

Heterologous PUFA Genes

In many instances, the appropriate desaturases (and optionally, elongases) are not present in the host organism of choice to enable production of the desired PUFA products. Thus, it is necessary to introduce heterologous genes.

For the purposes of the present invention herein, it was desirable to demonstrate high-level production of GLA in an oleaginous host organism; and thus, a native Δ12 desaturase, a synthetic *Mortierella alpina* Δ6 desaturase codon-optimized for expression in *Yarrowia lipolytica* and a *Saprolegnia diclina* Δ6 desaturase were introduced into the host, *Y. lipolytica*. However, the specific enzymes (and genes encoding those enzymes) introduced into the host organism are by no means limiting to the invention herein.

If one desired to produce GLA, as demonstrated herein, it is clear that numerous other genes derived from different sources would be suitable to introduce Δ12 desaturase and Δ6 desaturase activity into the preferred microbial host. Thus, in one embodiment of the present invention, other DNAs that are substantially identical to the *Y. lipolytica* Δ12 desaturase, synthetically produced Δ6 desaturase (codon-optimized for expression in *Y. lipolytica*) and the *S. diclina* Δ6 desaturase also could be used for production of GLA in oleaginous yeast. By "substantially identical" is intended an amino acid sequence or nucleic acid sequence exhibiting in order of increasing preference at least 80%, 90% or 95% homology to the selected polypeptides, or nucleic acid sequences encoding the amino acid sequence. For polypeptides, the length of comparison sequences generally is at least 16 amino acids, preferably at least 20 amino acids, or most preferably 35 amino acids. For nucleic acids, the length of comparison sequences generally is at least 50 nucleotides, preferably at least 60 nucleotides, more preferably at least 75 nucleotides, and most preferably 110 nucleotides.

Homology typically is measured using sequence analysis software, wherein the term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215:403410 (1990)); 3.) DNASTAR (DNASTAR, Inc., Madison, Wis.); and 4.) the FASTA program incorporating the Smith-Waterman algorithm (W. R. Pearson, *Comput. Methods Genome Res.*, [Proc. Int. Symp.] (1994), Meeting Date 1992, 111-20. Suhai, Sandor, Ed. Plenum: New York, N.Y.). Within the context of this application it will be understood that where sequence analysis software is used for analysis, the results of the analysis will be based on the "default values" of the program referenced, unless otherwise specified. As used herein "default values" will mean any set of values or parameters that originally load with the software when first initialized. In general, such computer software matches similar sequences by assigning degrees of homology to various substitutions, deletions and other modifications.

Additionally, it will be appreciated by one of skill in the art that polypeptides may have amino acids conservatively substituted in a manner such that the function of the polypeptide is not altered or compromised. Polypeptides having the desaturase activities as described herein and possessing such conservative substitutions are considered within the scope of the present invention. Conservative substitutions typically include substitutions within the following groups: 1.) glycine and alanine; 2.) valine, isoleucine and leucine; 3.) aspartic acid, glutamic acid, asparagine and glutamine; 4.) serine and threonine; 5.) lysine and arginine; and 6.) phenylalanine and tyrosine. Substitutions may also be made on the basis of conserved hydrophobicity or hydrophilicity (Kyte and Doolittle, *J. Mol. Biol.* 157:105-132 (1982)), or on the basis of the ability to assume similar polypeptide secondary structure (Chou and Fasman, *Adv. Enzymol.* 47:45-148 (1978)).

One alternative Δ12 desaturase that is specifically contemplated for overexpression in *Yarrowia lipolytica* is that from *Fusarium moniliforme* (WO2005/047485; SEQ ID NOs:44 and 45 herein). And, in some cases, it may prove advantageous to replace the native *Y. lipolytica* Δ12 desaturase with the *F. moniliforme* Δ12 desaturase, since the latter shows increased percent substrate conversion. More specifically, although both Δ12 desaturases catalyze the conversion of oleic acid to LA, the two enzymes differ in their overall specificity (which thereby affects each enzyme's percent substrate conversion). The Applicants have determined that the *F. moniliforme* Δ12 desaturase has a higher loading capacity of LA onto the sn-2 position of a phosphotidylcholine substrate (thereby facilitating the subsequent reaction by Δ6 desaturase) than the *Y. lipolytica* Δ12 desaturase. On this basis, overexpression of the *F. moniliforme* Δ12 desaturase in conjunction with a knockout of the *Y. lipolytica* Δ12 desaturase may result in increased product for subsequent conversion to EPA.

In alternate embodiments of the invention, other DNAs that, although not substantially identical to the *Yarrowia lipolytica* Δ12 desaturase, synthetically produced Δ6 desaturase (codon-optimized for expression in *Y. lipolytica*) and the *S. diclina* Δ6 desaturase, also can be used for the purposes herein (e.g., for production of GLA). For example, DNA sequences encoding Δ6 desaturase polypeptides that would be useful for introduction into an oleaginous yeast according to the teachings of the present invention may be obtained from microorganisms having an ability to produce GLA or STA. Such microorganisms include, for example, those belonging to the genera *Mortierella, Conidiobolus, Pythium, Phytophathora, Penicillium, Porphyridium, Coidosporium, Mucor, Fusarium, Aspergillus, Rhodotorula* and *Entomophthora*. Within the genus *Porphyridium*, of particular interest is *P. cruentum*. Within the genus *Mortierella*, of particular interest are *M. elongata, M. exigua, M. hygrophila, M. ramanniana* var. *angulispora* and *M. alpina*. Within the genus *Mucor*, of particular interest are *M. circinelloides* and *M. javanicus*.

Alternatively, a related desaturase that is not substantially identical to e.g., the *S. diclina* Δ6 desaturase, but which can desaturate a fatty acid molecule at carbon 6 from the carboxyl end of the molecule would also be useful in the present invention as a Δ6 desaturase, assuming the desaturase can still effectively convert LA to GLA. As such, related desaturases can be identified (or created) by their ability to function substantially the same as the desaturases disclosed herein.

As suggested above, in another embodiment one skilled in the art could create a fusion protein having both Δ12 desaturase and Δ6 desaturase activities suitable for the purposes herein. This would be possible, for example, by fusing together a Δ12 desaturase and Δ6 desaturase with an adjoining linker. Either the Δ12 desaturase or the Δ6 desaturase could be at the N-terminal portion of the fusion protein. Means to design and synthesize an appropriate linker molecule are readily known by one of skill in the art; for example, the linker can be a stretch of alanine or lysine amino acids and will not affect the fusion enzyme's activity.

In alternate embodiments, one skilled in the art could isolate a gene encoding a protein having both Δ12 desaturase and Δ6 desaturase activities. Such a gene could also be used to produce GLA.

Finally, it is well known in the art that methods for synthesizing sequences and bringing sequences together are well established in the literature. Thus, in vitro mutagenesis and selection, site-directed mutagenesis or other means can be employed to obtain mutations of naturally occurring desaturase genes. This would permit production of a polypeptide having desaturase activity, respectively, in vivo with more desirable physical and kinetic parameters for functioning in the host cell (e.g., a longer half-life or a higher rate of production of a desired PUFA).

If desired, a Δ6 desaturase could be mutated to possess both Δ6 and Δ12 desaturase activities, or be completely changed into a Δ12 desaturase. Likewise, a Δ12 desaturase could be mutated to possess both Δ12 and Δ6 desaturase activities, or be completely changed into a Δ6 desaturase. Such mutated genes could also be used to produce GLA.

If desired, the regions of a polypeptide of interest (i.e., a Δ6 and/or Δ12 desaturase) important for enzymatic activity can be determined through routine mutagenesis, expression of the resulting mutant polypeptides and determination of their activities. Mutants may include deletions, insertions and point mutations, or combinations thereof. A typical functional analysis begins with deletion mutagenesis to determine the N— and C-terminal limits of the protein necessary for function, and then internal deletions, insertions or point mutants are made to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after the 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites. Internal deletions can similarly be made through a variety of methods including the use of existing restriction sites in the DNA, by use of mutagenic primers via site-directed mutagenesis or mutagenic PCR. Insertions are made through methods such as linker-scanning mutagenesis, site-directed mutagenesis or mutagenic PCR, while point mutations are made through techniques such as site-directed mutagenesis or mutagenic PCR.

Chemical mutagenesis also can be used for identifying regions of a desaturase polypeptide important for activity. A mutated construct is expressed, and the ability of the resulting altered protein to function as a desaturase is assayed. Such structure-function analysis can determine which regions may be deleted, which regions tolerate insertions and which point mutations allow the mutant protein to function in substantially the same way as the native desaturase.

Preferred Microbial Hosts for GLA Production

Host cells for production of GLA may include microbial hosts that grow on a variety of feedstocks, including simple or complex carbohydrates, organic acids and alcohols, and/or hydrocarbons over a wide range of temperature and pH values.

Preferred microbial hosts, however, are oleaginous yeast. These organisms are naturally capable of oil synthesis and accumulation, wherein the oil can comprise greater than about 25% of the cellular dry weight, more preferably greater than about 30% of the cellular dry weight and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.* 82(1):43-9 (2002)).

Metabolic Engineering for High-Level GLA Biosynthesis in Oleaginous Yeast

Methods for manipulating biochemical pathways are well known to those skilled in the art; and, it is expected that numerous manipulations will be possible to maximize GLA biosynthesis in oleaginous yeast, and particularly, in *Yarrowia lipolytica*. As is well known to one of skill in the art, merely inserting a gene (e.g., a desaturase) into a cloning vector does not ensure that it will be successfully expressed at the level needed. It may be desirable to manipulate a number of different genetic elements that control aspects of transcription, translation, protein stability, oxygen limitation and secretion from the host cell. More specifically, gene expression may be controlled by altering any of the following: the nature of the relevant transcriptional promoter and terminator sequences; the number of copies of the cloned gene; whether the gene is plasmid-borne or integrated into the genome of the host cell; the final cellular location of the synthesized foreign protein; the efficiency of translation in the host organism; the intrinsic stability of the cloned gene protein within the host cell; and the codon usage within the cloned gene, such that its frequency approaches the frequency of preferred codon usage of the host cell. Each of these types of modifications are encompassed in the present invention, as a means to increase the yield of GLA. Additionally, one must consider that metabolic engineering directly within the PUFA biosynthetic pathway may also be supplemented by additional manipulation of pathways that contribute carbon to the PUFA biosynthetic pathway and global regulators that affect GLA production. Several of these methods of modifying gene expression will be discussed below, as a means to increase GLA production in oleaginous microbial host cells following selection of a particular Δ12 and Δ6 desaturase(s).

1) The Nature Of The Relevant Transcriptional Promoter And Terminator Sequence: Expression of the desaturase gene(s) can be increased at the transcriptional level through the use of a stronger promoter (either regulated or constitutive) to cause increased expression, by removing/deleting destabilizing sequences from either the mRNA or the encoded protein, or by adding stabilizing sequences to the mRNA (U.S. Pat. No. 4,910,141).

Initiation control regions or promoters which are useful to drive expression of desaturases in the desired host cell are numerous and familiar to those skilled in the art. Virtually any promoter capable of directing expression of these genes in the selected host cell is suitable for the present invention. Expression in a host cell can be accomplished in a transient or stable fashion. Transient expression can be accomplished by inducing the activity of a regulatable promoter operably linked to the gene of interest; alternatively, stable expression can be achieved by the use of a constitutive promoter operably linked to the gene of interest. As an example, when the host cell is yeast, transcriptional and translational regions functional in yeast cells are provided, particularly from the host species. The transcriptional initiation regulatory regions can be obtained, for example, from: 1.) genes in the glycolytic pathway, such as alcohol dehydrogenase, glyceraldehyde-3-phosphate-dehydrogenase (WO 2005/003310), phosphoglycerate mutase (WO 2005/003310), fructose-bisphosphate aldolase (WO 2005/049805), glycerol-3-phosphate o-acyltransferase (U.S. Patent Application No. 60/610,060), phosphoglucoseisomerase, phosphoglycerate kinase, etc.; or 2.) regulatable genes, such as acid phosphatase, lactase, metallothionein, glucoamylase, the translation elongation factor EF1-α (TEF) protein (U.S. Pat. No. 6,265,185), ribosomal protein S7 (U.S. Pat. No. 6,265,185), etc. Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest (see, e.g., WO2004/101753 for specific teachings applicable for *Yarrowia lipolytica*).

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, the termination region is derived from a yeast gene, particularly *Saccharomyces, Schizosaccharomyces, Candida, Yarrowia* or *Kluyveromyces*. The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included. Termination regions used in the disclosure herein include the extracellular protease gene terminator (XPR), the 1-aminocyclopropane-1-carboxylate oxidase (Aco3) terminator and the 3-oxoacyl-coA thiolase (OCT) terminator, although these examples are not intended to be limiting.

2) The Number Of Copies Of The Cloned Gene: Additional copies of the desaturase gene(s) may be introduced into the host to increase the output of the ω-6 fatty acid biosynthetic pathway and thereby increase GLA production. Specifically, additional copies may be cloned within a single expression construct; and/or, additional copies of the cloned gene may be introduced into the host cell by increasing the plasmid copy number or by multiple integration of the cloned gene into the genome (infra).

3) Whether The Gene(s) Is Plasmid-Borne Or Integrated Into The Genome Of The Host Cell: Once the DNA encoding a desaturase polypeptide suitable for expression in an oleaginous yeast has been obtained, it is placed in a plasmid vector capable of autonomous replication in a host cell; or, it is directly integrated into the genome of the host cell. Integration of expression cassettes can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

The preferred method of expressing genes in oleaginous yeast is by integration of linear DNA into the genome of the host; and, integration into multiple locations within the genome can be particularly useful when high level expression of genes is desired. Toward this end, it is desirable to identify a sequence within the genome that is present in multiple copies.

Schmid-Berger et al. (*J. Bact.* 176(9):2477-2482 (1994)) discovered the first retrotransposon-like element Ylt1 in *Yarrowia lipolytica*. This retrotransposon is characterized by the presence of long terminal repeats (LTRs; each approximately 700 bp in length) called zeta regions. Ylt1 and solo zeta elements were present in a dispersed manner within the genome in at least 35 copies/genome and 50-60 copies/genome, respectively; both elements were determined to function as sites of homologous recombination. Further, work by Juretzek et al. (*Yeast* 18:97-113 (2001)) demonstrated that gene expression could be dramatically increased by targeting plasmids into the repetitive regions of the yeast genome (using linear DNA with LTR zeta regions at both ends), as compared to the expression obtained using low-copy plasmid transformants. Thus, zeta-directed integration can be ideal as a means to ensure multiple integration of plasmid DNA into *Y. lipolytica*, thereby permitting high-level gene expression.

Unfortunately, however, not all strains of *Y. lipolytica* possess zeta regions (e.g., the strain identified as ATCC #20362). When the strain lacks such regions, it is also possible to integrate plasmid DNA comprising expression cassettes into alternate loci to reach the desired copy number for the expression cassette. For example, preferred alternate loci include: the Ura3 locus (GenBank Accession No. AJ306421), the Leu2 gene locus (GenBank Accession No. AF260230), the Lys5 gene (GenBank Accession No. M34929), the Aco2 gene locus (GenBank Accession No. AJ001300), the Pox3 gene locus (Pox3: GenBank Accession No. XP_503244; or, Aco3: GenBank Accession No. AJ001301), the Δ12 desaturase gene locus, the Lip1 gene locus (GenBank Accession No. Z50020) and/or the Lip2 gene locus (GenBank Accession No. AJ012632).

4) The Final Cellular Location Of The Synthesized Foreign Protein: Mounting evidence appears to indicate that exogenously supplied fatty acids enter the yeast cell by concomitant conversion to acyl-CoAs before their use for various metabolic purposes (Domergue, F. et al. *J. Biol. Chem.* 278(37):35115-35126 (2003)). Different desaturases, however, are preferentially able to perform desaturation in the acyl-CoA pool versus the phosphatidylcholine pool (acting preferentially on the sn-2 position); the functionality of the desaturase appears to be determined, in part, according to its origin (e.g., lower plants, worms, fungi, algae, human, etc.).

For some applications, it will be useful to direct the instant proteins to different cellular compartments. For the purposes described herein, GLA may as be found as free fatty acids or in esterified forms such as acylglycerols, phospholipids, sulfolipids or glycolipids. It is envisioned that the chimeric genes described above encoding polypeptides that permit GLA biosynthesis may be further engineered to include appropriate intracellular targeting sequences.

5) The Efficiency Of Translation In The Host Organism/Codon Usage Within The Cloned Gene(s): Yet another approach to increase expression of the desaturase genes required for GLA production is to increase the translational efficiency of the encoded mRNAs by replacement of codons in the native gene with those for optimal gene expression in the selected host microorganism. Specifically, it is frequently useful to modify a portion of the codons encoding a particular polypeptide that is to be expressed in a foreign host, such that the modified polypeptide uses codons that are preferred by the alternative host. Use of host preferred codons can substantially enhance the expression of the foreign gene encoding the polypeptide.

In general, host preferred codons can be determined within a particular host species of interest by examining codon usage in proteins (preferably those expressed in the largest amount) and determining which are used with highest frequency. Then, the coding sequence for a polypeptide of interest can be synthesized in whole or in part using the codons preferred in the host species. All (or portions) of the DNA also can be synthesized to remove any destabilizing sequences or regions of secondary structure that would be present in the transcribed mRNA. And, all (or portions) of the DNA also can be synthesized to alter the base composition to one more preferable in the desired host cell.

As an example of this technique, in the present invention it was desirable to utilize a synthetic codon-optimized Δ6 desaturase wherein a portion of the codons encoding the polypeptide had been modified to correspond to those preferred by the alternative host, *Yarrowia lipolytica*. Specifically, in addition to modifications within the translation initiation site, 152 bp of the 1374 bp coding region of the *Mortierella alpina* Δ6 desaturase were modified (corresponding to 144 codons) to enhance the percent substrate conversion in *Y. lipolytica* from 30% to 42% (see WO 2004/101753, Example 8). The skilled artisan will appreciate that these optimization methods will be equally applicable to other genes that one would like to express in a host for high-level expression of GLA.

6) The Intrinsic Stability Of The Cloned Gene and/or Expressed Protein Within The Host Cell: Juretzek et al. (*Yeast* 18:97-113 (2001)) note that the stability of integrated plasmid copy number in *Yarrowia lipolytica* is dependent on the individual transformants, the recipient strain and the targeting platform used. Thus, the skilled artisan will recognize that multiple transformants must be screened in order to obtain a strain displaying the desired expression level and pattern. Such screening may be accomplished by Southern analysis of DNA blots (Southern, *J. Mol. Biol.* 98:503 (1975)), Northern analysis of mRNA expression (Kroczek, *J. Chromatogr. Biomed. Appl.*, 618 (1-2):133-145 (1993)), Western analysis of protein expression, phenotypic analysis or GC analysis of the PUFA products.

7) Manipulations Within The ω-3/ω-6 Biosynthetic Pathway: In the case of manipulations within the ω-3/ω-6 biosynthetic pathway, it may be desirable to increase the production of LA to enable increased production of GLA. This may be accomplished by introducing (and/or amplifying) the genes encoding Δ6 and/or Δ12 desaturases.

Additionally, it is well known to one skilled in the art that GLA production is favored in a host microorganism that is substantially free of ALA. Thus, preferably, the host is selected or obtained by removing or inhibiting Δ15 or ω-3 type desaturase activity that permits conversion of LA to ALA. The endogenous desaturase activity can be reduced or eliminated by, for example: 1.) providing a cassette for transcription of antisense sequences to the Δ15 desaturase transcription product; 2.) disrupting the Δ15 desaturase gene through insertion, substitution and/or deletion of all or part of the target gene; or 3.) using a host cell which naturally has [or has been mutated to have] low or no Δ15 desaturase activity. Inhibition of undesired desaturase pathways can also be accomplished through the use of specific desaturase inhibitors such as those described in U.S. Pat. No. 4,778,630.

8) Manipulation Of Pathways Contributing Carbon To The ω-3/ω-6 Biosynthetic Pathway: Beyond the immediate PUFA biosynthetic pathway, it is expected that manipulation of several other enzymatic pathways leading to the biosynthesis of precursor fatty acids may contribute to the overall net biosynthesis of specific PUFAs. For example, it may be useful to increase the flow of carbon into the PUFA biosynthetic pathway by increasing the availability of the precursors of longer chain saturated and unsaturated fatty acids, such as palmitate (16:0), stearic acid (18:0) and oleic acid (18:1). The synthesis of the palmitate is dependent on the activity of a $C_{14/16}$ elongase, while the synthesis of stearic acid is dependent on the activity of a $C_{16/18}$ elongase; oleic acid is the product of the reaction catalyzed by Δ9 desaturase. Thus, in some embodiments of the present invention, it may be useful to over-express a Δ9 desaturase, $C_{14/16}$ elongase and/or a $C_{16/18}$ elongase, in addition to the GLA biosynthetic pathway enzymes to thereby increase the substrate availability for those PUFA enzymes. The work of Inagaki, K. et al. (*Biosci. Biotech. Biochem.* 66(3): 613-621 (2002)) specifically suggests advantages associated with co-expression of a heterologous $C_{16/18}$ elongase from *Rattus norvegicus* (GenBank Accession No. AB071986). And, subsequent work by the Applicants has confirmed that over-expression of a codon-optimized $C_{16/18}$ elongase from *R. norvegicus* can substantially increase carbon flow into the PUFA pathway, by increasing conversion of C16 to C18 fatty acids. Thus, although a *Yarrowia lipolytica* host strain must minimally be manipulated to express a Δ6 desaturase and Δ12 desaturase for GLA biosynthesis, in a further preferred embodiment the host strain additionally includes at least one of the following: a Δ9 desaturase, $C_{14/16}$ elongase and/or a $C_{16/18}$ elongase. Up-regulation of selected biochemical pathways and gene products may be controlled using the techniques described above. In contrast, it may be necessary to down-regulate portions of certain biochemical pathways competing with the fatty acid biosynthetic pathway for energy or carbon. If so, these undesirable biosynthetic pathways may be eliminated by gene disruption or down-regulated by other means (e.g., antisense technology, mutagenesis with radiation or chemical agents or by use of transposable elements/transposons), as reviewed in WO2004/101757.

Within the context of the present invention, it may be useful to modulate the expression of a GLA biosynthetic pathway by any one of the methods described above. For example, the present invention provides methods whereby genes encoding Δ6 desaturase and Δ12 desaturase activities are introduced into oleaginous yeast such as *Yarrowia lipolytica* for the high-level production of GLA. It will be particularly useful to express these genes in oleaginous yeast that do not naturally possess ω-3 and/or ω-6 fatty acid biosynthetic pathways and to coordinate the expression of these genes to maximize production of GLA using various means of metabolic engineering within the host organism.

Expression Systems, Cassettes, Vectors and Transformation

Microbial expression systems and expression vectors containing regulatory sequences that direct high-level expression of foreign proteins such as GLA are well known to those skilled in the art. Any of these could be used to construct chimeric genes encoding the preferred desaturase sequences. These chimeric genes could then be introduced into appropriate heterologous microbial host cells, particularly in the cells of oleaginous yeast (e.g., *Yarrowia lipolytica*), via transformation to provide high-level expression of the encoded enzymes.

Vectors or DNA cassettes useful for the transformation of suitable host cells are well known in the art. The specific choice of sequences present in the construct is dependent upon the desired expression products, the nature of the host cell, and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation and a region 3' of the DNA fragment that controls transcriptional termination. It is most preferred when both control regions are derived from genes from the transformed host cell, although it is to be understood that such control regions need not be derived from the genes native to the specific species chosen as a production host.

Where two or more genes are expressed from separate replicating vectors, it is desirable that each vector has a different means of selection and should lack homology to the other constructs to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene(s) of interest may be introduced into a host cell by any standard technique. These techniques include transformation (e.g., lithium acetate transformation [*Methods in Enzymology*, 194:186-187 (1991)]), protoplast fusion, bolistic impact, electroporation, microinjection, or any other method that introduces the gene(s) of interest into the host cell. More specific teachings applicable for oleaginous yeast (i.e., *Yarrowia lipolytica*) include U.S. Pat. Nos. 4,880,741 and 5,071,764 and Chen, D. C. et al. (*Appl Microbiol Biotechnol*. 48(2):232-235 (1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified, or is present on an extrachromosomal element having multiple copy numbers. The transformed host cell can be identified by various selection techniques, as described in WO2004/101757. Preferred selection methods for use herein are resistance to kanamycin, hygromycin and the amino glycoside G418, as well as ability to grow on media lacking uracil, leucine, lysine, tryptophan or histidine.

Accordingly, it is expected that introduction of chimeric genes encoding a GLA biosynthetic pathway (e.g., a Δ12 desaturase and Δ6 desaturase), under the control of appropriate promoters will result in production of GLA when the microbial host cell is provided with oleic acid as the desaturase substrate. The level of Δ12 desaturase gene expression and Δ6 desaturase gene expression required will depend on the host cell, its ability to synthesize PUFAs using endogenous desaturases/elongases and the availability of substrate (which may be produced endogenously or be supplied exogenously). Using the teachings provided herein, transformant oleaginous microbial hosts will produce at least about 15% GLA in the total lipids, preferably at least about 20% GLA in the total lipids, more preferably at least about 30% GLA in the total lipids, more preferably at least about 40% GLA in the total lipids and most preferably at least about 50% GLA in the total lipids.

Fermentation Processes for GLA Production

The transformed microbial host cell is grown under conditions that optimize desaturase activities and produce the greatest and the most economical yield of GLA. In general, media conditions that may be optimized include the type and amount of carbon source, the type and amount of nitrogen source, the carbon-to-nitrogen ratio, the oxygen level, growth temperature, pH, length of the biomass production phase, length of the oil accumulation phase and the time of cell harvest. Microorganisms of interest, such as oleaginous yeast, are grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources may include, but are not limited to: monosaccharides (e.g., glucose, fructose), disaccharides (e.g., lactose, sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids and various commercial sources of fatty acids including vegetable oils (e.g., soybean oil) and animal fats. Additionally, the carbon source may include one-carbon sources (e.g., carbon dioxide, methanol, formaldehyde, formate, carbon-containing amines) for which metabolic conversion into key biochemical intermediates has been demonstrated. Hence it is contemplated that the source of carbon utilized in the present invention may encompass a wide variety of carbon-containing sources and will only be limited by the choice of host organism. Although all of the above-mentioned carbon sources and mixtures thereof are expected to be suitable in the present invention, preferred carbon sources are sugars and/or fatty acids. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art, appropriate for the growth of the microorganism and promotion of the enzymatic pathways necessary for GLA production. Particular attention is given to several metal ions (e.g., $Mn^{+2}$, $Co^{+2}$, $Zn^{+2}$, $Mg^{+2}$) that promote synthesis of lipids and PUFAs (Nakahara, T. et al. *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.0 is preferred as the range for the initial growth conditions. The fermentation may be conducted under aerobic or anaerobic conditions, wherein microaerobic conditions are preferred.

Typically, accumulation of high levels of PUFAs such as GLA in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast. This approach is described in WO 2004/101757, as are various suitable fermentation process designs (i.e., batch, fed-batch and continuous) and considerations during growth.

Purification of PUFAs

The PUFAs may be found in the host microorganism as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Z. Jacobs (*Critical Reviews in Biotechnology* 12(5/6):463491 (1992)). A brief review of downstream processing is also available by A. Singh and O. Ward (*Adv. Appl. Microbiol.* 45:271-312 (1997)).

In general, means for the purification of PUFAs such as GLA may include extraction with organic solvents, sonication, supercritical fluid extraction (e.g., using carbon dioxide), saponification, and physical means such as presses, or combinations thereof. One is referred to the teachings of WO 2004/101757 for additional details.

DESCRIPTION OF PREFERRED EMBODIMENTS

The present invention demonstrates the feasibility of engineering high-level production of GLA in oleaginous yeast. Toward this end, a GLA biosynthetic pathway was introduced into Yarrowia lipolytica by the introduction of genes encoding Δ12 and Δ6 desaturase activities. Specific modifications that were designed to increase production of GLA comprised: (1) use of zeta-directed integration to ensure multiple integration of expression cassettes into the zeta loci of the *Y. lipolytica* genome; (2) introduction of Δ6 desaturase activity by incorporation of a TEF::Δ6::XPR chimeric gene, wherein the Δ6 desaturase was a synthetic gene (originally derived from *Mortierella alpina*) that was codon-optimized for expression in *Yarrowia*; (3) up-regulation of endogenous Δ12 desaturase activity, by creation of a TEF::Δ12::XPR chimeric gene; optionally, (4) addition of a second Δ6 desaturase, in the form of a TEF::Δ6::OCT chimeric gene, wherein the Δ6 desaturase gene was isolated from *Saprolegnia diclina*; and optionally, (5) insertion of a GPD::Δ12::Aco3 chimeric gene, wherein expression of the *Yarrowia* Δ12 desaturase was driven by a glyceraldehyde-3-phosphate-dehydrogenase (GPD) promoter of *Yarrowia*.

Upon transformation of plasmid pDMW208, wherein a single copy each of a Δ12 desaturase gene and a Δ6 desaturase gene were integrated into the zeta loci of the *Y. lipolytica* genome, GC analysis of the host cells determined that those transformants produced 25.9% GLA in the total lipids. In contrast, recombinant *Y. lipolytica* that had been transformed with plasmid pDMW208D62, such that two copies each of a Δ12 desaturase gene and a Δ6 desaturase gene were integrated into the zeta loci of the *Y. lipolytica* genome, produced 34% GLA in the total lipids.

Although the Applicants demonstrate production of 25.9% and 34% GLA in these particular recombinant strains of *Y. lipolytica*, it will be apparent that the concentration of GLA in the host cells could be dramatically increased via additional genetic modifications, according to the invention herein and as suggested in U.S. Patent Application No. 60/624812. Furthermore, on the basis of the teachings and results described herein, it is expected that one skilled in the art will recognize the feasability and commercial utility created by using oleaginous yeast as a production platform for the synthesis of a variety of ω-3 and/or ω-6 PUFAs.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1.) Sambrook, J., Fritsch, E. F. and Maniatis, T. *Molecular Cloning: A Laboratory Manual*; Cold Spring Harbor Laboratory: Cold Spring Harbor, N.Y. (1989) (hereinafter "Maniatis"); 2.) T. J. Silhavy, M. L. Bennan, and L. W. Enquist, Experiments with Gene Fusions; Cold Spring Harbor Laboratory: Cold Spring Harbor, N.Y. (1984); and 3.) Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, 2$^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.) or Sigma Chemical Company (St. Louis, Mo.), unless otherwise specified.

E. coli (XL1-Blue) competent cells were purchased from the Stratagene Company (San Diego, Calif.). E. coli strains were typically grown at 37° C. on Luria Bertani (LB) plates.

A leucine autotrophic strain of Yarrowia lipolytica was purchased from the American Type Culture Collection (Rockville, Md.; ATCC #76982) and used for functional assays. Y. lipolytica strains were usually grown at 28° C. on YPD agar (1 % yeast extract, 2% bactopeptone, 2% glucose, 2% agar). For selection of transformants, minimal medium (0.17% yeast nitrogen base (DIFCO, Detroit, Mich.) without ammonium sulfate or amino acids, 2% glucose, 0.1% proline, pH 6.1) was used. Supplements of adenine, leucine, lysine and/or uracil were added to a final concentration of 0.01%.

General molecular cloning was performed according to standard methods (Sambrook et al., supra). Oligonucleotides were synthesized by Sigma-Genosys (Spring, Tex.). Site-directed mutagenesis was performed using Stratagene's QuikChange™ Site-Directed Mutagenesis kit, per the manufacturer's instructions. When polymerase chain reaction (PCR) or site-directed mutagenesis was involved in subcloning, the constructs were sequenced to confirm that no errors had been introduced to the sequence. PCR products were cloned into Promega's pGEM-T-easy vector (Madison, Wis.).

Manipulations of genetic sequences were accomplished using the suite of programs available from the Genetics Computer Group, Inc. (Wisconsin Package Version 9.0, Genetics Computer Group (GCG), Madison, Wis.). The GCG program "Pileup" was used with the gap creation default value of 12, and the gap extension default value of 4. The GCG "Gap" or "Bestfit" programs were used with the default gap creation penalty of 50 and the default gap extension penalty of 3. Unless otherwise stated, in all other cases GCG program default parameters were used.

The meaning of abbreviations is as follows: "sec" means second(s), "min" means minute(s), "hr" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kB" means kilobase(s).

Example 1

Construction of a Zeta Integration Plasmid

Plasmid pYZ2A (FIG. 2) was constructed as a derivative of pYZV5 to facilitate integration of the plasmid into the zeta regions of the Yarrowia lipolytica genome. Briefly, pYZV5 (WO2004/101757, Example 4) comprised the following: (1) an ampicillin-resistance gene (Amp$^R$); (2) 401 bp of 5'-sequence and 568 bp of 3'-sequence from the Y. lipolytica URA3 gene to direct integration of expression cassettes into the Ura loci of the Yarrowia genome; (3) a Yarrowia isopropylmalate isomerase (LEU2) gene; (4) the Y. lipolytica translation elongation factor EF1-α (TEF) protein promoter (U.S. Pat. No. 6,265,185); (5) a Mortierella alpina (GenBank Accession #AF067654; U.S. Pat. No. 6,075,183) Δ5 desaturase; and (6) the extracellular protease gene terminator (XPR). Plasmid pYZ2A was constructed by substituting fragments of the zeta region for the fragments directing integration into the URA3 gene of the pYZV5 construct.

Specifically, genomic DNA was purified from Y. lipolytica ATCC #79682 using Qiagen's DNeasy Tissue Kit in the following manner: a 5 mL overnight culture of ATCC #79682 was spun down and washed in 5 mL SCE buffer (1 M sorbital, 0.1 M sodium citrate and 60 mM EDTA), before being resuspended again in 50 µl SCE containing 2 mM β-mercaptoethanol and 10 units zymolyase (ICN Biomedicals, Inc.). The cells were then incubated at 37° C. for 1 hr, prior to 15 min incubation at 70° C. to inactivate the zymolyase. Qiagen's protocol was resumed following the inactivation step and was followed for the remainder of the DNA isolation. PCR amplification was carried out in a 50 µl total volume containing: 100 ng Yarrowia genomic DNA, PCR buffer containing 10 mM KCl, 10 mM (NH$_4$)$_2$SO$_4$, 20 mM Tris-HCl (pH 8.75), 2 mM MgSO$_4$, 0.1% Triton X-100, 100 µg/mL BSA (final concentration), 200 µM each deoxyribonucleotide triphosphate, 10 pmole of each primer (infra) and 1 µl of PfuTurbo DNA polymerase (Stratagene, San Diego, Calif.). Amplification was carried out as follows: initial denaturation at 95° C. for 3 min, followed by 35 cycles of the following: 95° C. for 1 min, 56° C. for 30 sec, 72° C. for 1 min. A final extension cycle of 72° C. for 10 min was carried out, followed by reaction termination at 4° C.

Primers for the amplification of the zeta regions were designed according to the sequence of Ylt1, a highly repetitive retrotransposon in the genome of Yarrowia lipolytica (Schmid-Berger, N. et al., J Bacteriol. 176(9):2477-82 (1994)). These primers are shown below in Table 3; underlined regions within each primer sequence correspond with a specific restriction enzyme site that was designed to enable downstream cloning reactions.

TABLE 3

Primers For Amplification Of The Zeta Regions

| Primer | Sequence | Encoded Restriction Enzyme Site | SEQ ID NO |
|---|---|---|---|
| YL127 | TTTGGCGCGCCTGTGCGTACC AGGGATAGGGTAGG | Asc1 | SEQ ID NO:1 |
| YL128 | TTTCGTACGGACCACCTCCCT TGCACTTCTTG | BsiW1 | SEQ ID NO:2 |
| YL129 | GGGTTAATTAACGCCGATTCT CTCTGCAGTCG | Pac1 | SEQ ID NO:3 |

TABLE 3-continued

Primers For Amplification Of The Zeta Regions

| Primer | Sequence | Encoded Restriction Enzyme Site | SEQ ID NO |
|---|---|---|---|
| YL130 | TTT<u>GCATGC</u>TCTGGAGAGTTA GTCATCCGAC | Sph1 | SEQ ID NO:4 |

Figure 2:
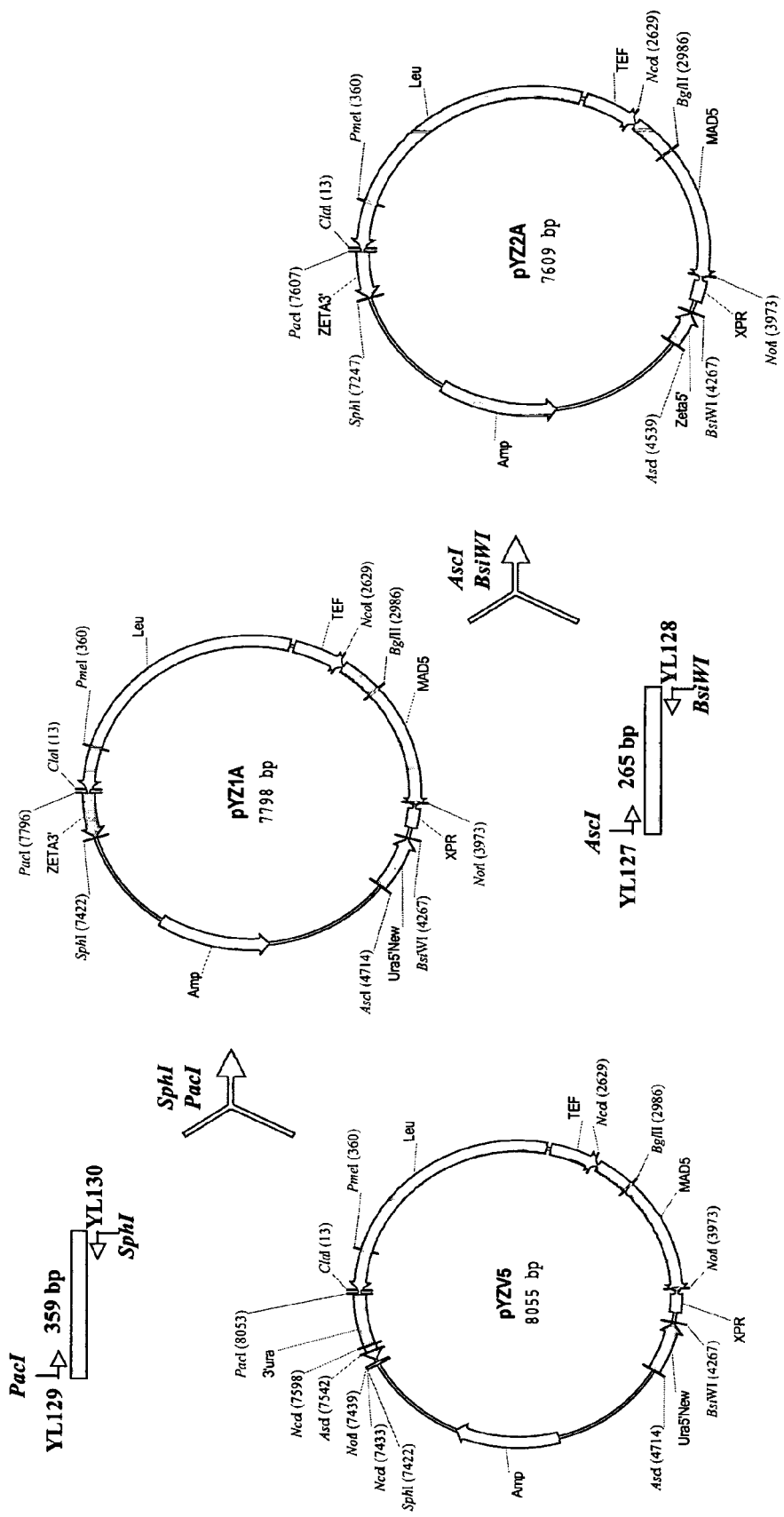
FIG. 2 illustrates the construction of intermediate plasmid vector pYZ2A.

Amplification of the 3' zeta region of *Y. lipolytica* utilized primers YL129 and YL130 and the genomic DNA described above. The product was digested with Pac1 and Sph1, gel-purified, and the resulting 359 bp PCR fragment (SEQ ID NO:6) was cloned into Pac1 and Sph1 digested pYZV5 (WO2004/101757). The plasmid was named pYZ1A (FIG. 2).

A second PCR reaction was conducted with primers YL127 and YL128 to amplify the 5' zeta region of *Y. lipolytica*. The PCR product was digested with Asc1 and BsiW1, gel-purified, and the 265 bp fragment (SEQ ID NO:5) was cloned into Asc1- and BsiW1-digested pYZ1A, to produce pYZ2A (FIG. 2).

Thus, pYZ2A possessed a 265 bp 5'-sequence (SEQ ID NO:5) from the *Y. lipolytica* zeta region and a 359 bp 3'-sequence (SEQ ID NO:6) from the *Y. lipolytica* zeta region suitable to direct integration of expression cassettes into the zeta loci of the *Yarrowia* genome.

Example 2

Construction pf a High GLA Producing Plasmid, pDMW208, Comprising a Δ6 Desaturase and a Δ12 Desaturase In order to produce high levels of GLA, a variety of modifications to plasmid pYZ2A (from Example 1) were engineered. Specifically, this Example describes the insertion of a synthetic Δ6 desaturase gene (responsible for conversion of LA to GLA) and a native Δ12 desaturase gene (responsible for conversion of oleic acid to LA) to ultimately produce plasmid pDMW208. The latter enzymatic activity was utilized to increase the carbon flux through the GLA biosynthetic pathway; the former activity was required for the synthesis of the desired product, GLA.

Cloning of a Synthetic Codon-Optimized Δ6 Desaturase

Plasmid pDMW200 was synthesized by cloning the Δ6 desaturase from pYD6S (described in WO2004/101753 and illustrated herein as FIG. 3A; Δ6 desaturase gene labeled as "D6Syn") into Not1- and Nco1-digested pYZ2A (Example 1). Specifically, pYD6S contains a synthetic DNA fragment encoding Δ6 desaturase (SEQ ID NO:7) that is codon-optimized for expression in *Yarrowia*, wherein 152 bp of the 1374 bp coding region of the wildtype *Mortierella alpina* Δ6 desaturase (GenBank Accession #AF46528) were modified (corresponding to 144 codons), in addition to modifications within the translation initiation site. This optimization led to an increase in percent substrate conversion (calculated as [product/(substrate +product)]*100) of the gene from 30% to 42%, upon expression in *Yarrowia* under the control of the TEF promoter. As a result of cloning, pDMW200 comprised a 1949 bp TEF::Δ6::XPR chimeric gene (SEQ ID NO:9).

pDMW200-B was then constructed as a derivative of pDMW200 to facilitate subcloning and heterologous gene expression in *Y. lipolytica*. Specifically, pDMW200-B was constructed by a single round of site-directed mutagenesis using pDMW200 as a template. A BglIII site was introduced into pDMW200 in the 3' end of the leucine gene, 44 bases upstream of the existing Pme1 site using oligonucleotides YL238 (SEQ ID NO:10) and YL239 (SEQ ID NO:11).

Cloning of a *Yarrowia lipolytica* Δ12 Desaturase

Although wildtype *Yarrowia* has a Δ12 desaturase gene (sequenced and biochemically characterized in WO2004/104167), a copy of this gene was introduced into pDMW200-B to amplify the endogenous Δ12 desaturase activity. Specifically, the Δ12 desaturase gene was derived from plasmid pY25-d12d (illustrated herein as FIG. 3B; see WO2004/104167, Example 4 for further details). Using oligonucleotides YL242 (SEQ ID NO:12) and YL243 (SEQ ID NO:13) as primers and pY25-d12d as template, a Pme1 site was introduced into pY25-d12d by site-directed mutagenesis to generate pY25-d12d-P. A second round of mutagenesis was then conducted using oligonucleotides YL240 (SEQ ID NO:14) and YL241 (SEQ ID NO:15) as primers to introduce a BglIII site into pY25-d12d-P, thereby generating pY25-d12d-PB (FIG. 3C).

The Δ12 desaturase gene, flanked by a TEF promoter and an XPR terminator, was isolated from BglIII/Pme1-digested pY25-d12d-PB. The ~1.9 kB fragment (SEQ ID NO:16) was gel purified and ligated into BglIII/Pme1-digested pDMW200-B. The resulting plasmid was called pDMW208 (SEQ ID NO:17).

As shown in FIG. 3D, the pDMW208 expression vector is a 9541 bp plasmid comprising: a Δ12 desaturase gene ("d12") flanked by a TEF promoter and an XPR terminator, a Δ6 desaturase gene flanked by a TEF promoter and an XPR terminator and a leucine selection marker. These genes are flanked by sequences specific for the zeta regions of *Yarrowia*. After a Sph1/Asc1 digestion, this plasmid was targeted to integrate into the zeta regions of *Yarrowia* chromosomes. GC analyses of the transformants selected on minimal media confirmed production of GLA (see Example 5).

Example 3

Construction of a High GLA Producinq Plasmid, pDMW208D62, Comprising Two Δ6 Desaturases and Two Δ12 Desaturases As is well known in the art, gene expression can frequently be increased by amplifying the number of copies of the cloned gene(s). To test this hypothesis and possibly up-regulate GLA production with respect to that obtainable by expression of pDMW208 (Example 2), this Example describes the insertion of a second Δ6 desaturase gene and a second Δ12 desaturase gene into pDMW208 to produce plasmid pDMW208D62.

Cloning of a *Saprolegnia diclina* Δ6 Desaturase

An additional copy of a Δ6 desaturase gene cloned under control of the TEF promoter and the OCT terminator was cloned into plasmid pDMW208. First, the 1366 bp *S. diclina* Δ6 desaturase gene was amplified using plasmid pRSP1 (Abbott Laboratories, U.S. Pat. No. 6,635,451; GenBank Accession No. AX576988) as the template and oligonucleotides YL253 (SEQ ID NO:18) and YL254 (SEQ ID NO:19) as primers. PCR amplification was carried out in a 50 µl total volume containing 10 ng pRSP1 plasmid DNA, using the components and amplification conditions described in Example 1. The PCR product was digested with Nco1 and Not1 and gel purified.

The OCT terminator of the gene encoding 3-oxoacyl-coA thiolase (GenBank X69988) was amplified from *Y. lipolytica* genomic DNA using YL293 (SEQ ID NO:20) and YL317 (SEQ ID NO:21) as primers. The 372 bp PCR product was digested with Not1 and Cla1 and gel purified.

Finally, the TEF promoter was obtained from plasmid pYSD17SPC (WO2004/101757, Example 4). Specifically, plasmid pYSD17SPC (illustrated herein as FIG. 3E) was linearized with NcoI and ClaI. Then, the *S. diclina* Δ6 desaturase gene, the 372 bp PCR product encoding the OCT terminator and pYSD17SPC were all ligated together in a single standard overnight ligation reaction. The resulting plasmid was named pYTS6 (FIG. 4A). pYTS6 was digested with Cla1 and Pme1 to release a ~2.2 kB fragment (SEQ ID NO:22) containing the *S. diclina* Δ6 desaturase gene, flanked by the TEF promoter and OCT terminator. This fragment was cloned into ClaI and PmeI-digested pDMW208 to yield plasmid pDMW208D6 (FIG. 4B).

Cloning of a Second *Yarrowia lipolytica* Δ12 Desaturase

An additional copy of the *Yarrowia* Δ12 desaturase gene, cloned under control of a *Yarrowia* glyceraldehyde-3-phosphate dehydrogenase (GPD) promoter and an Aco3 terminator, was introduced into pDMW208D6. The GPD promoter, isolated and biochemically characterized in WO 2005/003310, was determined to be about 3 times stronger than the bench-marker TEF promoter in *Y. lipolytica* (activity measured according to GUS expression). Thus, the Δ12 desaturase gene from pY25-d12d-PB (Example 2) was modified to replace the existing TEF promoter with a GPD promoter and to replace the existing XPR terminator with an Aco3 terminator. This modified construct was then introduced into pDMW208D6 (supra) to yield plasmid pDMW208D62. The cloning scheme for the construction of pDMW208D62 is described below. Specifically, the construction of pDMW208D62 incorporated promoters and transcription terminators from pre-existing plasmids that contained genes unrelated to the purposes described herein. These unnecessary genes were removed from the construct prior to completion of pDMW208D62 synthesis.

First, the *Yarrowia* GPD promoter fragment was isolated from pYZGDG (WO 2005/003310, Example 5; illustrated herein as FIG. 4C). pYZGDG was completely digested with Sph1 and then partially digested with Nco1. The 3.2 kB SphI/NcoI fragment containing the chimeric GPD::LEU2 gene of PYZGDG was used to replace the Sph1/Nco1 fragment of pELS containing the chimeric TEF::LEU2 gene (WO2004/101753, Example 6; illustrated herein as FIG. 4D) to generate pYZDEL1S.

Four consecutive rounds of site-directed mutagenesis were then conducted using pYZDEL1S as a template to ultimately produce pYZDE1SB-CN. Specifically, a first round of site-directed mutagenesis allowed for the introduction of a Swa1 site into pYZDEL1S using primers YL226 and YL227 (SEQ ID NOs:23 and 24) to generate pYZDEL1S-S. A second round of site-directed mutagenesis with primers YL61 and YL62 (SEQ ID NOs:25 and 26) introduced a BsiW1 site into pYZDEL1S-S to generate pYDDE1-SB. The third round of mutagenesis eliminated the Cla1 site in the GPD promoter region of pYDDE1-SB, using primers YL230 and YL231 (SEQ ID NOs:27 and 28), to create pYZDE1SB. The final round of mutagenesis eliminated the Nco1 site within the GPD promoter region of pYZDE1SB with primers YL228 and YL229 (SEQ ID NOs:29 and 30), to thereby generate pYZDE1SB-CN.

Using pRAT-4-A7 (Abbott Laboratories, U.S. Pat. No. 6,677,145) as template and oligonucleotides YL179 and YL179A (SEQ ID NOs:31 and 32) as primers, an elongase gene from *Thraustochytrium aureum* T7091 (abbreviated as "EL2") was PCR amplified using standard conditions and inserted into the NcoI/NotI site of pY5-13 (WO2004/101757, Example 1; see FIG. 4E herein) to generate pELS2, comprising the chimeric TEF::EL2 gene. The Not1/Nco1 fragment from pEL2S was then introduced into Not1/Nco1 digested pYZDE1SB-CN to generate pGDE2S, comprising the chimeric GPD::EL2::XPR gene.

pGDE2S was subjected to two consecutive rounds of mutagenesis. The first site-directed mutagenesis step used primers YL77 and YL78 (SEQ ID NOs:33 and 34) to add a Pac1 site to pGDE2S, generating pGDE2S-P. The second step used primers YL322 and Y323 (SEQ ID NOs:35 and 36) to add a Cla1 site to pGDE2S-P to generate pGDE2S-PC.

The final step in the construction of pGDE2ST (FIG. 5) was addition of the ACO terminator. The terminator was amplified from Y. lipolytica genomic DNA by PCR with primers YL325 and YL326 (SEQ ID NOs:37 and 38) using standard PCR conditions, digested with Not1 and Pac1 and ligated with NotI/PacI-digested pGDE2S-PC to generate pGDE2ST. Thus, pGDE2ST comprised a chimeric GPD::EL2::Aco gene.

Final Synthesis of Plasmid PDMW208D62

As shown in FIG. 5, the Δ12 desaturase gene contained on pY25-d12d-PB (Example 2) was excised from the plasmid by Nco1/Not1 digestion and cloned into the Nco1/Not1 digested pGDE2ST plasmid to generate pZGD12-PC, comprising the chimeric GPD::Δ12::Aco gene. The ~2.6 kB ClaI/PacI fragment (SEQ ID NO:39) of pZGD12-PC containing the GPD:: Δ12::Aco chimeric gene was then inserted into the ClaI/PacI-digested pDMW208D6 to generate pDMW208D62 (SEQ ID NO:40).

Example 4

Transformation of *Yarrowia lipolytica*

The plasmids pDMW208 and pDMW208D62 were digested with AscI and SphI restriction endonucleases and transformed into a leucine auxotroph mutant of *Y. lipolytica* ATCC #76982 cells according to the lithium acetate method of Chen, D. C. et al. (*Appl Microbiol Biotechnol*. 48(2):232-235 (1997)). Briefly, *Y. lipolytica* was streaked onto a YPD plate and grown at 30° C. for approximately 18 hr. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and, 50 μg sheared salmon sperm DNA.

About 500 ng of plasmid DNA was incubated in 100 μl of resuspended cells, and maintained at 39° C. for 1 hr with vortex mixing at 15 min intervals. The cells were plated onto minimal media (with 0.1 g/L L-adenine and 0.1 g/L L-lysine) plates lacking leucine and maintained at 30° C. for 2 to 3 days.

Example 5

GLA Production in *Yarrowia*

Colonies of transformant *Y. lipolytica* containing pDMW208 or pDMW208D62 were each grown in 20 mL minimal media in a 125 mL Erlenmeyer flask at 30° C. After about 24 hr, when the cultures reached an OD$_{600}$~1.0, one 5 mL aliquot from each culture was removed and harvested.

The pellet was resuspended in 4 mL of FRF media (7 g KH$_2$PO$_4$, 2 g K$_2$HPO$_4$, 1 g MgSO$_4$.7H$_2$O, 1.5 g Na-glutamate, 21.7 g glucose, 0.1 g lysine). The culture (3 mL) was then added to a 14 mL Falcon culture tube (Becton Dickinson, Franklin Lakes, N.J.) and subsequently incubated at 30° C. on a shaking incubator for an additional 24 hrs.

Cells were collected from the entire 3 mL culture by centrifugation and lipids were extracted as described in Bligh, E. G. & Dyer, W. J. (Can. J. Biochem. Physiol. 37:911-917 (1959)). Fatty acid methyl esters were prepared by transesterification of the lipid extract with sodium methoxide (Roughan, G., and Nishida I. Arch Biochem Biophys. 276(1): 38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

Figure 6:
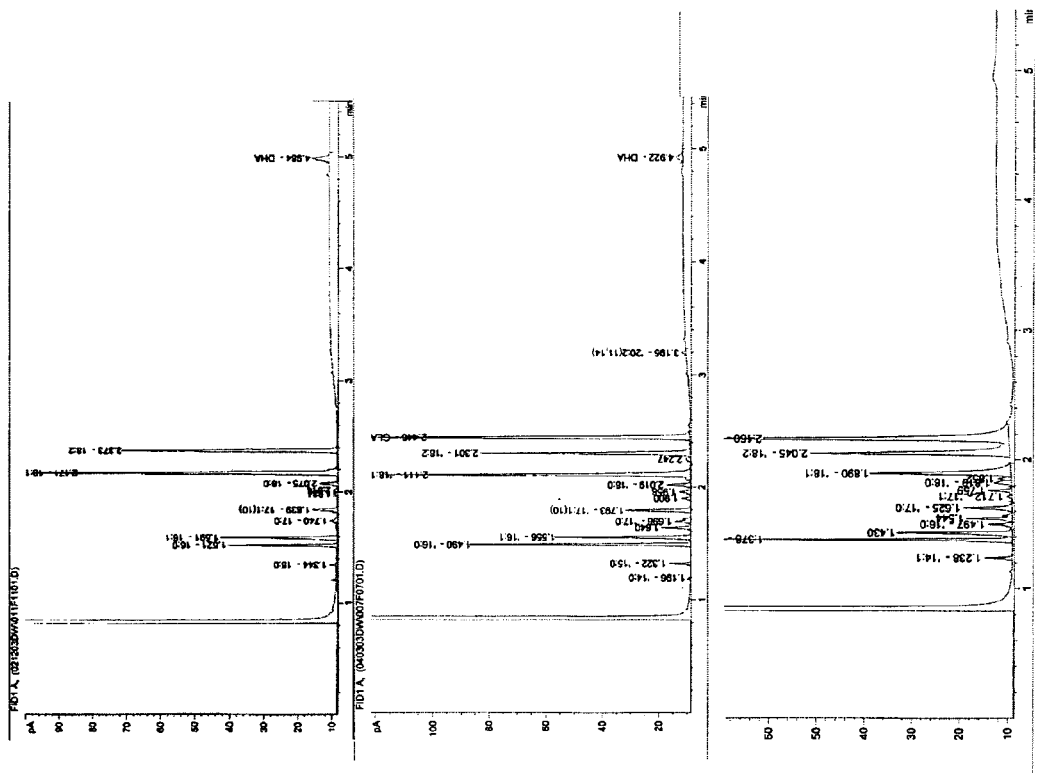

Duplicate GC analyses of one transformant containing pDMW208 showed that the average GLA content was 25.9% of the total lipids, with a standard deviation of 0.42. Duplicate GC analysis of two transformants containing pDMW208D62 showed that the average GLA content was 34% of the total lipids, with a standard deviation of 2.2. There was no GLA detected in the wildtype Yarrowia strain ATCC #76982. The results are shown in FIG. 6 and in Table 4 below. Fatty acids are identified as 16:0, 16:1, 18:0, 18:1 (oleic acid), 18:2 (LA) and GLA; and the composition of each is presented as a % of the total fatty acids.

TABLE 4

GC Analysis Of Fatty Acids In *Yarrowia lipolytica*

| Strain | % 16:0 | % 16:1 | % 18:0 | % 18:1 | % 18:2 | % GLA |
|---|---|---|---|---|---|---|
| Wildtype | 14 | 11 | 3.5 | 34.8 | 31 | 0 |
| pDMW208 | 11.9 | 8.6 | 1.5 | 24.4 | 17.8 | 25.9 |
| pDMW208D62 | 16.2 | 1.5 | 0.1 | 17.8 | 22.2 | 34.0 |

These results demonstrate that *Yarrowia lipolytica* strains transformed with two copies each of the Δ6 desaturase and Δ12 desaturase genes (i.e., pDMW208D62) produced about 30.8% more GLA than the strains transformed a single copy each of Δ6 desaturase and Δ12 desaturase genes (i.e., pDMW208).

Example 6 (Prophetic)

Synthesis of a Codon-Optimized Δ6 Desaturase Gene

Significant improvements in GLA production could readily be obtained by codon-optimizing the *S. diclina* Δ6 desaturase (contained within SEQ ID NO:22) to enhance its expression in *Yarrowia*. This would be possible by designing a codon-optimized Δ6 desaturase gene based on the codon usage and signature of structural genes in *Y. lipolytica* and then synthesizing the gene in vitro to enable its increased efficiency in the host (with respect to the wildtype gene), according to the methodology presented in WO2004/101753, Example 4.

Specifically, both the preferred codon usage in *Y. lipolytica* and an analysis of the consensus sequence (i.e., SEQ ID NO:41) around the 'ATG' initiation codon of 79 genes in *Y. lipolytica* is presented in WO2004/101753. Design of a codon-optimized Δ6 desaturase gene should rely on these teachings, to further optimize expression of the gene.

Example 7 (Prophetic)

Increased GLA Production Using Fructose-Bisphosphate Aldolase Regulatory Sequences To further improve the production of GLA in *Yarrowia lipolytica*, fructose-bisphosphate aldolase (FBA) regulatory sequences could be used to drive expression of the Δ12 and/or Δ6 desaturase genes, instead of the TEF and GPD promoters used in the chimeric genes described in Examples 2 and 3. Specifically, WO 2005/049805 describes a *Y. lipolytica* FBA and FBAIN promoter; the FBA promoter (contained within SEQ ID NO:42) was 2.2 times stronger than the GPD promoter in *Yarrowia*, while the FBAIN promoter (SEQ ID NO:43, comprising 826 bp upstream of the fba1 gene and 169 bp downstream of the putative initiation codon) was about 6.6 times stronger than the GPD promoter (activity was measured according to GUS expression). One of skill in the art of molecular cloning could readily modify plasmid pDMW208 and/or pDMW208D62 to encompass either of these strong promoters, or a portion thereof, as a means to increase GLA expression.

Example 8 (Prophetic)

Increased GLA Production Using a Heterologous Δ12 Desaturase

To further improve the production of GLA in *Yarrowia lipolytica*, the Δ12 desaturase gene from *Fusarium moniliforme* can be over-expressed, instead of, or in addition to, the endogenous Δ12 desaturase gene of *Y. lipolytica*. Specifically, previous work has demonstrated that the *F. moniliforme* Δ12 desaturase was more efficient than the *Y. lipolytica* Δ12 desaturase in producing 18:2 in *Y. lipolytica* (i.e., 68% product accumulation of LA versus 59% product accumulation of LA, which corresponds to a difference in percent substrate conversion [calculated as ([18:2]/ [18:1+18:2])*100] of 85% versus 74%; WO 2005/047485). In this cited application, expression of the *F. moniliforme* Δ12 desaturase gene under the control of the TEF promoter in *Y. lipolytica* was compared directly to expression of a chimeric gene encoding the *Y. lipolytica* Δ12 desaturase under the control of the TEF promoter. On the basis of these results, expression of the fungal *F. moniliforme* Δ12 desaturase (SEQ ID NOs:44 and 45) is preferred relative to the *Y. lipolytica* Δ12 desaturase as a means to engineer an oleaginous yeast that accumulates oils enriched in GLA. One of skill in the art of molecular cloning could readily modify plasmid pDMW208 and/or pDMW208D62 such that the Δ12 desaturase from *F. moniliforme* was expressed, as a means to increase GLA expression.

Furthermore, in some cases, it may prove advantageous to replace the native *Yarrowia lipolytica* Δ12 desaturase with the *F. moniliforme* Δ12 desaturase. Although both Δ12 desaturases catalyze the conversion of oleic acid to LA, the two enzymes differ in their overall specificity; specifically, the Applicants have determined that the *F. moniliforme* Δ12 desaturase has a higher loading capacity of LA onto the sn-2 position of a phosphotidylcholine substrate (thereby facilitating the subsequent reaction by Δ6 desaturase) than the *Y. lipolytica* Δ12 desaturase. On this basis, overexpression of the *F. moniliforme* Δ12 desaturase in conjunction with a knock-out of the *Y. lipolytica* Δ12 desaturase may result in increased product for subsequent conversion to GLA.

Example 9 (Prophetic)

Increased GLA Production Using a Heterologous $C_{16/18}$ Elongase Gene

To further improve the production of GLA in *Yarrowia lipolytica*, a gene encoding a $C_{16/18}$ elongase can be used to push the carbon from palmitate (16:0) to stearic acid (18:0), thereby increasing the substrate availability of stearic acid. A Δ9 desaturase then converts stearic acid directly to oleic acid (18:1), the substrate of the Δ12 desaturase (FIG. 1). This strategy for increasing the amount of C18 fatty acids in the total lipids has been successfully utilized in a co-pending application (U.S. Patent Application No. 60/624,812), to enable increased production of EPA. Specifically, the $C_{16/18}$ elongase from *Rattus norvegicus* [GenBank Accession No. AB071986]) was codon-optimized for expression in *Y. lipolytica* ("rELO2S"; SEQ ID NOs:46 and 48) and then expressed as a chimeric TEF::codon-optimized $C_{16/18}$ elongase::Pex20 gene.

It would be expected that over-expression of the codon-optimized $C_{16/18}$ elongase in conjunction with both a Δ6 desaturase and Δ12 desaturase will result in increased production of GLA in the host. Furthermore, the source of the $C_{16/18}$ elongase is not limiting in the invention herein.

---

What is claimed is:

1. A method for producing γ-linolenic acid comprising:
   a) providing an oleaginous *Yarrowia* sp. comprising:
      i) the nucleic acid sequence of SEQ ID NO:9 encoding a peptide having Δ6 desaturase activity;
      ii) the nucleic acid sequence of SEQ ID NO:39 encoding a peptide having Δ12 desaturase activity; and
      iii) a source of desaturase substrate selected from the group consisting of oleic acid and linoleic acid;
   b) growing the yeast of step (a) in the presence of a fermentable carbon source whereby at least 15% γ-linolenic acid in the total lipids is produced; and
   c) optionally, recovering the γ-linolenic acid.

2. A method according to claim 1 wherein the at least one genetic construct encoding the polypeptide having Δ6 desaturase activity is in multicopy in the oleaginous yeast.

3. A method according to claim 1 wherein the at least one genetic construct encoding the polypeptide having Δ12 desaturase activity is in multicopy in the oleaginous yeast.

4. A method according to claim 1 wherein the at least one genetic construct encoding the polypeptide having Δ12 desaturase activity is integrated into at least one genetic loci selected from the group consisting of the zeta loci, the Ura3 loci, the Leu 2 loci, the Lys5 loci, the Aco2 loci, the Pox3 loci, the Lip1 loci and the Lip2 loci.

5. A method according to claim 1 wherein the at least one genetic construct encoding the polypeptide having Δ6 desaturase activity is integrated into at least one genetic loci selected from the group consisting of the zeta loci, the Ura3 loci, the Leu 2 loci, the Lys5 loci, the Aco2 loci, the Pox3 loci, the Lip1 loci and the Lip2 loci.

6. A method according to claim 1 wherein the at least one genetic construct encoding the polypeptide having Δ6 desaturase activity is under the control of a strong promoter isolated from genes selected from the group consisting of: alcohol dehydrogenase, glyceraldehyde-3-phosphate-dehydrogenase, phosphoglycerate mutase, fructose-bisphosphate aldolase, glycerol-3-phosphate o-acyltransferase, phosphoglucose isomerase, phosphoglycerate kinase, acid phosphatase, lactase, metallothionein and glucoamylase.

7. A method according to claim 1 wherein the at least one genetic construct encoding the polypeptide having Δ12 desaturase activity is under the control of a strong promoter isolated from genes selected from the group consisting of: alcohol dehydrogenase, glyceraldehyde-3-phosphate-dehydrogenase, phosphoglycerate mutase, fructose-bisphosphate aldolase, glycerol-3-phosphate o-acyltransferase, phosphoglucose isomerase, phosphoglycerate kinase, acid phosphatase, lactase, metallothionein and glucoamylase.

8. A method according to claim 1 wherein at least about 20% γ-linolenic acid in the total lipids is produced.

9. A method according to claim 1 wherein the source of desaturase substrate is endogenous to the oleaginous yeast.

10. A production host cell for the production of γ-linolenic acid comprising:
    a) a background *Yarrowia* sp. comprising:
       i) the nucleic acid sequence of SEQ ID NO:9 encoding a peptide having Δ6 desaturase activity;
       ii) the nucleic acid sequence of SEQ ID NO:39 encoding a peptide having Δ12 desaturase activity,
    wherein at least one of said genetic constructs of (i) or (ii) is over-expressed and whereby at least 15% γ-linolenic acid in the total lipids is produced.

11. A production host cell according to claim 10 wherein the background *Yarrowia* sp. is devoid of any native gene encoding a polypeptide having Δ12 desaturase activity.

12. A production host cell according to claim 10 wherein at least one of said genetic constructs is integrated into the *Yarrowia* sp. genome at a gene locus selected from the group consisting of: zeta, Ura3, Leu2, Lys5, Aco2, Pox3, Lip1 and the Lip2 gene locus.

* * * * *